US008846021B2

(12) United States Patent
Charles

(10) Patent No.: US 8,846,021 B2
(45) Date of Patent: Sep. 30, 2014

(54) ACRYLOYLOXYETHYLPHOSPHORYLCHOLINE CONTAINING POLYMER CONJUGATES AND THEIR PREPARATION

(71) Applicant: Oligasis, LLC, Palo Alto, CA (US)

(72) Inventor: Stephen A. Charles, San Jose, CA (US)

(73) Assignee: Oligasis, LLC, Palo Alto, CA (US)

( * ) Notice: Subject to any disclaimer, the term of this patent is extended or adjusted under 35 U.S.C. 154(b) by 0 days.

(21) Appl. No.: 13/959,563

(22) Filed: Aug. 5, 2013

(65) Prior Publication Data

US 2013/0337534 A1   Dec. 19, 2013

Related U.S. Application Data

(63) Continuation of application No. 12/281,071, filed as application No. PCT/US2007/005372 on Feb. 28, 2007, now abandoned.

(60) Provisional application No. 60/776,916, filed on Feb. 28, 2006.

(51) Int. Cl.
| A61K 31/74 | (2006.01) |
| C08F 30/02 | (2006.01) |
| C08F 130/02 | (2006.01) |
| C08F 230/02 | (2006.01) |
| C08F 293/00 | (2006.01) |
| A61K 47/48 | (2006.01) |

(52) U.S. Cl.
CPC ....... *A61K 47/48176* (2013.01); *C08F 293/005* (2013.01)
USPC ........................................ 424/78.31; 526/277

(58) Field of Classification Search
None
See application file for complete search history.

(56) References Cited

U.S. PATENT DOCUMENTS

| 5,741,923 A | 4/1998 | Driver et al. |
| 5,763,548 A | 6/1998 | Matyjaszewski et al. |
| 5,789,487 A | 8/1998 | Matyjaszewski et al. |
| 5,807,937 A | 9/1998 | Matyjaszewski et al. |
| 5,945,491 A | 8/1999 | Matyjaszewski et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,162,882 A | 12/2000 | Matyjaszewski et al. |
| 6,407,187 B1 | 6/2002 | Matyjaszewski et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,627,314 B2 | 9/2003 | Matyjaszewski et al. |
| 6,759,491 B2 | 7/2004 | Matyjaszewski et al. |
| 6,790,919 B2 | 9/2004 | Matyjaszewski et al. |
| 6,852,816 B2 | 2/2005 | Lewis et al. |
| 6,887,962 B2 | 5/2005 | Matyjaszewski et al. |
| 7,019,082 B2 | 3/2006 | Matyjaszewski et al. |
| 7,049,373 B2 | 5/2006 | Matyjaszewski et al. |
| 7,056,455 B2 | 6/2006 | Matyjaszewski et al. |
| 7,064,166 B2 | 6/2006 | Matyjaszewski et al. |
| 7,125,938 B2 | 10/2006 | Matyjaszewski et al. |
| 7,157,530 B2 | 1/2007 | Matyjaszewski et al. |
| 7,300,990 B2 | 11/2007 | Lewis et al. |
| 7,348,424 B2 | 3/2008 | Miyazawa et al. |
| 7,569,655 B2 | 8/2009 | Pacetti et al. |
| 2003/0143596 A1* | 7/2003 | Bentley et al. ................. 435/6 |
| 2004/0063881 A1 | 4/2004 | Lewis et al. |
| 2004/0253596 A1 | 12/2004 | Pawlak et al. |
| 2005/0112088 A1* | 5/2005 | Zhao et al. ................. 424/78.27 |
| 2005/0123501 A1 | 6/2005 | Lewis |
| 2005/0159556 A1 | 7/2005 | Lewis et al. |
| 2005/0180945 A1 | 8/2005 | Chaikof et al. |
| 2006/0135714 A1 | 6/2006 | Lewis et al. |
| 2006/0165804 A1 | 7/2006 | Lewis et al. |
| 2006/0217285 A1 | 9/2006 | Destarac |
| 2007/0141104 A1 | 6/2007 | Hauenstein |
| 2008/0124450 A1 | 5/2008 | Pacetti |
| 2008/0147178 A1 | 6/2008 | Pacetti et al. |
| 2010/0158850 A1 | 6/2010 | Baker, Jr. et al. |

FOREIGN PATENT DOCUMENTS

| EP | 1465933 B1 | 8/2007 |
| EP | 1592719 B1 | 3/2008 |
| EP | 1732621 B1 | 12/2009 |
| EP | 2260873 A1 | 12/2010 |
| JP | 2010-117189 A | 5/2010 |
| WO | WO 00/59968 A1 | 10/2000 |
| WO | WO 02/28929 A1 | 4/2002 |
| WO | WO 03/062290 A1 | 7/2003 |
| WO | WO 03/074026 A1 | 9/2003 |
| WO | WO 03/074090 A1 | 9/2003 |
| WO | WO 2004/063237 A1 | 7/2004 |
| WO | WO 2004/113394 A2 | 12/2004 |
| WO | WO 2005/028539 A2 | 3/2005 |
| WO | WO 2005/058367 A2 | 6/2005 |
| WO | WO 2007/005253 A1 | 1/2007 |

(Continued)

OTHER PUBLICATIONS

Crowe et al. Proceedings of the National Academy of Science 1994 91:1386-1390.*
Pasut et al. Expert Opinion on Therapeutic Patents 2004 14:859-894.*
Bontempo, et al., "Cysteine-Reactive Polymers Synthesized by Atom Transfer Radical Polymerization for Conjugation to Proteins," *J. Am. Chem. Soc.*, (2004), 126, pp. 15372-15373.
Chen, et al., "Lubrication at Physiological Pressures by Polyzwitterionic Brushes," *Science*, (2009), 323, pp. 1698-1701.

(Continued)

*Primary Examiner* — Robert A Wax
*Assistant Examiner* — Caralynne Helm
(74) *Attorney, Agent, or Firm* — Alston & Bird LLP

(57) ABSTRACT

The present invention relates to polymeric reagents and conjugates thereof, methods for synthesizing the polymeric reagents and conjugates, pharmaceutical compositions comprising the conjugates and methods of using the polymer conjugates including therapeutic methods where conjugates are administered to patients.

19 Claims, 13 Drawing Sheets

(56) References Cited

FOREIGN PATENT DOCUMENTS

| WO | WO 2007/075534 A2 | 7/2007 |
|---|---|---|
| WO | WO 2007/100902 A3 | 9/2007 |
| WO | WO 2008/098930 A1 | 8/2008 |
| WO | WO 2008/112257 A1 | 9/2008 |
| WO | WO 2008/112289 A2 | 9/2008 |
| WO | WO 2010/068862 A2 | 6/2010 |
| WO | WO 2010/068864 A2 | 6/2010 |
| WO | WO 2011/075185 A1 | 6/2011 |
| WO | WO 2011/075736 A2 | 6/2011 |
| WO | WO 2011/130694 A2 | 10/2011 |
| WO | WO 2013/059137 A1 | 4/2013 |

OTHER PUBLICATIONS

Chen, et al., "Polymeric Phosphorylcholine-Camptothecin Conjugates Prepared by Controlled Free Radical Polymerization and Click Chemistry," *Bioconjugate Chem.*, (2009), 20:12, pp. 2331-2341.

Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).

Da Pieve, et al., "Modification of Thiol Functionalized Aptamers by Conjugation of Synthetic Polymers," *Bioconjugate Chem.*, (2010), 21:1, pp. 169-174.

Dong, et al., "ARGET ATRP of 2-(Dimethylamino)ethyl Methacrylate as an Intrinsic Reducing Agent," *Macromolecules*, (2008), 41:19, pp. 6868-6870.

Dong, et al., "Well-Defined High-Molecular-Weight Polyacrylonitrile via Activators Regenerated by Electron Transfer ATRP," *Macromolecules*, (2007), 40:9, pp. 2974-2977.

Haddleton, et al., "Phenolic Ester-Based Initiators for Transition Metal Mediated Living Polymerization," *Macromolecules*, (1999), 32, pp. 8732-8739.

Heise, et al., "Investigation of the Initiation Behavior of a Dendritic 12-Arm Initiator in Atom Transfer Radical Polymerization," *Macromolecules*, (2001), 34:11, pp. 3798-3801.

Heredia, et al., "In Situ Preparation of Protein-'Smart' Polymer Conjugates with Retention of Bioactivity," *J. Am. Chem. Soc.*, (2005), 127, pp. 16955-16960.

Hong, et al., "Preparation of Segmented Copolymers in the Presence of an Immobilized/Soluble Hybrid ATRP Catalyst System," *Macromolecules*, (2003), 36:1, pp. 27-35.

Iwasaki, et al., "Platelet compatible blood filtration fabrics using a phosphorylcholine polymer having high surface mobility," *Biomaterials*, (2003), 24, pp. 3599-3604.

Jakubowski, et al., "Activators Regenerated by Electron Transfer for Atom Transfer Radical Polymerization of Styrene," *Macromolecules*, (2006), 39:1, pp. 39-45.

Kizhakkedathu, et al., "Synthesis of Well-Defined Environmentally Responsive Polymer Brushes by Aqueous ATRP," *Macromolecules*, (2004), 37:3, pp. 734-743.

Kwiatdowski, et al., "High Molecular Weight Polymethacrylates by AGET ATRP under High Pressure," *Macromolecules*, (2008), 41:4, pp. 1067-1069.

Lacciardi, et al., "Synthesis of Novel Folic Acid-Functionalized Biocompatible Block Copolymers by Atom Transfer Radical Polymerization for Gene Delivery and Encapsulation of Hydrophobic Drugs," *Biomacromolecules*, (2005), 6:2, pp. 1085-1096.

Lena, et al., "Investigation of metal ligand affinities of atom transfer radical polymerization catalysts with a quadrupole ion trap," *Dalton Transactions*, (2009), 41, pp. 8884-8889.

Lewis, et al., "Crosslinkable coatings from phosphorylcholine-based polymers," *Biomaterials*, (2001), 22, pp. 99-111.

Lewis, et al., "Poly(2-methacryloyloxyethyl phosphorylcholine) for Protein Conjugation," *Bioconjugate Chem.*, (2008), 19:11, pp. 2144-2155.

Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," *Macromolecules*, (2006), 39:2, pp. 893-896.

Ma, et al., "Synthesis of Biocompatible Polymers. 1. Homopolymerization of 2-Methacryloyloxyethyl Phosphorylcholine via ATRP in Protic Solvents: An Optimization Study," *Macromolecules*, (2002), 35:25, pp. 9306-9314.

Ma, et al., "Well-Defined Biocompatible Block Copolymers via Atom Transfer Radical Polymerization of 2-Methacryloyloxyethyl Phosphorylcholine in Protic Media," *Macromolecules*, (2003), 36:10, pp. 3475-3484.

Mantovani, et al., "Design and Synthesis of N-Maleimido-Functionalized Hydrophilic Polymers via Copper-Mediated Living Radical Polymerization: A Suitable Alternative to PEGylation," *J. Am. Chem. Soc.*, (2005), 127, pp. 2966-2973.

Matyjaszewski, et al., "Diminishing catalyst concentration in atom transfer radical polymerization with reducing agents," *PNAS*, (Oct. 17, 2006), 103:42, pp. 15309-15314.

Min, et al., "Use of Ascorbic Acid as Reducing Agent for Synthesis of Well-Defined Polymers by ARGET ATRP," *Macromolecules*, (2007), 40:6, pp. 1789-1791.

Miyamoto, et al., "Effect of water-soluble phospholipid polymers conjugated with papain on the enzymatic stability," *Biomaterials*, (2004), 25, pp. 71-76.

Ng, et al., "Successful Cu-Mediated Atom Transfer Radical Polymerization in the Absence of Conventional Chelatic Nitrogen Ligands," *Macromolecules*, (2010), 43:2, pp. 592-594.

Oh, et al., "Preparation of Poly(oligo(ethylene glycol) monomethyl ether methacrylate) by Homogeneous Aqueous AGET ATRP," *Macromolecules*, (2006), 39:9, pp. 3161-3167.

PCT/US2007/05372 International Search Report and Written Opinion mailed Aug. 8, 2008.

PCT/US2010/034252 International Search Report and Written Opinion mailed Sep. 9, 2010.

PCT/US2010/61358 International Search Report and Written Opinion mailed May 9, 2011.

PCT/US2011/32768 International Search Report and Written Opinion mailed Dec. 16, 2011.

PCT/US2012/60301 International Search Report and Written Opinion mailed Feb. 27, 2013.

Pietrasik, et al., "Synthesis of High Molecular Weight Poly(styrene-co-acrylonitrile) Copolymers with Controlled Architecture," *Macromolecules*, (2006), 39:19, pp. 6384-6390.

Ranganathan, et al., "Synthesis of Thermoresponsive Mixed Arm Star Polymers by Combination of RAFT and ATRP from a Multifunctional Core and Its Self-Assembly in Water," *Macromolecules*, (2008), 41:12, pp. 4226-4234.

Roberts, et al., "Chemistry for peptide and protein PEGylation," *Advanced Drug Delivery Reviews*, (2002), 54, pp. 459-476.

Ruiz, et al., "Synthesis, structure and surface dynamics of phosphorylcholine functional biomimicking polymers," *Biomaterials*, (1998), 19, pp. 987-998.

Ryan, et al., "Conjugation of salmon calcitonin to a combed-shaped end functionalized poly(poly(ethylene glycol) methyl ether methacrylate) yields a bioactive stable conjugate," *Journal of Controlled Release*, (2009), 135, pp. 51-59.

Sakaki, et al., "Stabilization of an antibody conjugated with enzyme by 2-methacryloyloxyethyl phosphorylcholine copolymer in enzyme-linked immunosorbent assay," *J Biomed Mater Res*, (1999), 47, pp. 523-528.

Samanta, et al., "End-Functionalized Phosphorycholine Methacrylates and their Use in Protein Conjugation," *Biomacromolecules*, (2008), 9:(10), pp. 2891-2897.

Sayers, et al., "The Reduced Viscosity of PolyPEG® Compared with Linear PEG," Poster, Warwick Effect Polymers Ltd, retrieved from <http:www.wep-ltd.co.uk> on Feb. 11, 2009.

Tao, et al., "α-Aldehyde Terminally Functional Methacrylic Polymers from Living Radical Polymerization: Application in Protein Conjugation 'Pegylation'," *J. Am. Chen. Soc.*, (2004), 126:41, pp. 13220-13221.

Wang, et al., "Controlled/'Living' Radical Polymerization. Atom Transfer Radical Polymerization in the Presence of Transition-Metal Complexes," *J. Am. Chem. Soc.*, (1995), 117:20, pp. 5614-5615.

Warwick Effect Polymers, PowerPoint presentation, "Polymers for the Healthcare and Speciality Materials Industries," Jan. 2009, pp. 1-29.

Yaseen, et al., "The Structure of Zwitterionic Phosphocholine Surfactant Monolayers," *Langmuir*, (2006), 22:13, pp. 5825-5832.

\* cited by examiner

APPRLICDSRVLERYLLEAKEAENITGCAEHCSLNENITVPDTKVNFYAWKRMEVG
QQAVEVWQGLALLSEAVLRGQALLVNSSQPWEPLQLHVDKAVSGLRSLTTLLRALG
AQKEAISPPDAASAAPLRTITADTFRKLFRVYSNFLRGKLKLYTGEACRTGD

FIG. 1

TPLGPASSLPQSFLLKCLEQVRKIQGDGAALQEKLCATYKLCHPEELVLLGHSLGIPW
APLSSCPSQALQLAGCLSQLHSGLFLYQGLLQALEGISPELGPTLDTLQLDVADFATTI
WQQMEELGMAPALQPTQGAMPAFASAFQRRAGGVLVASHLQSFLEVSYRVLRHLA
QP

FIG. 2

ACRYLOYLOXYETHYLPHOSPHORYLCHOLINE CONTAINING POLYMER CONJUGATES AND THEIR PREPARATION

CROSS-REFERENCES TO RELATED APPLICATIONS

This application is a continuation of U.S. Ser. No. 12/281,071 filed Aug. 28, 2008, which is a National Stage of International Application PCT/US2007/05372 filed Feb. 28, 2007, which claims the benefit of U.S. provisional patent application No. 60/776,916 filed Feb. 28, 2006, the disclosure of which is incorporated in its entirety herein by reference.

FIELD OF THE INVENTION

The present invention relates to polymeric reagents and conjugates thereof, methods for synthesizing the polymeric reagents and conjugates, pharmaceutical compositions comprising the conjugates and methods of using the polymer conjugates including therapeutic methods where conjugates are administered to patients.

BACKGROUND OF THE INVENTION

Efforts to formulate biologically active agents for delivery must deal with a variety of variables including the route of administration, the biological stability of the active agent and the solubility of the active agents in physiologically compatible media. Choices made in formulating biologically active agents and the selected routes of administration can affect the bioavailability of the active agents. For example, the choice of parenteral administration into the systemic circulation for biologically active proteins and polypeptides avoids the proteolytic environment found in the gastrointestinal tract. However, even where direct administration, such as by injection, of biologically active agents is possible, formulations may be unsatisfactory for a variety of reasons including the generation of an immune response to the administered agent and responses to any excipients including burning and stinging. Even if the active agent is not immunogenic and satisfactory excipients can be employed, biologically active agents can have a limited solubility and short biological half-life that can require repeated administration or continuous infusion, which can be painful and/or inconvenient.

For some biologically active agents a degree of success has been achieved in developing suitable formulations of bioactive agents by conjugating the agents to water soluble polymers. The conjugation of biologically active agents to water soluble polymers is generally viewed as providing a variety of benefits for the delivery of biologically active agents, and in particular, proteins and peptides. Among the water soluble polymers employed, polyethylene glycol (PEG), which has been most widely conjugated to a variety of biologically active agents including biologically active peptides. A reduction in immunogenicity or antigenicity, increased half-life, increased solubility, decreased clearance by the kidney and decreased enzymatic degradation have been attributed to conjugates of a variety of water soluble polymers and bioactive agents, including PEG conjugates. As a result of these attributes, the polymer conjugates of biologically active agent require less frequent dosing and may permit the use of less of the active agent to achieve a therapeutic endpoint. Less frequent dosing reduces the overall number of injections, which can be painful and which require inconvenient visits to healthcare professionals.

Although some success has been achieved with PEG conjugation, "PEGylation" of biologically active agents, remains a challenge as PEG conjugation may result in the loss of biological activity. A variety of theories have been advanced to account for loss of biological activity upon conjugation with PEG. These include blockage of necessary sites for the agent to interact with other biological components, either by the conjugation linkage or by the agent being buried within the PEG conjugate, particularly where the polymer is long and may "wrap" itself around some or the active agent, thereby blocking access to potential ligands required for activity.

Branched forms of PEG for use in conjugate preparation have been introduced to alleviate some of the difficulties encountered with the use of long straight PEG polymer chains. While branched polymer may overcome some of the problems associated with conjugates formed with long linear PEG polymers, neither branched nor linear PEG polymer conjugates completely resolve the issues associated with the use of conjugated bioactive agents. Both linear and branched PEG conjugates can, for example, suffer from rates of degradation that are either too long or too short. A rapid rate of degradation can result in a conjugate having too short of an in vivo half-life, whereas, too slow of a rate of degradation can result in an unacceptable long conjugate half-life in vivo.

In view of the recognized advantages of conjugating bioactive agents to water soluble polymers, and the limitations of water soluble polymers such as PEG in forming conjugates suitable for therapeutic purposes, additional water soluble polymers for forming conjugates with bioactive agents are desirable. Water soluble polymers, particularly those which have many of the advantages of PEG for use in conjugate formation, and which do not suffer from the disadvantages observed with PEG as a conjugating agent would be desirable for use in forming therapeutic and diagnostic agents. To this end, polymers of 2-methacryloyloxyethyl-phosphorylcholine are set forth for use in preparing conjugates of biologically active agents.

BRIEF SUMMARY OF THE INVENTION

The present invention relates to polymeric reagents and conjugates thereof, methods for synthesizing the polymeric reagents and conjugates, pharmaceutical compositions comprising the conjugates and methods of using the polymer conjugates including therapeutic methods where conjugates are administered to patients.

In a first group of embodiments, the invention provides compounds of formula (Ia) or a salt, hydrate, or solvate thereof:

$$(X\text{-}(Sp^1)_n)_a\text{-}L\text{-}(K)_b \tag{Ia}$$

where
K is a group of the formula

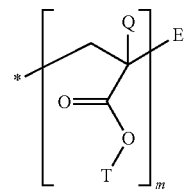

each occurrence of Q is independently selected from the group consisting of H and $C_{1-4}$alkyl;

each occurrence of T is independently selected from the group consisting of H, —$C_{1-4}$alkyl, and —$C_{1-4}$alkyl—O—PC, where PC denotes a phosphorylcholine group, with the proviso that one or more T groups is —$C_{1-4}$alkyl—O—PC;
each occurrence of E is independently selected from the group consisting of halo and Nu wherein Nu represents a nucleophilic group;
$Sp^1$ is a spacer group;
X is a reactive group or a protected form thereof;
n is an integer ranging from 0 to 1, wherein when n is 0, $Sp^1$ is a bond;
m is an integer ranging from 2 to 2,000;
a is an integer ranging from 1 to 8;
b is an integer ranging from 1 to 8;
L is selected from the group consisting of $C_{1-4}$alkyl, cycloalkyl, carboxy$C_{1-4}$alkyl, carboxycycloalkyl, $C_{1-4}$alkoxy$C_{1-4}$alkyl and cyclic alkyl ether; and
* indicates the point of attachment of each K group to said L.

Another group of embodiments is directed to compounds of formula (IIa), which are embodiments of compounds of formula (Ia) where a and b are both 1, (IIa)

where
each occurrence of Q is independently selected from the group consisting of H, methyl, and ethyl;
each occurrence of T is independently selected from the group consisting of H, —$CH_3$, —$CH_2$—$CH_3$, and —$CH_2$—$CH_2$—O—PC, where PC denotes a phosphorylcholine group, with the proviso that one or more T groups is —$CH_2$—$CH_2$—O—PC;
E is independently selected from the group consisting of Br, Cl, I, —$NH_2$, —NH($C_{1-4}$ alkyl), —N($C_{1-4}$ alkyl)$_2$, —OH, —O—($C_{1-4}$ alkyl), and —O—($C_{1-4}$ fluoro-substituted alkyl);
$Sp^1$ is a spacer group;
X is a reactive group or a protected form thereof;
n is 0 or 1, wherein when n is 0, $Sp^1$ is a bond;
m is an integer ranging from 2 to 2,000; and
L is selected from the group consisting of $C_{1-4}$allyl, cycloalkyl, carboxy$C_{1-4}$alkyl, carboxycycloalkyl, $C_{1-4}$alkoxy$C_{1-4}$alkyl and cyclic alkyl ether.

Another group of embodiments is directed to compounds of formula (IIIa), which are embodiments of compounds of formula (Ia) where a=2 and b=1, (IIIa)

Another group of embodiments is directed to compounds of formula (IVa), which are embodiments of compounds of formula (Ia) where a=1 and b=2, (IVa)

Another group of embodiments is directed to compounds of formula (Va), which are embodiments of compounds of formula (Ia) where a=2 and b=2, (Va)

Another group of embodiments is directed to compounds of formulas (Ia) (IIa), (IIIa) (IVa) and (Va) where:
each occurrence of Q is independently selected from the group consisting of H, methyl, and ethyl;
each occurrence of T is independently selected from the group consisting of H, —$CH_3$, —$CH_2$—$CH_3$, and —$CH_2$—$CH_2$—O—PC, where PC denotes a phosphorylcholine group, with the proviso that one or more T groups is —$CH_2$—$CH_2$—O—PC;
each occurrence of E is independently selected from the group consisting of Br, Cl, I, —$NH_2$, —NH($C_{1-4}$ alkyl), —N($C_{1-4}$ alkyl)$_2$, —OH, —O—($C_{1-4}$ alkyl), and —O—($C_{1-4}$ fluoro-substituted alkyl);
$Sp^1$ is selected from the group consisting of: —$C_{1-12}$ alkyl-, —$C_{3-12}$ cycloalkyl-, —($C_{1-8}$ alkyl)-($C_{3-12}$ cycloalkyl)-($C_{0-8}$ alkyl)-, —$(CH_2)_{1-12}$O—, (—$(CH_2)_{1-6}$—O—$(CH_2)_{1-6}$—)$_{1-12}$—, (—$(CH_2)_{1-4}$—NH—$(CH_2)_{1-4})_{1-12}$—, (—$(CH_2)_{1-4}$—O—$(CH_2)_{1-4})_{1-12}$—O—, (—$(CH_2)_{1-4}$—O—$(CH_2)_{1-4}$—)$_{1-12}$O—$(CH_2)_{1-12}$—, —$(CH_2)_{1-12}$—(C=O)—O—, —$(CH_2)_{1-12}$—O—(C=O)—, -(phenyl)-$(CH_2)_{1-3}$—(C=O)—O—, -(phenyl)-$(CH_2)_{1-3}$—(C=O)—NH—, —($C_{1-6}$ alkyl)-(C=O)—O—($C_{0-6}$ alkyl)-, —(CH$_2$)$_{1-12}$—(C═O)—O—(CH$_2$)$_{1-12}$—, —CH(OH)—CH(OH)—(C═O)—O—CH(OH)—CH(OH)—(C═O)—NH—, —S-maleimido-(CH$_2$)$_{1-6}$—, —S-maleimido-(C$_{1-3}$ alkyl)-(C═O)—NH—, —S-maleimido-(C$_{1-3}$ alkyl)-(C$_{5-6}$ cycloalkyl)-(C$_{0-3}$ alkyl)-, —(C$_{1-3}$ alkyl)-(C$_{5-6}$ cycloalkyl)-(C$_{0-3}$ alkyl)-(C═O)—O—, —(C$_{1-3}$ alkyl)-(C$_{5-6}$ cycloalkyl)-(C$_{0-3}$ alkyl)-(C═O)—NH—, —S-maleimido-(C$_{0-3}$alkyl)-phenyl-(C$_{0-3}$alkyl)-, —(C$_{0-3}$ alkyl)-phenyl-(C═O)—NH—, —(CH$_2$)$_{1-12}$—NH—(C═O)—, —(CH$_2$)$_{1-12}$—(C═O)—NH—, -(phenyl)-(CH$_2$)$_{1-3}$—(C═O)—NH—, —S—(CH$_2$)—(C═O)—NH-(phenyl)-, —(CH$_2$)$_{1-12}$—(C═O)—NH—(CH$_2$)$_{1-12}$—, —(CH$_2$)$_2$—(C═O)—O—(CH$_2$)$_2$—O—(C═O)—(CH$_2$)$_2$—(C═O)—NH—, —(C$_{1-6}$ alkyl)-(C═O)—N—(C$_{1-6}$ alkyl)-, acetal, ketal, acyloxyalkyl ether, —N═CH—, —(C$_{1-6}$ alkyl)-S—S—(C$_{0-6}$ alkyl)-, —(C$_{1-6}$ alkyl)-S—S—(C$_{1-6}$ alkyl)-(C═O)—O—, —(C$_{1-6}$ alkyl)-S—S—(C$_{1-6}$ alkyl)-(C═O)—NH—, —S—S—(CH$_2$)$_{1-3}$—(C═O)—NH—(CH$_2$)$_{1-4}$—NH—(C═O)—(CH$_2$)$_{1-3}$—, —S—S—(C$_{0-3}$ alkyl)-(phenyl)-, —S—S—(C$_{1-3}$-alkyl)-(phenyl)-(C═O)—NH—(CH$_2$)$_{1-5}$—, —(C$_{1-3}$ alkyl)-(phenyl)-(C═O)—NH—(CH$_2$)$_{1-5}$—(C═O)—NH—, —S—S—(C$_{1-3}$-alkyl)-, —(C$_{1-3}$-alkyl)-(phenyl)-(C═O)—NH—, —O—(C$_1$-C$_6$ alkyl)-S(O$_2$)—(C$_{1-6}$ alkyl)-O—(C═O)—NH—, —S—S—(CH$_2$)$_{1-3}$—(C═O)—, —(CH$_2$)$_{1-3}$—(C═O)—NH—N═C—S—S—(CH$_2$)$_{1-3}$—(C═O)—NH—(CH$_2$)$_{1-5}$—, —(CH$_2$)$_{1-3}$—(C═O)—NH—(CH$_2$)$_{1-5}$—(C═O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

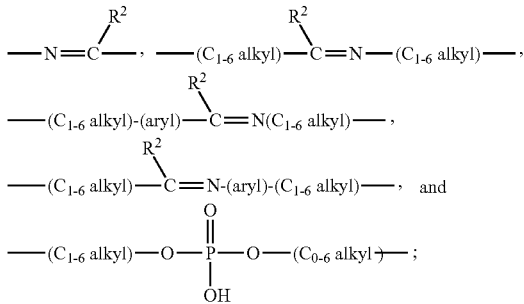

X is selected from the group consisting of: hydroxyl, thiol, disulfide, dithiopyridyl, aldehyde, aldehyde hydrate, ketone, thione, acetal, ketal, —CH(OR$^1$)$_2$, hemiacetal, hemiketal, monothioketal, dithiohemiketal, dithioketal, epoxide, thioepoxide, glyoxal, diones, amide, hydrazide, carboxyl, carboxylic acid ester, orthoester, N-hydroxysuccinimide ester, succinimidyl, maleimidyl, 1-benzotriazolyl, —CO$_2$-succinimidyl, —CO$_2$-maleimidyl, imidoester, guanido, —CO$_2$-(1-benzotriazolyl), amine, urea, carbamate, carbonate, thiourea, thiocarbamate, isocyanate, isothiocyanate, sulfone, chloroethylsulfone, alpha-beta substituted carbonyl, alpha-beta substituted carboxyl, acryloyl, acrylate, methacrylate, acrylamide, vinylsulfone, vinylpyridine, —O(C═O)—CH$_2$—I, —O(C═O)—CH$_2$—Br, —NH(C═O)—CH$_2$—I, —NH(C═O)—CH$_2$—Br, —(C═O)—CH$_2$—I, and —(C═O)—CH$_2$—Br;

n is 0 or 1, wherein when n is 0, Sp$^1$ is a bond;

m is an integer ranging from 2 to 2,000;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

R$^1$ is C$_{1-6}$ alkyl, C$_{3-6}$ cycloalkyl, or an aryl group having 5-8 endocyclic atoms;

R$^2$ is H, C$_{1-6}$ alkyl, C$_{3-6}$ cycloalkyl, or an aryl group having 5-8 endocyclic atoms;

and with respect to compounds of formula (Ia),

K is a group of the formula

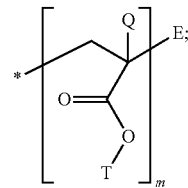

a is an integer ranging from 1-8;

b is an integer ranging from 1-8; and

* indicates the point of attachment of each K group to said L.

Another group of embodiments relates to compound comprising a biologically active agent bonded to a phosphorylcholine containing polymer.

Another group of embodiments relates to compound of formula (Ib) or a salt, hydrate, or isomer thereof:

$$(A-Z-(Sp^1)_n)_a-L-(K)_b \qquad (Ib)$$

where

K is a group of the formula

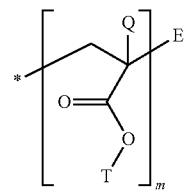

each occurrence of Q is independently selected from the group consisting of H, methyl, and ethyl;

each occurrence of T is independently selected from the group consisting of H, —C$_{1-4}$ alkyl, and —C$_{1-4}$ alkyl —O—PC, where PC denotes a phosphorylcholine group, with the proviso that one or more T groups is —C$_{1-4}$ alkyl —O—PC;

each occurrence of E is independently selected from the group consisting of halo and Nu wherein Nu represents a nucleophilic group;

Sp$^1$ is a spacer group;

n is 0 or 1, wherein when n is 0, Sp$^1$ is a bond;

m is an integer ranging from 2 to 2,000;

a is an integer ranging from 1-8;

b is an integer ranging from 1-8;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

A is a biologically active agent;

Z is the product of the reaction between a group present in said biologically active agent and a reactive group bound to said Sp$^1$ group when n is 1, or a reactive group bound to L when n is 0; and

* indicates the point of attachment of each K group to said L.

Another group of embodiments relates to compound of formula (IIb), which are embodiments of compounds of formula (Ib) where a and b are both 1:

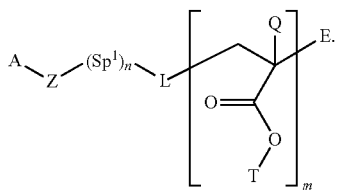

(IIb)

where
each occurrence of Q is independently selected from the group consisting of H, methyl, and ethyl;
each occurrence of T is independently selected from the group consisting of H, —$CH_3$, —$CH_2$—$CH_3$, and —CH2-CH2-O—PC, where PC denotes a phosphorylcholine group, with the proviso that one or more T groups is —CH2-CH2-O—PC;
E is independently selected from the group consisting of Br, Cl, I, —$NH_2$, —NH($C_{1-4}$ alkyl), —N($C_{1-4}$ alkyl)$_2$, —OH, —O—($C_{1-4}$ alkyl), and —O—($C_{1-4}$-fluoro-substituted alkyl);
$Sp^1$ is a spacer group;
n is 0 or 1, wherein when n is 0, $Sp^1$ is a bond;
m is an integer ranging from 2 to 2,000;
L is selected from the group consisting of $C_{1-4}$alkyl, cycloalkyl, carboxy$C_{1-4}$alkyl, carboxycycloalkyl, $C_{1-4}$alkoxy$C_{1-4}$alkyl and cyclic alkyl ether;
A is a biologically active agent; and
Z is the product of the reaction between a group present in said biologically active agent and a reactive group bound to said $Sp^1$ group when n is 1, or a reactive group bound to L when n is 0.

Another group of embodiments relates to compound of formula (IIIb), which are embodiments of compounds of formula (Ib) where a=2 and b=1,

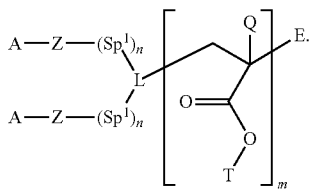

(IIIb)

Another group of embodiments relates to compound of formula (IVb), which are embodiments of compounds of formula (Ib) where a=1 and b=2,

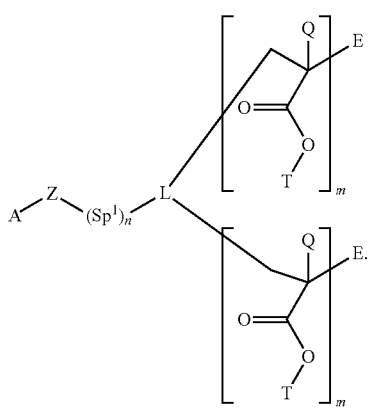

(IVb)

Another group of embodiments relates to compound of formula (Vb), which are embodiments of compounds of formula (Ib) where a=2 and b=2,

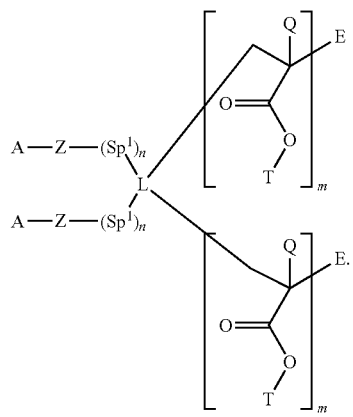

(Vb)

Another group of embodiments is directed to compounds of formulas (Ib) (IIb), (IIIb) (IVb) and (Vb),
where
each occurrence of Q is independently selected from the group consisting of H, methyl, and ethyl;
each occurrence of T is independently selected from the group consisting of H, —$CH_3$, —$CH_2$—$CH_3$, and —$CH_2$—$CH_2$—O—PC, where PC denotes a phosphorylcholine group, with the proviso that one or more T groups is —$CH_2$—$CH_2$—O—PC;
each occurrence of E is independently selected from the group consisting of Br, Cl, I, —$NH_2$, —NH($C_{1-4}$ alkyl), —N($C_{1-4}$ alkyl)$_2$, —OH, —O—($C_{1-4}$ alkyl), and —O—($C_{1-4}$-fluoro-substituted alkyl);
each occurrence $Sp^1$ is independently selected from the group consisting of: —$C_{1-12}$ alkyl-, —$C_{3-12}$ cycloalkyl-, —($C_{1-8}$ alkyl)-($C_{3-12}$ cycloalkyl)-($C_{0-8}$ alkyl)-, —$(CH_2)_{1-12}$O—, (—$(CH_2)_{1-6}$—O—$(CH_2)_{1-6}$—)$_{1-12}$—, (—$(CH_2)_{1-4}$—NH—$(CH_2)_{1-4}$)$_{1-12}$—, (—$(CH_2)_{1-4}$—O—$(CH_2)_{1-4}$)$_{1-12}$O—, (—$(CH_2)_{1-4}$—O—$(CH_2)_{1-4}$—)$_{1-12}$O—$(CH_2)_{1-12}$—, —$(CH_2)_{1-12}$—(C=O)—O—, —$(CH_2)_{1-12}$—O—(C=O)—, -(phenyl)-$(CH_2)_{1-3}$—(C=O)—O—, -(phenyl)-$(CH_2)_{1-3}$—(C=O)—NH—, —($C_{1-6}$ alkyl)-(C=O)—O—($C_{0-6}$ alkyl)-, —$(CH_2)_{1-12}$—(C=O)—O—$(CH_2)_{1-12}$—, —CH(OH)—CH(OH)—(C=O)—O—CH(OH)—CH(OH)—(C=O)—NH—, —S-maleimido-$(CH_2)_{1-6}$—, —S-maleimido-($C_{1-3}$ alkyl)-(C=O)—NH—, —S-maleimido-($C_{1-3}$ alkyl)-($C_{5-6}$ cycloalkyl)-($C_{0-3}$ alkyl)-, —($C_{1-3}$ alkyl)-($C_{5-6}$ cycloalkyl)-($C_{0-3}$ alkyl)-(C=O)—O—, —($C_{1-3}$ alkyl)-($C_{5-6}$ cycloalkyl)-($C_{0-3}$ alkyl)-(C=O)—NH—, —S-maleimido-($C_{0-3}$alkyl)-phenyl-($C_{0-3}$alkyl)-, —($C_{0-3}$ alkyl)-phenyl-(C=O)—NH—, —$(CH_2)_{1-12}$—NH—(C=O)—, —$(CH_2)_{1-12}$—(C=O)—NH—, -(phenyl)-$(CH_2)_{1-3}$—(C=O)—NH—, —S—$(CH_2)$—(C=O)—NH-(phenyl)-, —$(CH_2)_{1-12}$—(C=O)—NH—$(CH_2)_{1-12}$—, —$(CH_2)_2$—(C=O)—O—$(CH_2)_2$—O—(C=O)—$(CH_2)_2$—(C=O)—NH—, —($C_{1-6}$ alkyl)-(C=O)—N—($C_{1-6}$ alkyl)-, acetal, ketal, acyloxyalkyl ether, —N=CH—, —($C_{1-6}$ alkyl)-S—S—($C_{0-6}$alkyl)-, —($C_{1-6}$alkyl)-S—S—($C_{1-6}$alkyl)-(C=O)—O—, —($C_{1-6}$ alkyl)-S—S—($C_{1-6}$ alkyl)-(C=O)—NH—, —S—S—$(CH_2)_{1-3}$—(C=O)—NH—$(CH_2)_{1-4}$—NH—(C=O)—$(CH_2)_{1-3}$—, —S—S—($C_{0-3}$ alkyl)-(phenyl)-, —S—S—($C_{1-3}$-alkyl)-(phenyl)-(C=O)—NH—$(CH_2)_{1-5}$—, —($C_{1-3}$ alkyl)-(phenyl)-(C=O)—NH—$(CH_2)_{1-5}$—(C=O)—NH—, —S—S—($C_{1-3}$-alkyl)-, —($C_{1-3}$-alkyl)-(phenyl)-(C=O)—NH—, —O—($C_1$-$C_6$ alkyl)-S($O_2$)—($C_{1-6}$ alkyl)-O—(C=O)—NH—, —S—S—(CH$_2$)$_{1-3}$—(C=O)—, —(CH$_2$)$_{1-3}$—(C=O)—NH—N=C—S—S—(CH$_2$)$_{1-3}$—(C=O)—NH—(CH$_2$)$_{1-5}$—, —(CH$_2$)$_{1-3}$—(C=O)—NH—(CH$_2$)$_{1-5}$—(C=O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

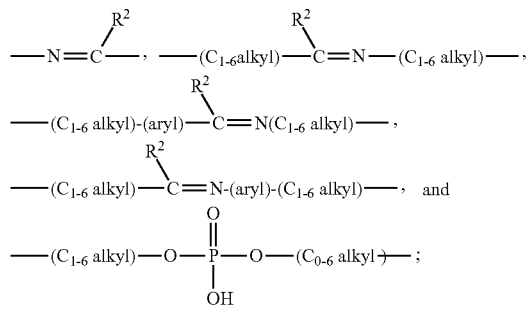

n is 0 or 1, wherein when n is 0, Sp$^1$ is a bond;

m is an integer ranging from 2 to 2,000;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

A is a biologically active agent;

Z is selected from the group consisting of: phosphate, phosphate ester, —(C=O)O—, carboxylic acid ester, thioester, amide, disulfide, amine, —NH(R$^1$)—, amidine, hydrazone, —N=CH—, —NH—CH$_2$—,

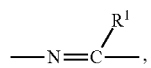

—N=C—, —NH—C(R$^1$)H—, —S—CH$_2$—C(OH)(R$^2$)—, —O—CH$_2$—C(OH)(R$^2$)—, —C(=O)O—CH$_2$—C(OH)(R$^2$)—, —NR$^2$—CH$_2$—C(OH)(R$^2$)—, —S—CH$_2$—C(SH)(R$^2$)—, —O—CH$_2$—C(SH)(R$^2$)—, —C(=O)O—CH$_2$—C(SH)(R$^2$)—, —NR$^2$—CH$_2$—C(SH)(R$^2$)—,

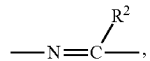

—C(R$^2$)H—NH—, —(C=O)—NH—(C=O)—NH—,

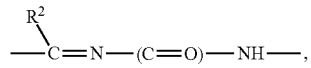

—C(R$^2$)H—NH—(C=O)—NH—, —(C=O)—NH—(C=S)—O—,

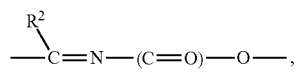

—C(R$^2$)H—NH—(C=O)—O—, —(C=O)—NH—(C=S)—NH—,

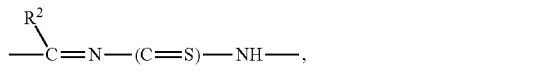

—C(R$^2$)H—NH—(C=S)—NH—, —(C=O)—NH—(C=S)—O—,

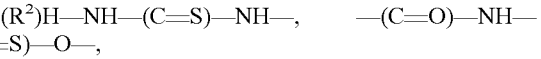

—C(R$^2$)H—NH—(C=S)—O—,

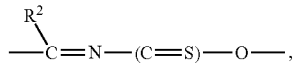

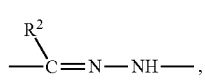

—NH—(C=O)—NH—, —O—(C=O)—NH—, —NH—(C=S)—NH—, —O—(C=S)—NH—, —S—CH$_2$CH$_2$—(C=O)—, —S—CH$_2$CH(CH$_3$)—(C=O)—, —S—CH$_2$CH$_2$—(C=O)O—, —S—CH$_2$CH(CH$_3$)—(C=O)O—, —S—CH$_2$CH$_2$—(C=O)NH—, —S—CH$_2$CH$_2$-(pyridyl)-, —S—CH$_2$—CH$_2$—SO$_2$—, —S—CH$_2$—CH$_2$—SO$_2$—, —S—CH$_2$—(C=O)—O—, —S—CH$_2$—(C=O)—NH—, —S—CH$_2$—(C=O)—, and

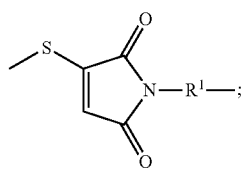

R$^1$ is C$_{1-6}$ alkyl, C$_{3-6}$ cycloalkyl, or an aryl group having 5-8 endocyclic atoms;

R$^2$ is H, C$_{1-6}$ alkyl, C$_{3-6}$ cycloalkyl, or an aryl group having 5-8 endocyclic atoms;

and with respect to compounds of formula (Ib),

K is a group of the formula

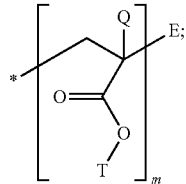

a is an integer ranging from 1-8;

b is an integer ranging from 1-8;

* indicates the point of attachment of each K group to said L.

Within any of the embodiments herein, the biologically active agent, A, may include a spacer group, (Sp$^2$)$_p$, as a means of linking the active agent A to Z, where Sp$^2$ is selected from the group consisting of: —C$_{1-12}$ alkyl-, —C$_{3-12}$ cycloalkyl-, —(C$_{1-8}$ alkyl)-(C$_{3-12}$ cycloalkyl)-(C$_{0-8}$ alkyl)-, —(CH$_2$)$_{1-12}$O—, (—(CH$_2$)$_{1-6}$—O—(CH$_2$)$_{1-6}$—)$_{1-12}$, (—(CH$_2$)$_{1-4}$—NH—(CH$_2$)$_{1-4}$)$_{1-12}$, (—(CH$_2$)$_{1-4}$—O—(CH$_2$)$_{1-4}$)$_{1-12}$O—(CH$_2$)$_{1-12}$—, (—(CH$_2$)$_{1-4}$—O—(CH$_2$)$_{1-4}$)$_{1-12}$O—(CH$_2$)$_{1-12}$—, —(CH$_2$)$_{1-12}$—(C=O)—O—, —(CH$_2$)$_{1-12}$—O—(C=O)—, -(phenyl)-(CH$_2$)$_{1-3}$—(C=O)—O—, -(phenyl)-(CH$_2$)$_{1-3}$—(C=O)—NH—, —(C$_{1-6}$ alkyl)-(C=O)—O—(C$_{0-6}$ alkyl)-, —(CH$_2$)$_{1-12}$—(C=O)—O—(CH$_2$)$_{1-12}$—, —CH(OH)—CH(OH)—(C=O)—O— —CH(OH)—CH(OH)—(C=O)—NH—, —S-maleimido-(CH$_2$)$_{1-6}$—, —S-maleimido-(C$_{1-3}$ alkyl)-(C=O)—NH—, —S-maleimido-(C$_{1-3}$ alkyl)-(C$_{5-6}$ cycloalkyl)-(C$_{0-3}$ alkyl)-, —(C$_{1-3}$ alkyl)-(C$_{5-6}$ cycloalkyl)-(C$_{0-3}$ alkyl)-(C=O)—O—, —(C$_{1-3}$ alkyl)-(C$_{5-6}$ cycloalkyl)-(C$_{0-3}$ alkyl)-(C=O)—NH—, —S-maleimido-(C$_{0-3}$alkyl)-phenyl-(C$_{0-3}$alkyl)-, —(C$_{0-3}$ alkyl)-phenyl-(C=O)—NH—, —(CH$_2$)$_{1-12}$—NH—(C=O)—, —(CH$_2$)$_{1-12}$—(C=O)—NH—, -(phenyl)-(CH$_2$)$_{1-3}$—(C=O)—NH—, —S—(CH$_2$)—(C=O)—NH-(phenyl)-, —(CH$_2$)$_{1-12}$—(C=O)—NH—(CH$_2$)$_{1-12}$—, —(CH$_2$)$_2$—(C=O)—O—(CH$_2$)$_2$—O—(C=O)—(CH$_2$)$_2$—(C=O)—NH—, —(C$_{1-6}$ alkyl)-(C=O)—N—(C$_{1-6}$ alkyl)-, acetal, ketal, acyloxyalkyl ether, —N=CH—, —(C$_{1-6}$ alkyl)-S—S—(C$_{0-6}$ alkyl)-, —(C$_{1-6}$ alkyl)-S—S—(C$_{1-6}$ alkyl)-(C=O)—O—, —(C$_{1-6}$ alkyl)-S—S—(C$_{1-6}$ alkyl)-(C=O)—NH—, —S—S—(CH$_2$)$_{1-3}$—(C=O)—NH—(CH$_2$)$_{1-4}$—NH—(C=O)—(CH$_2$)$_{1-3}$—, —S—S—(C$_{0-3}$ alkyl)-(phenyl)-, —S—S—(C$_{1-3}$-alkyl)-(phenyl)-(C=O)—NH—(CH$_2$)$_{1-5}$—, —(C$_{1-3}$ alkyl)-(phenyl)-(C=O)—NH—(CH$_2$)$_{1-5}$—(C=O)—NH—, —S—S—(C$_{1-3}$-alkyl)-, —(C$_{1-3}$-alkyl)-(phenyl)-(C=O)—NH—, —O—(C$_1$-C$_6$ alkyl)-S(O$_2$)—(C$_{1-6}$ alkyl)-O—(C=O)—NH—, —S—S—(CH$_2$)$_{1-3}$—(C=O)—, —(CH$_2$)$_{1-3}$—(C=O)—NH—N=C—S—S—(CH$_2$)$_{1-3}$—(C=O)—NH—(CH$_2$)$_{1-5}$—, (CH$_2$)$_{1-3}$—(C=O)—NH—(CH$_2$)$_{1-5}$—(C=O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

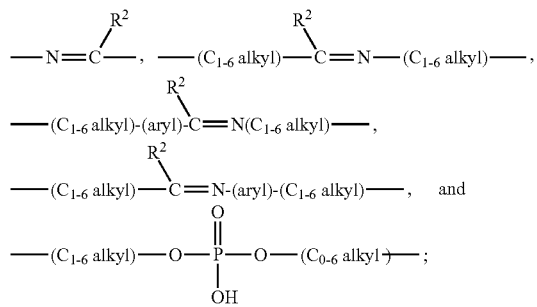

and
wherein when p is 0, the spacer group Sp$^2$ is not present and -Sp$^2$- denotes a covalent bond such that the biologically active agent "A" is linked directly to the Z group by one or more covalent bonds.

Within any of the embodiments herein, the polymeric portion of the compounds is poly-hydroxyethylmethacryloyl phosphorylcholine (poly-HEMA-PC). In a related embodiment, the polymer is prepared from a mixture of monomers, at least half of which are hydroxyethylmethacryloyl phosphorylcholine (i.e., HEMA-PC).

Within any of the embodiments herein, m is an integer that may be selected from the following ranges: 2-30, 30-100, 100-500, 500-1,000 and 1,000-2,000.

Within any of the embodiments herein, X is a group selected from hydroxyl, thiol, disulfide, dithiopyridyl, aldehyde, aldehyde hydrate, ketone, thione, acetal, ketal, —CH$(OR^1)_2$, hemiacetal, hemiketal, monothioketal, dithiohemiketal, dithioketal, epoxide, thioepoxide, glyoxal, diones, amide, hydrazide, carboxyl, carboxylic acid ester, orthoester, N-hydroxysuccinimide ester, succinimidyl, maleimidyl, 1-benzotriazolyl, —$CO_2$-succinimidyl, —$CO_2$-maleimidyl, imidoester, guanido, and —$CO_2$-(1-benzotriazolyl); where $R^1$ is $C_{1-6}$ alkyl, $C_{3-6}$ cycloalkyl, or an aryl group having 5-8 endocyclic atoms.

Within any of the embodiments herein, X is a group selected from amine, urea, carbamate, carbonate, thiourea, thiocarbamate, isocyanate, isothiocyanate, sulfone, chloroethylsulfone, —O(C═O)—$CH_2$—I, —O(C═O)—$CH_2$—Br, —NH(C═O)—$CH_2$—I, —NH(C═O)—$CH_2$—Br, —(C═O)—$CH_2$—I, and —(C═O)—$CH_2$—Br.

Within any of the embodiments herein, X is a group selected from alpha-beta substituted carbonyl, alpha-beta substituted carboxyl, acryloyl, acrylate, methacrylate, acrylamide, vinylsulfone, and vinylpyridine.

Within any of the embodiments herein, n is 1.

Within any of the embodiments herein, n is 0 and $-(Sp^1)_0-$ is a covalent bond.

Within any of the embodiments herein, either: a=2, and b=3 or 4; or a=3 or 4, and b=2.

Within any of the embodiments herein, said biologically active agent is selected from the group consisting of: drugs, vaccines, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA snRNA, RNAi, DNA, cDNA, antisense constructs, ribozymes, etc).

Within any of the embodiments herein, wherein said biologically active agent is selected from the group consisting of: agalsidase, alefacept, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO) (i.e., 166 amino acid form and mature 165 amino acid form of human EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, desmopressin, exendin-4, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab, visilizumab, and fragments and mimetics thereof.

Within any of the embodiments herein, said biologically active agent is selected from the group consisting of: erythropoietin, granulocyte colony stimulating factor (G-CSF), interferon alpha, interferon beta, human growth hormone, and imiglucerase.

Within any of the embodiments herein, said biologically active agent is selected from the group consisting of: tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines.

Within any of the embodiments herein, said biologically active agent is selected from the group consisting of: aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Within any of the embodiments herein, said biologically active agent is a protein or polypeptide.

Within any of the embodiments herein, said protein or polypeptide comprises a non-naturally occurring amino acid.

Another group of embodiments is directed to a method of preparing a compound of formulas (Ia) through (Vb) according to any of the above embodiments, Another group of embodiments is directed to a pharmaceutical composition comprising a compound of formulas (Ib), (IIb), (IIIb) (IVb) or (Vb) according to any of the above embodiments.

Another group of embodiments is directed to a pharmaceutical composition further comprising a second biologically active agent.

Another group of embodiments is directed to a method of treatment compromising administering to a patient in need thereof a compound of formulas (Ib), (IIb), (IIIb) (IVb) or (Vb) according to any of the above embodiments.

The invention provides for compounds or compositions (e.g., pharmaceutical compositions) that include a biologically active agent bonded (e.g., covalently bonded) to a phosphorylcholine containing polymer. The invention also contemplates a single phosphorylcholine bonded to a biologically active agent. In one embodiment, the phosphorylcholine is an oxyethylphosphorylcholine, for example, an acryloyloxyethylphosphorylcholine.

The invention includes methods of treating a human or animal patient which include administering to a patient in need thereof a phosphorylcholine containing polymer of the invention bonded to a biologically active agent or administering to a patient in need thereof a pharmaceutical composition containing a phosphorylcholoine containing polymer bonded to a biologically active agent.

The invention provides for methods of increasing the half-life of a biologically active agent in a patient which include bonding a phosphorylcholine (e.g., phosphorylcholine containing polymer) to a biologically active agent in accordance with the invention.

The phosphorylcholine containing polymer may be any useful type of polymer. For example, and without limitation, the phosphorylcholine containing polymer may be a linear polymer and the phosphorylcholine containing polymer may be a branched polymer, each as is understood by a practitioner of skill in the art.

The polymers of the invention (i.e., phosphorylcholoine containing polymers) may be of any useful size. In one embodiment, the polymers are greater than 0.5 kDa in size, for example, greater than 4 kDa in size. In one embodiment, the phosphorylcholine polymer has a molecular weight between about 0.5 kDa and about 800 kDa, for example, between about 0.5 kDa and about 400 kDa (e.g., between about 0.5 kDa and about 200 kDa). Polymers of the invention are contemplated which contain as few as two phosphorylcholine groups. For example, polymers of the invention are contemplated which contain two, three, four, five, six, seven and eight or more phosphorylcholine groups.

Many biologically active agents are disclosed in the present application and, accordingly, the invention encompasses each of the biologically active agents disclosed herein bonded to the phosphorylcholoine containing polymers of the invention. The biologically active agents are typically bonded to the phosphorylcholoine containing polymers of the invention by a covalent bond. Any useful covalent bonding may be employed in the invention. For example, and without limitation, the biologically active agents may be bonded to the phosphorylcholoine containing polymers through a covalent bond at least one of an amino group, a hydroxyl group, a sulfhydryl group and a carboxyl group of the biologically active agent.

In one embodiment, the phosphorylcholine polymer is covalently bonded to a spacer and the biologically active agent is covalently bonded to the spacer. That is, in certain instances it may be useful to attach a biologically active agent to the phosphorylcholoine containing polymers of the invention using a spacer such as (Steve, may want to mention a few linker types here). For example, covalently bonding a phosphorylcholoine containing polymer to a biologically active agent by use of a spacer may reduce steric hindrance which prevents or reduces the efficiency of the bonding (i.e., the chemical bonding reaction) that provides for the coupling of the phosphorylcholine containing polymer to the biologically active agent.

In one useful embodiment, the biologically active agent is a protein, i.e., a therapeutic protein. In one embodiment, the biologically active agent is a human protein such as a human cytokine.

The biologically active agents of the invention may be obtained from any useful source and by any useful methodology. For example, the biologically active agents of the invention, such as human proteins (e.g., human cytokines such as erythropoietin, G-CSF, interferons, GM-CSF and human enzymes and human hormones) and antibodies, may be obtained by heterologous gene expression in bacteria, yeast and cell cultures such as mammalian cell cultures, insect cell cultures, plant cell cultures and avian cell cultures as is understood in the art. The proteins of the invention, such as human proteins (e.g., human cytokines such as erythropoietin, G-CSF, interferons, GM-CSF and human enzymes and human hormones) and antibodies, may also be obtained from transgenic organisms such as transgenic avians (e.g., transgenic chickens, transgenic quail and transgenic turkey), transgenic goats, transgenic cows and transgenic plants as is understood in the art. It is also contemplated that human proteins for use as disclosed herein can be produced by gene activation in human cell lines as is understood in the art. Many of the biologically active agents can be obtained from natural sources or can be obtained from organic synthesis reactions as is understood in the art.

BRIEF DESCRIPTION OF THE DRAWINGS

FIG. 1 shows the amino acid sequence (165 amino acids) of human erythropoietin (EPO).

FIG. 2 shows the amino acid sequence (174 amino acids) of human granulocyte colony stimulating factor (G-CSF).

DETAILED DESCRIPTION OF THE INVENTION

A. Introduction

Figure 3:
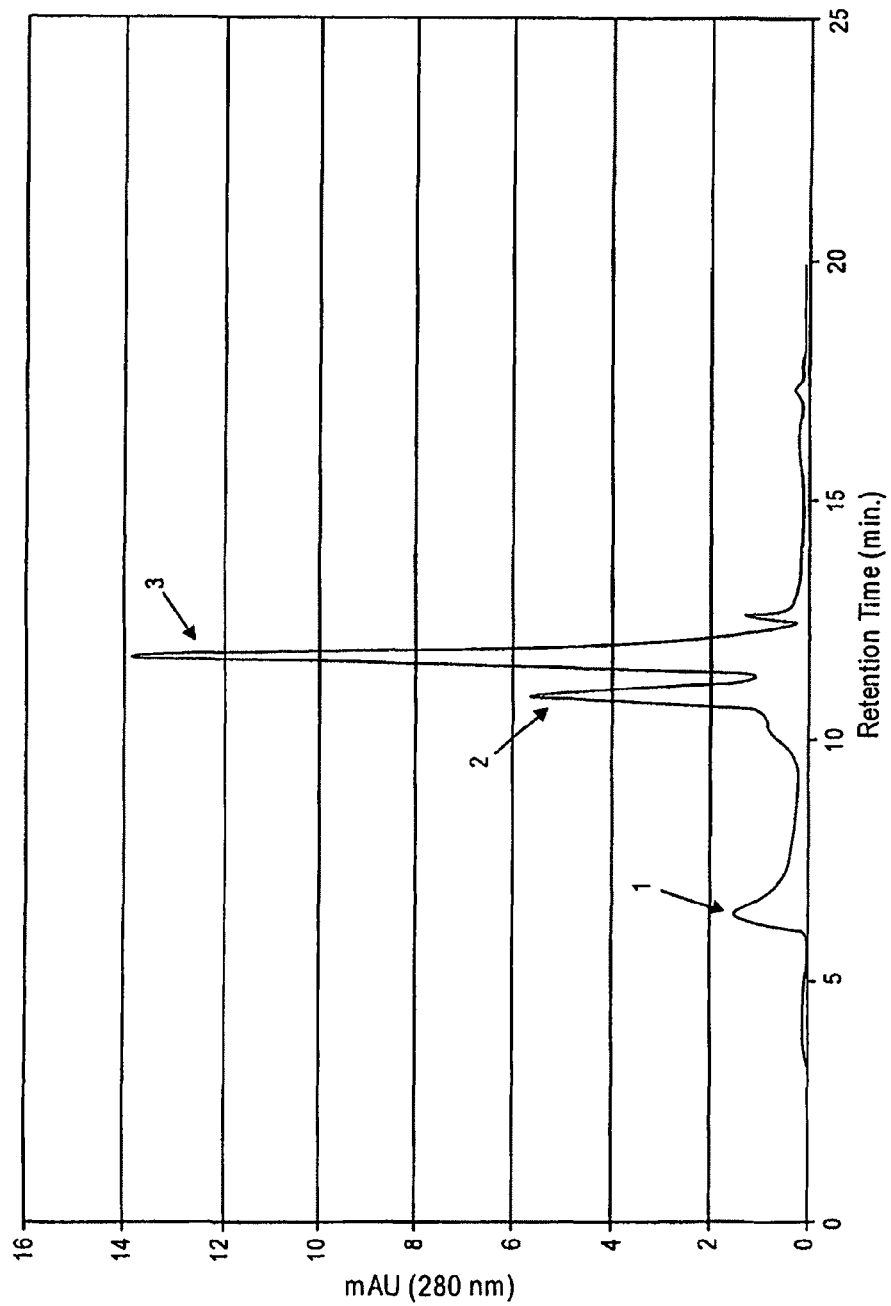
FIGS. 3 and 4 show an HPLC chromatogram illustrating the conjugation of an aldehyde functionalized polymer of the invention to G-CSF.

For the purpose of the present invention the following terminology will be used in accordance with the definitions set forth below.

"Water-soluble polymer" refers to a polymer that is soluble in water at room temperature. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

Molecular weight in the context of the polymer can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.5, as judged by gel permeation chromatography. In other embodiments the polydispersities may be in the range of about 1.4 to about 1.2, more preferably less than about 1.15, still more preferably less than about 1.10, yet still more preferably less than about 1.05, and most preferably less than about 1.03.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "about" as used herein means variation one might see in measurements taken among different instruments, samples, and sample preparations.

The term "compound" as used herein is intended to encompass not only the specified molecular entity but also its pharmaceutically acceptable, pharmacologically active derivatives, including, but not limited to, salts, prodrug conjugates such as esters and amides, metabolites, hydrates, solvates and the like.

The terms "protected,", "protected form", "protecting group" and "protective group" refer to the presence of a group (i.e., the protecting group) that prevents or blocks reaction of a particular chemically reactive functional group in a molecule under certain reaction conditions. Protecting group will vary depending upon the type of chemically reactive group being protected as well as the reaction conditions to be employed and the presence of additional reactive or protecting groups in the molecule, if any. The skilled artisan will recognize protecting groups known in the art, such as those found in the treatise by Greene et al., "Protective Groups In Organic Synthesis," 3$^{rd}$ Edition, John Wiley and Sons, Inc., New York, 1999.

The terms "spacer," and "spacer group" are used interchangeably herein to refer to an atom or a collection of atoms optionally used to link interconnecting moieties such as a terminus of a water-soluble polymer and a reactive group of a biologically active agent and a reactive group. A spacer may be hydrolytically stable or may include a hydrolytically susceptible or enzymatically degradable linkage.

"Alkyl" refers to linear or branched hydrocarbon chains. Non-limiting examples of alkyl groups include methyl, ethyl, propyl, butyl, pentyl, 1-methylbutyl (i.e., 2-pentyl), 1-ethylpropyl (i.e., 3-pentyl), 3-methylpentyl, and the like. The term "alkyl" is also used to indicate a hydrocarbon group that may be linear or branched that may have two or more functionalities appended; and it is understood that "alkyl" includes alkylene when two functionalities are appended. As used herein, "alkyl" does not include cycloakyl unless expressly stated otherwise. Where alkyl groups may have a range of sizes that size range may be indicated by indicating the number of carbon atoms present in the alkyl group (e.g., $C_{1-3}$ alkyl or $C_1$ to $C_3$ for a one to three carbon atom containing alkyl group). In addition, where a range includes the value of "0" (e.g. $C_{0-3}$ alkyl) the group is not present in one embodiment, and if intervening between two groups, it constitutes a covalent bond.

The term "alkoxy" refers to the above alkyl groups linked, to oxygen.

"Poly(acryloyloxyethyl phosphorylcholine) containing polymer" denotes a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

The term "carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

Terms such as "haloalkyl," and "haloalkoxy" are meant to include monohaloalkyl(oxy) and polyhaloalkyl(oxy). For example, the term "$C_1$-$C_6$ haloalkyl" is mean to include trifluoromethyl, 2,2,2-trifluoroethyl, 4-chlorobutyl, 3-bromopropyl, and the like.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory response. Cytokines are typically small, water-soluble glycoproteins that have a mass of about 8-35 kDa.

"Therapeutic proteins" are peptides or proteins that include an amino acid sequence which in whole or in part makes up a drug and can be used in human or animal pharmaceutical applications. Numerous therapeutic proteins are known to practitioners of skill in the art including, without limitation, those disclosed herein.

"Phosphorylcholine containing polymer" is a polymer that contains phosphorylcholine. It is specifically contemplated that in each instance where a phosphorylcholine containing polymer is specified in this application for a particular use, a single phosphorylcholine can also be employed in such use.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

The term "endocyclic" refers to an atom or group of atoms which comprise part of a cyclic ring structure.

The term "exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to an unsaturated linear or branched hydrocarbon group containing at least one carbon-carbon double bond. Non-limiting examples of alkenyl groups include ethenyl, n-propenyl, isopropenyl, n-butenyl, isobutenyl, octenyl, decenyl, tetradecenyl, and the like.

"Aryl" refers to a cyclic aromatic group having one or more aromatic rings, each having 5 or 6 endocyclic atoms independently selected from carbon, oxygen, nitrogen and sulfur. Aryl rings may be fused. Non-limiting examples of aryl groups include naphthyl, and phenyl. As used herein, "aryl" includes carbocyclic aryl, in which all endocyclic atoms of the aromatic group are carbon atoms, and heteroaryl groups.

"Heteroaryl" refers to an aryl group having one or more heteroatoms (for example nitrogen, oxygen and/or sulfur) in at least one ring. Non-limiting examples include pyrrole, furanyl, thienyl, pyridyl, oxazolyl, thiazolyl, benzofuranyl, and benzothienyl.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Phosphorylcholine," also denoted as "PC," refers to

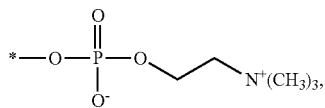

where * denotes the point of attachment. The phosphorylcholine is a zwitterionic group and includes salts (such as inner salts), and protonated and deprotonated forms thereof.

"Reactive group" refers to a functional group that is capable of forming a covalent linkage consisting of one or more bonds to a biologically active agent. Nonlimiting examples include those illustrated in Table 1.

"Maleimido" refers to a pyrrole-2,5-dione-1-yl group having the structure

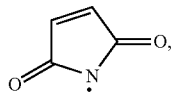

which upon reaction with a sulfhydryl (e.g., a thio alkyl) forms an —S-maleimido group having the structure

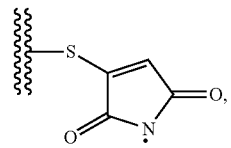

where "•" indicates the point of attachment for the maleimido group and ⚡ indicates the point of attachment of the sulfur atom the thiol to the remainder of the original sulfhydryl bearing group.

A "hydrolytically susceptible linkage" or "hydrolytically susceptible bond" refers to a chemical linkage or bond, which may be a covalent bond that undergoes hydrolysis under physiological conditions. The tendency of a bond to hydrolyze may depend not only on the general type of linkage connecting two central atoms between which the bond is severed, but also on the substituents attached to these central atoms. Non-limiting examples of hydrolytically susceptible linkages include esters of carboxylic acids, phosphate esters, acetals, ketals, acyloxyalkyl ether, imines, orthoesters, and some amide linkages.

An "enzymatically degradable linkage" means a linkage that is subject to degradation by one or more enzymes. Some hydrolytically susceptible linkages may also be enzymatically degradable. For example esterases may act on esters of carboxylic acid or phosphate esters, and proteases may act on peptide bonds and some amide linkages.

The terms "active agent" and "biologically active agent" are used interchangeably herein and are defined to include any agent, drug, compound, or mixture thereof that provides some local or systemic physiological or pharmacologic effect that can be demonstrated in vivo or in vitro. Non-limiting examples include drugs, vaccines, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA snRNA, RNAi, DNA, cDNA, antisense constructs, ribozymes, etc).

The term "solvate" as used herein means a compound of the invention or a salt, thereof, that further includes a stoichiometric or non-stoichiometric amount of a solvent bound by non-covalent intermolecular forces in an amount of greater than about 0.3% when prepared according to the invention.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

For the purpose of this disclosure, "isomers" refer to certain compounds of the present invention which possess asymmetric carbon atoms (optical centers) or double bonds; the racemates, diastereomers, geometric isomers and individual isomers (e.g., separate enantiomers). All of these are encompassed by the term "isomers" within the scope of the present invention.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer single monomer derived backbone.

"Branched," in reference to the geometry, architecture or overall structure of a polymer, refers to polymer having 2 or more polymer "arms" extending from a single group, such as an L group that may be derived from an initiator employed in an atom transfer radical polymerization reaction. A branched polymer may possess 2 polymer arms, 3 polymer arms, 4 polymer arms, 5 polymer arms, 6 polymer arms, 8 polymer arms or more. For the purpose of this disclosure, compounds having three or more polymer arms extending from a single linear group are denoted as having a "comb" structure or "comb" architecture.

"Forked," refers to a multifunctional chemical structure wherein multiple functional groups (reactive groups or biologically active agents) in addition to one or more polymer arms are attached (either directly or through one or more atoms) to a chemical group such as an L group that may be derived from an initiator employed in an atom transfer radical polymerization reaction.

"Pharmaceutically acceptable" composition or "pharmaceutical composition" refers to a composition comprising a compound of the invention and a pharmaceutically acceptable excipient or pharmaceutically acceptable excipients.

The term "salt" includes, without limitation, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; salts of alkali metal cations such as $Na^+$, $K^+$, $Li^+$ (e.g., NaCl, KCl) organic amine salts or alkali earth metal salts such as Mg or Ca salts.

"Pharmaceutically acceptable excipient" and "pharmaceutically acceptable carrier" refer to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose and the like.

"Patient" or "subject in need thereof" refers to a living organism suffering from or prone to a condition that can be prevented or treated by administration of a pharmaceutical composition as provided herein. Non-limiting examples include humans, other mammals and other non-mammalian animals.

"Therapeutically effective amount" refers to an amount of a conjugated biologically active agent or of a pharmaceutical composition useful for treating, ameliorating, or preventing an identified disease or condition, or for exhibiting a detectable therapeutic or inhibitory effect. The effect can be detected by any assay method known in the art.

The "biological half-life" of a substance is a pharmacokinetic parameter which specifies the time required for one half of the substance to be removed from an organism following introduction of the substance into the organism.

B. Compounds of the Invention

One aspect of the present invention relates to compounds of formula (Ia):

$(X-(Sp^1)_n)_a-L-(K)_b$ (Ia)

where
K is a group of the formula

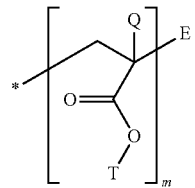

each occurrence of Q is independently selected from the group consisting of H and $C_{1-4}$ alkyl;
each occurrence of T is independently selected from the group consisting of H, —$C_{1-4}$ alkyl, and —$C_{1-4}$ alkyl—O—PC, where PC denotes a phosphorylcholine group, with the proviso that one or more T groups is —$C_{1-4}$ alkyl—O—PC;
each occurrence of E is independently selected from the group consisting of halo and Nu wherein Nu represents a nucleophilic group;
$Sp^1$ is a spacer group;
X is a reactive group or a protected form thereof;
n is 0 or 1, wherein when n is 0, $Sp^1$ is a bond;
m is an integer ranging from 2 to 2,000;
a is an integer ranging from 1-8;
b is an integer ranging from 1-8;
L is selected from the group consisting of $C_{1-4}$alkyl, cycloalkyl, carboxy$C_{1-4}$alkyl, carboxycycloalkyl, $C_{1-4}$alkoxy$C_{1-4}$alkyl and cyclic alkyl ether; and
* indicates the point of attachment of each K group to said L.

In one embodiment of compounds of formula (Ia) K is a group of the formula

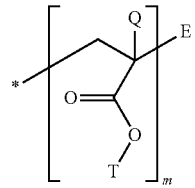

each occurrence of Q is independently selected from the group consisting of H, methyl, and ethyl;
each occurrence of T is independently selected from the group consisting of H, —$CH_3$, —$CH_2$—$CH_3$, and —$CH_2$—$CH_2$—O—PC, where PC denotes a phosphorylcholine group, with the proviso that one or more T groups is —$CH_2$—$CH_2$—O—PC;
each occurrence of E is independently selected from the group consisting of Br, Cl, I, —$NH_2$, —NH($C_{1-4}$ alkyl), —N($C_{1-4}$ alkyl)$_2$, —OH, —O—($C_{1-4}$ alkyl), and —O—($C_{1-4}$haloalkyl);

Sp$^1$ is selected from the group consisting of: —C$_{1-12}$ alkyl-, —C$_{3-12}$ cycloalkyl-, —(C$_{1-8}$ alkyl)-(C$_{3-12}$ cycloalkyl)-(C$_{0-8}$alkyl)-, —(CH$_2$)$_{1-12}$O—, (—(CH$_2$)$_{1-6}$—O—(CH$_2$)$_{1-6}$)$_{1-12}$—, (—(CH$_2$)$_{1-4}$—NH—(CH$_2$)$_{1-4}$)$_{1-12}$—, (—(CH$_2$)$_{1-4}$—O—(CH$_2$)$_{1-4}$)$_{1-12}$—O—, (—(CH$_2$)$_{1-4}$—O—(CH$_2$)$_{1-4}$—)$_{1-12}$O—(CH$_2$)$_{1-12}$—, —(CH$_2$)$_{1-12}$(C=O)—O—, —(CH$_2$)$_{1-12}$—O—(C=O)—, -(phenyl)-(CH$_2$)$_{1-3}$—(C=O)—O—, -(phenyl)-(CH$_2$)$_{1-3}$(C=O)—NH—, —(C$_{1-6}$ alkyl)-(C=O)—O—(C$_{0-6}$ alkyl)-, —(CH$_2$)$_{1-12}$—(C=O)—O—(CH$_2$)$_{1-12}$—, —CH(OH)—CH(OH)—(C=O)—O—CH(OH)—CH(OH)—(C=O)—NH—, —S-maleimido-(CH$_2$)$_{1-6}$—, —S-maleimido-(C$_{1-3}$ alkyl)-(C=O)—NH—, —S-maleimido-(C$_{1-3}$ alkyl)-(C$_{5-6}$ cycloalkyl)-(C$_{0-3}$ alkyl)-, —(C$_{1-3}$ alkyl)-(C$_{5-6}$ cycloalkyl)-(C$_{0-3}$ alkyl)-(C=O)—O—, —(C$_{1-3}$ alkyl)-(C$_{5-6}$ cycloalkyl)-(C$_{0-3}$ alkyl)-(C=O)—NH—, —S-maleimido-(C$_{0-3}$alkyl)-phenyl-(C$_{0-3}$alkyl)-, —(C$_{0-3}$ alkyl)-phenyl-(C=O)—NH—, —(CH$_2$)$_{1-12}$—NH—(C=O)—, —(CH$_2$)$_{1-12}$—(C=O)—NH—, -(phenyl)-(CH$_2$)$_{1-3}$—(C=O)—NH—, —S—(CH$_2$)—(C=O)—NH-(phenyl)-, —(CH$_2$)$_{1-12}$—(C=O)—NH—(CH$_2$)$_{1-12}$—, —(CH$_2$)$_2$—(C=O)—O—(CH$_2$)$_2$—O—(C=O)—(CH$_2$)$_2$—(C=O)—NH—, —(C$_{1-6}$ alkyl)-(C=O)—N—(C$_{1-6}$ alkyl)-, acetal, ketal, acyloxyalkyl ether, —N=CH—, —(C$_{1-6}$ alkyl)-S—S—(C$_{0-6}$ alkyl)-, —(C$_{1-6}$ alkyl)-S—S—(C$_{1-6}$ alkyl)-(C=O)—O—, —(C$_{1-6}$ alkyl)-S—S—(C$_{1-6}$ alkyl)-(C=O)—NH—, —S—S—(CH$_2$)$_{1-3}$—(C=O)—NH—(CH$_2$)$_{1-4}$—NH—(C=O)—(CH$_2$)$_{1-3}$—, —S—S—(C$_{0-3}$ alkyl)-(phenyl)-, —S—S—(C$_{1-3}$-alkyl)-(phenyl)-(C=O)—NH—(CH$_2$)$_{1-5}$—, —(C$_{1-3}$ alkyl)-(phenyl)-(C=O)—NH—(CH$_2$)$_{1-5}$—(C=O)—NH—, —S—S—(C$_{1-3}$-alkyl)-, —(C$_{1-3}$-alkyl)-(phenyl)-(C=O)—NH—, —O—(C$_1$-C$_6$ alkyl)-S(O$_2$)—(C$_{1-6}$ alkyl)-O—(C=O)—NH—, —S—S—(CH$_2$)$_{1-3}$—(C=O)—, —(CH$_2$)$_{1-3}$—(C=O)—NH—N=C—S—S—(CH$_2$)$_{1-3}$—(C=O)—NH—(CH$_2$)$_{1-5}$—, —(CH$_2$)$_{1-3}$—(C=O)—NH—(CH$_2$)$_{1-5}$—(C=O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

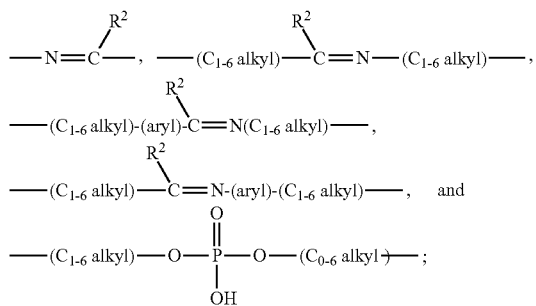

X is selected from the group consisting of: hydroxyl, thiol, disulfide, dithiopyridyl, aldehyde, aldehyde hydrate, ketone, thione, acetal, ketal, —CH(OR$^1$)$_2$, hemiacetal, hemiketal, monothioketal, dithiohemiketal, dithioketal, epoxide, thioepoxide, glyoxal, diones, amide, hydrazide, carboxyl, carboxylic acid ester, orthoester, N-hydroxysuccinimide ester, succinimidyl, maleimidyl, 1-benzotriazolyl, —CO$_2$-succinimidyl, —CO$_2$-maleimidyl, imidoester, guanido, —CO$_2$-(1-benzotriazolyl)amine, urea, carbamate, carbonate, thiourea, thiocarbamate, isocyanate, isothiocyanate, sulfone, chloroethylsulfone, alpha-beta substituted carbonyl, alpha-beta substituted carboxyl, acryloyl, acrylate, methacrylate, acrylamide, vinylsulfone, vinylpyridine, —O(C=O)—CH$_2$—I, —O(C=O)—CH$_2$—Br, —NH(C=O)—CH$_2$—I, —NH(C=O)—CH$_2$—Br, —(C=O)—CH$_2$—I, and —(C=O)—CH$_2$—Br;

n is 0 or 1, wherein when n is 0, Sp$^1$ is a bond;

m is an integer ranging from 2 to 2,000;

a is an integer ranging from 1-8;

b is an integer ranging from 1-8;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

R$^1$ is C$_{1-6}$ alkyl, C$_{3-6}$ cycloalkyl, or an aryl group having 5-8 endocyclic atoms;

R$^2$ is H, C$_{1-6}$ alkyl, C$_{3-6}$ cycloalkyl, or an aryl group having 5-8 endocyclic atoms; and

* indicates the point of attachment of each K group to said L.

Another aspect of the present invention relates to compounds of formula (Ib):

$$(A\text{-}Z\text{-}(Sp^1)_n)_a\text{-}L\text{-}(K)_b \tag{Ib}$$

where

K is a group of the formula

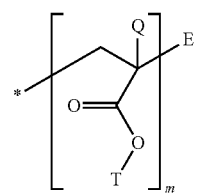

each occurrence of Q is independently selected from the group consisting of H and C$_{1-4}$ alkyl;

each occurrence of T is independently selected from the group consisting of H, —C$_{1-4}$ alkyl, and —C$_{1-4}$ alkyl—O—PC, where PC denotes a phosphorylcholine group, with the proviso that one or more T groups is —C$_{1-4}$ alkyl—O—PC;

each occurrence of E is independently selected from the group consisting of halo and Nu wherein Nu represents a nucleophilic group;

Sp$^1$ is a spacer group;

n is 0 or 1, wherein when n is 0, Sp$^1$ is a bond;

m is an integer ranging from 2 to 2,000;

a is an integer ranging from 1-8;

b is an integer ranging from 1-8;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

A is a biologically active agent;

Z is the product of the reaction between a group present in said biologically active agent and a reactive group bound to said Sp$^1$ group when n is 1, or a reactive group bound to L when n is 0; and

* indicates the point of attachment of each K group to said L.

In one embodiment of compounds of formula (Ib), K is a group of the formula

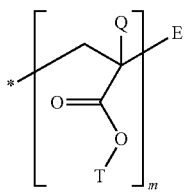

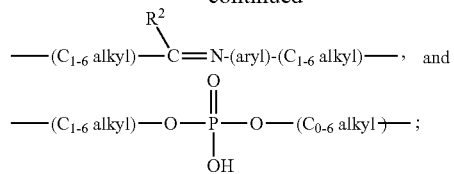

each occurrence of Q is independently selected from the group consisting of H, methyl, and ethyl;

each occurrence of T is independently selected from the group consisting of H, —CH$_3$, —CH$_2$—CH$_3$, and —CH$_2$—CH$_2$—O—PC, where PC denotes a phosphorylcholine group, with the proviso that one or more T groups is —CH$_2$—CH$_2$—O—PC;

each occurrence of E is independently selected from the group consisting of Br, Cl, I, —NH$_2$, —NH(C$_{1-4}$ alkyl), —N(C$_{1-4}$ alkyl)$_2$, —OH, —O—(C$_{1-4}$ alkyl), and —O—(C$_{1-4}$ haloalkyl);

Sp$^1$ is selected from the group consisting of: —C$_{1-12}$ alkyl-, —C$_{3-12}$ cycloalkyl-, —(C$_{1-8}$ alkyl)-(C$_{3-12}$ cycloalkyl)-(C$_{0-8}$ alkyl)-, —(CH$_2$)$_{1-12}$O—, (—(CH$_2$)$_{1-6}$—O—(CH$_2$)$_{1-6}$—)$_{1-12}$—, (—(CH$_2$)$_{1-4}$—NH—(CH$_2$)$_{1-4}$)$_{1-12}$—, (—(CH$_2$)$_{1-4}$—O—(CH$_2$)$_{1-4}$)$_{1-12}$—O—, (—(CH$_2$)$_{1-4}$—O—(CH$_2$)$_{1-4}$—)$_{1-12}$O—(CH$_2$)$_{1-12}$—, —(CH$_2$)$_{1-12}$—(C=O)—O—, —(CH$_2$)$_{1-12}$—O—(C=O)—, -(phenyl)-(CH$_2$)$_{1-3}$—(C=O)—O—, -(phenyl)-(CH$_2$)$_{1-3}$—(C=O)—NH—, —(C$_{1-6}$ alkyl)-(C=O)—O—(C$_{0-6}$ alkyl)-, —(CH$_2$)$_{1-12}$—(C=O)—O—(CH$_2$)$_{1-12}$—, —CH(OH)—CH(OH)—(C=O)—O—CH(OH)—CH(OH)—(C=O)—NH—, —S-maleimido-(CH$_2$)$_{1-6}$—, —S-maleimido-(C$_{1-3}$ alkyl)-(C=O)—NH—, —S-maleimido-(C$_{1-3}$ alkyl)-(C$_{5-6}$ cycloalkyl)-(C$_{0-3}$ alkyl)-, —(C$_{1-3}$ alkyl)-(C$_{5-6}$ cycloalkyl)-(C$_{0-3}$ alkyl)-(C=O)—O—, —(C$_{1-3}$ alkyl)-(C$_{5-6}$ cycloalkyl)-(C$_{0-3}$ alkyl)-(C=O)—NH—, —S-maleimido-(C$_{0-3}$alkyl)-phenyl-(C$_{0-3}$alkyl)-, —(C$_{0-3}$ alkyl)-phenyl-(C=O)—NH—, —(CH$_2$)$_{1-12}$—NH—(C=O)—, —(CH$_2$)$_{1-12}$—(C=O)—NH—, -(phenyl)-(CH$_2$)$_{1-3}$—(C=O)—NH—, —S—(CH$_2$)—(C=O)—NH-(phenyl)-, —(CH$_2$)$_{1-12}$—(C=O)—NH—(CH$_2$)$_{1-12}$—, —(CH$_2$)$_2$—(C=O)—O—(CH$_2$)$_2$—O—(C=O)—(CH$_2$)$_2$—(C=O)—NH—, —(C$_{1-6}$ alkyl)-(C=O)—N—(C$_{1-6}$ alkyl)-, acetal, ketal, acyloxyalkyl ether, —N=CH—, —(C$_{1-6}$ alkyl)-S—S—(C$_{0-6}$ alkyl)-, —(C$_{1-6}$ alkyl)-S—S—(C$_{1-6}$ alkyl)-(C=O)—O—, —(C$_{1-6}$ alkyl)-S—S—(C$_{1-6}$ alkyl)-(C=O)—NH—, —S—S—(CH$_2$)$_{1-3}$—(C=O)—NH—(CH$_2$)$_{1-4}$—NH—(C=O)—(CH$_2$)$_{1-3}$—, —S—S—(C$_{0-3}$ alkyl)-(phenyl)-, —S—S—(C$_{1-3}$-alkyl)-(phenyl)-(C=O)—NH—(CH$_2$)$_{1-5}$—, —(C$_{1-3}$ alkyl)-(phenyl)-(C=O)—NH—(CH$_2$)$_{1-5}$—(C=O)—NH—, —S—S—(C$_{1-3}$-alkyl)-, —(C$_{1-3}$-alkyl)-(phenyl)-(C=O)—NH—, —O—(C$_1$-C$_6$ alkyl)-S(O$_2$)—(C$_{1-6}$ alkyl)-O—(C=O)—NH—, —S—S—(CH$_2$)$_{1-3}$—(C=O)—, —(CH$_2$)$_{1-3}$—(C=O)—NH—N=C—S—S—(CH$_2$)$_{1-3}$—(C=O)—NH—(CH$_2$)$_{1-5}$—, —(CH$_2$)$_{1-3}$—(C=O)—NH—(CH$_2$)$_{1-5}$—(C=O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

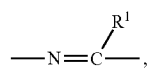

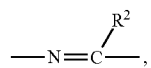

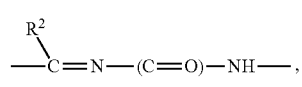

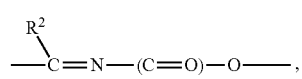

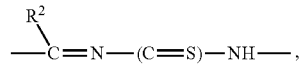

n is 0 or 1, wherein when n is 0, Sp$^1$ is a bond;

m is an integer ranging from 2 to 2,000;

a is an integer ranging from 1-8;

b is an integer ranging from 1-8;

L is selected from the group consisting of C$_{1-4}$alkyl, cycloalkyl, carboxyC$_{1-4}$alkyl, carboxycycloalkyl, C$_{1-4}$alkoxyC$_{1-4}$alkyl and cyclic alkyl ether;

A is a biologically active agent;

Z is selected from the group consisting of: phosphate, phosphate ester, —(C=O)O—, carboxylic acid ester, thioester, amide, dislufide, amine, —NH(R$^1$)—, amidine, hydrazone, —N=CH—, —NH—CH$_2$—,

—N=C(R$^1$)—,

—NH—C(R$^1$)H—, —S—CH$_2$—C(OH)(R$^2$)—, —O—CH$_2$—C(OH)(R$^2$)—, —C(=O)O—CH$_2$—C(OH)(R$^2$)—, —NR$^2$—CH$_2$—C(OH)(R$^2$)—, —S—CH$_2$—C(SH)(R$^2$)—, —O—CH$_2$—C SH(R$^2$)—, —C(=O)O—CH$_2$—C(SH)(R$^2$)—, —NR$^2$—CH$_2$—C(SH)(R$^2$)—,

—N=C(R$^2$)—,

—C(R$^2$)H—NH—, —(C=O)—NH—(C=O)—NH—,

—C(R$^2$)=N—(C=O)—NH—,

—C(R$^2$)H—NH—(C=O)—NH—, —(C=O)—NH—(C=O)—O—,

—C(R$^2$)=N—(C=O)—O—,

—C(R$^2$)H—NH—(C=O)—O—, —(C=O)—NH—(C=S)—NH—,

—C(R$^2$)=N—(C=S)—NH—,

—C(R$^2$)H—NH—(C=S)—NH—, —(C=O)—NH—(C=S)—O—,

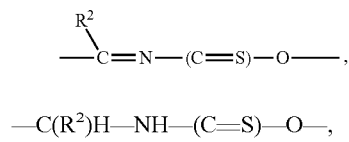

—C(R²)H—NH—(C═S)—O—,

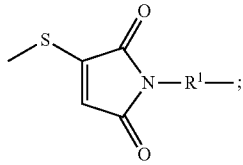

—NH—(C═O)—NH—, —O—(C═O)—NH—, —NH—(C═S)—NH—, —O—(C═S)—NH—, —S—CH₂CH₂—(C═O)—, —S—CH₂CH(CH₃)—(C═O)— —S—CH₂CH₂—(C═O)O—, —S—CH₂CH(CH₃)—(C═O)O—, —S—CH₂CH₂—(C═O)NH—, —S—CH₂—CH₂-(pyridyl)-, —S—CH₂—CH₂—SO₂—, —S—CH₂—CH₂—SO₂—, —S—CH₂—(C═O)—O—, —S—CH₂—(C═O)—NH—, —S—CH₂—(C═O)—, and

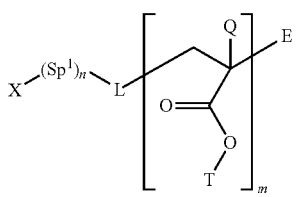

$R^1$ is $C_{1-6}$ alkyl, $C_{3-6}$ cycloalkyl, or an aryl group having 5-8 endocyclic atoms;

$R^2$ is H, $C_{1-6}$ alkyl, $C_{3-6}$ cycloalkyl, or an aryl group having 5-8 endocyclic atoms; and

* indicates the point of attachment of each K group to said L.

B.1 Linear Compounds

One aspect of the present invention is directed to compound of formula (Ia) or formula (Ib) where a and b are both 1 (e.g., or a salt, hydrate, or isomer thereof). Such embodiments include for example compounds of formula (IIa) and compounds of formula (IIb), respectively.

One embodiment of this aspect relates to novel compounds of formula (IIa), or a salt, hydrate, or isomer thereof.

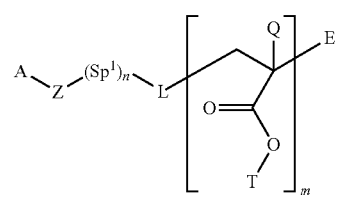

(IIa)

where each occurrence of Q is independently selected from the group consisting of H, methyl, and ethyl;

each occurrence of T is independently selected from the group consisting of H, —CH₃, —CH₂—CH₃, and —CH₂—CH₂—O—PC, where PC denotes a phosphorylcholine group, with the proviso that one or more T groups is —CH₂—CH₂—O—PC;

E is independently selected from the group consisting of Br, Cl, I, —NH₂, —NH($C_{1-4}$ alkyl), —N($C_{1-4}$ alkyl)₂, —OH, —O—($C_{1-4}$ alkyl), and —O—($C_{1-4}$ fluoro-substituted alkyl);

$Sp^1$ is a spacer group;

X is a reactive group or a protected form thereof;

n is 0 or 1, wherein when n is 0, $Sp^1$ is a bond;

m is an integer ranging from 2 to 2,000; and

L is selected from the group consisting of $C_{1-4}$alkyl, cycloalkyl, carboxy$C_{1-4}$alkyl, carboxycycloalkyl, $C_{1-4}$alkoxy$C_{1-4}$alkyl and cyclic alkyl ether.

Another embodiment relates to a zwitterionic compound of formula (IIb) or a salt, hydrate, or isomer thereof:

(IIb)

where each occurrence of Q is independently selected from the group consisting of H, methyl, and ethyl;

each occurrence of T is independently selected from the group consisting of H, —CH₃, —CH₂—CH₃, and —CH₂—CH₂—O—PC, where PC denotes a phosphorylcholine group, with the proviso that one or more T groups is —CH2-CH2-O—PC;

E is independently selected from the group consisting of Br, Cl, I, —NH₂, —NH($C_{1-4}$ alkyl), —N($C_{1-4}$ alkyl)₂, —OH, —O—($C_{1-4}$ alkyl), and —O—($C_{1-4}$-fluoro-substituted alkyl);

$Sp^1$ is a spacer group;

n is 0 or 1, wherein when n is 0, $Sp^1$ is a bond;

m is an integer ranging from 2 to 2,000;

L is selected from the group consisting of $C_{1-4}$alkyl, cycloalkyl, carboxy$C_{1-4}$alkyl, carboxycycloalkyl, $C_{1-4}$alkoxy$C_{1-4}$alkyl and cyclic alkyl ether;

A is a biologically active agent; and

Z is the product of the reaction between a group present in said biologically active agent and a reactive group bound to said $Sp^1$ group when n is 1, or a reactive group bound to L when n is 0.

Unless specified otherwise, all variable groups present in compounds of formulas (IIa) and (IIb) are as defined for compounds of formulas (Ia) and (Ib) and embodiments thereof, respectively.

B.2 Non-Linear Compounds

In addition to linear compounds such as those of formula (IIa) or formula (IIb), described above, the present invention is also directed to compounds having more complex architectures. Such architectures include branched compounds, forked compounds, branched and forked compounds. Branched polymer compounds having multiple polymer arms may also have comb or star architectures. In theory, branched compounds having two or more polymer arms may aid in promoting water solubility without unduly hindering the interactions of an attached biologically active agent.

An aspect of the present invention is directed to forked compounds of formula (Ia) or formula (Ib), where a is an integer greater than 1. In one embodiment, forked compounds of formula (Ia) or formula (Ib), may have a=2 and b=1, for example as in compounds of formula (IIIa) (i.e., (X-($Sp^1$)$_n$)₂-L-(K)₁) or formula (IIIb) (i.e., (A-Z-($Sp^1$)$_n$)₂-L-(K)₁).

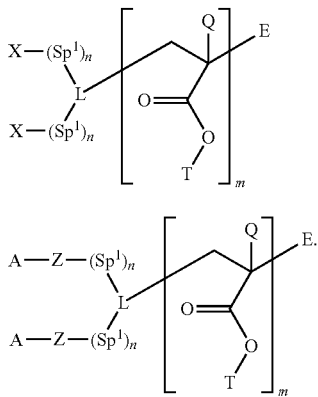

(IIIa)

(IIIb)

In other embodiments, forked compounds of formula (Ia) or formula (Ib), a=3 and b=1; and in other embodiments a=4 and b=1.

In other embodiments of compounds of formula (Ia) or formula (Ib), b is an integer greater than 1 and the compounds are branched compounds having more than one polymer arm in the form of the group K. In some embodiments of branched compounds of formula (Ia) or formula (Ib), a=1 and b=2, as in, for example, compounds of formula (IVa) (i.e., (X-$(Sp^1)_n)_1$-L-$(K)_2$) or formula (IVb) (i.e., (A-Z-$(Sp^1)_n)_1$-L-$(K)_2$).

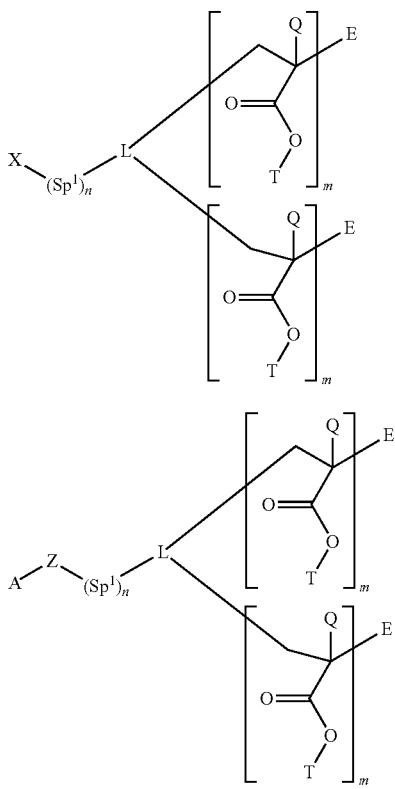

(IVa)

(IVb)

In other embodiments of branched compounds of formula (Ia) or formula (Ib), a=1 and b=3; and in still other embodiment a=1 and b=4. In those embodiments where b is an integer greater than 1, (e.g., b is 2, 3, or 4) the polymeric portion of the molecule may be poly-hydroxyethylmethacryloyl phosphorylcholine, regardless of the value of a (e.g., a may be 1, 2, 3, or 4).

In still other embodiments of compounds of formula (Ia) or formula (Ib), both a and b are integers greater than 1 and the compounds are branched and forked compounds. In one embodiment of branched and forked compounds of formula (Ia) or formula (Ib), a=2 and b=2, for example as in compounds of formula (Va) (i.e., (X-$(Sp^1)_n)_2$-L-$(K)_2$) and compounds of formula (Vb) (i.e., (A-Z-$(Sp^1)_n)_2$-L-$(K)_2$).

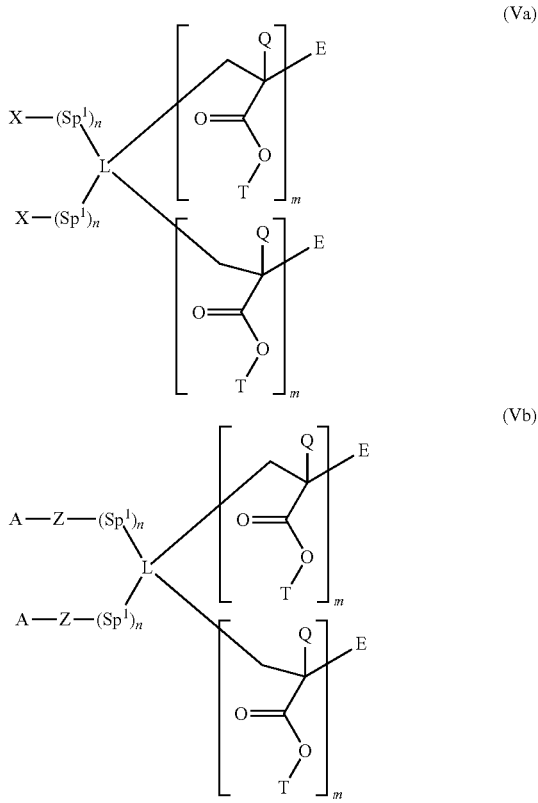

(Va)

(Vb)

In other embodiments of branched and forked compounds of formula (Ia) or formula (Ib), a=2 and b=3 or 4. In still other embodiments of branched and forked compounds of formula (Ia) or formula (Ib), a=3 or 4 and b=2.

In some embodiments of branched, forked, or branched and forked compounds where the sum of a and b is 3; L comprises one carbon atom; or in another embodiment 2 carbon atoms, or in another embodiment L comprises 3 or more carbon atoms. In other embodiments of branched, forked, or branched and forked compounds where the sum of a and b is 4; L comprises 2 carbon atoms, or in another embodiment 3 carbon atoms, or in another embodiment 4 carbon atoms. In still other embodiments of branched, forked, or branched and forked compounds where the sum of a and b is 5; L comprises 3 carbon atoms, or in another embodiment 4 carbon atoms, or in another embodiment 5 carbon atoms. In yet other embodiments of branched, forked, or branched and forked compounds where the sum of a and b is 6; L comprises 4 carbon atoms, or in another embodiment 5 carbon atoms, or in another embodiment 6 carbon atoms.

Unless specified otherwise, all variable groups present in compounds of formulas (IIIa), (IVa) or (Va) are as defined for compounds of formula (Ia) or embodiments thereof. Similarly, unless specified otherwise, all groups present in compounds of formulas (IIIb), (IVb) or (Vb) are as defined for compounds of formula (Ib) or embodiments thereof.

B.3 Compounds of Formulas (Ia) Through (Vb)

In some embodiments of compounds of formulas (Ia) through (Vb) (i.e., compounds (Ia), (Ib), (IIa), (IIb), (IIIa), (IIIb), (IVa), (IVb), (Va), or (Vb)) the polymeric portion of the compounds comprises poly(2-methacryloyloxyethyl phosphorylcholine) also referred to as pMPC, poly-hydroxyethylmethacryloyl phosphorylcholine, pHEMA-PC or poly-HEMA-PC. In other embodiments of compounds of formulas (Ia) through (Vb), the polymeric portion of the molecule consists of a poly-HEMA-PC polymer, e.g., K is a group of the formula

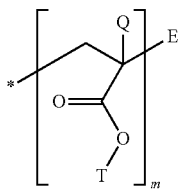

where Q is methyl; T is a phosphorylcholine group; E is independently selected from the group consisting of Br, Cl, I, —$NH_2$, —$NH(C_{1-4}$ alkyl), —$N(C_{1-4}$ alkyl)$_2$, —OH, —O—($C_{1-4}$ alkyl), and —O—($C_{1-4}$ fluoro-substituted alkyl); and m is an integer selected based on the desired molecular weight of the polymeric portion of a compound of formulas (Ia) through (Vb).

In some embodiments of compounds of formulas (Ia) (IIa), (IIIa), (IVa), or (Va), m is an integer ranging from about 2 to about 30, or from about 30 to about 100, or from about 20 to about 200, or alternatively, from about 100 to about 500. In another embodiment, m is an integer ranging from about 500 to about 1,000; and in still another embodiment m is an integer ranging from about 1,000 to about 2,000. Compounds of formulas (Ia) (IIa), (IIIa), (IVa), or (Va) may also have the value of m adjusted such that the molecular weight range (in Daltons) of the compound is from about 500 to about 2000, or from 2,000 to about 5,000, or from about 5,000 to about 10,000, or from about 10,000 to about 50,000, or from about 50,000 to about 100,000, or from about 100,000 to about 200,000. Exemplary molecular weights for compounds of formulas (Ia) (IIa), (IIIa), (IVa), or (Va) include about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, about 75,000 Daltons, about 80,000 Daltons, about 90,000 Daltons, about 100,000 Daltons, about 120,000 Daltons, about 140,000 Daltons about 150,000 Daltons and about 175,000 Daltons.

In some embodiments of compounds of formulas (Ib), (IIb), (IIIb), (IVb), or (Vb) m is an integer ranging from about 2 to about 30, or from about 30 to about 100, or from about 20 to about 200, or alternatively, from about 100 to about 500. In some embodiments, m is an integer ranging from about 500 to about 1,000, and in other embodiments, m is an integer ranging from about 1,000 to about 2,000. Compounds of formulas (Ib), (IIb), (IIIb), (IVb), or (Vb) may also have the value of m adjusted such that the molecular weight range (in Daltons), excluding the molecular weight of the biologically active agent A, is from about 2,000 to about 5,000, or from about 5,000 to about 10,000, or from about 10,000 to about 50,000, or from about 50,000 to about 100,000, or from about 100,000 to about 200,000. Exemplary molecular weights for compounds of formulas (Ib) (IIb), (IIIb), (IVb), or (Vb) excluding the molecular weight of the biologically active agent A, include about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, about 75,000 Daltons, about 80,000 Daltons, about 90,000 Daltons, about 100,000 Daltons, about 120,000 Daltons, about 140,000 Daltons about 150,000 Daltons and about 175,000 Daltons In some embodiments of compounds of formulas (Ia) or (Ib), having multiple polymer arms where b is greater than or equal to 3, the value of m may be selected such that the molecular weight of the compounds excluding the weight of the active agent "A" when present, is from about 2,000 to about 300,000 Daltons. Other molecular weight ranges for compounds of formula (Ia) or (Ib) where b is greater than or equal to 3 are from about 5,000 to about 10,000, or from about 10,000 to about 50,000, or from about 50,000 to about 100,000, or from about 100,000 to about 200,000 or from about 200,000 to about 250,000 or from about 250,000 to about 300,000 Daltons, excluding the weight of the active agent "A" when present.

The length of the polymer in compounds of formula (Ia) through (Vb), and thus the mass, may be varied over at least the above stated ranges. Depending on the synthetic means employed and the subsequent purification methods employed the variation in the size/mass of compounds of formula (Ia) through (Vb) Ib may be controlled to give preparations having narrowly dispersed ranges, or alternatively, broadly dispersed ranges of size/mass.

In some embodiments of compounds of formulas (Ia), (IIa), (IIIa), (IVa), or (Va), X is a reactive group or a protected form thereof that can react with nucleophiles or electrophiles. In some embodiments, X is a group capable of reacting with a nucleophile or electrophile present in a biologically active agent. In other embodiments X is a group capable of reacting with a functionality selected from an aldehyde, a ketone, an amine, a carboxyl, a hydroxyl, guanido or thiol group of a biologically active agent to form a covalent linkage between the biologically active agent and the L group to which X was attached. The linkage between the biologically active agent and L may include one or more atoms derived from X, one or more atoms derived from the reaction of A with X, or atoms of an Sp1 group if present. Alternatively, the linkage between L and the biologically active agent may be a direct covalent bond where X is a group that may be displaced from L, such as a by a nucleophile of the biologically active agent acting in a $S_N1$ or $S_N2$ nucleophilic substitution reaction.

In other embodiments of compounds of formulas (Ia) (IIa), (IIIa), (IVa), or (Va) X is selected from the group consisting of: hydroxyl, thiol, disulfide, dithiopyridyl, aldehyde, aldehyde hydrate, ketone, thione, acetal, ketal, —$CH(OR^1)_2$, hemiacetal, hemiketal, monothioketal, dithiohemiketal, dithioketal, epoxide, thioepoxide, glyoxal, diones, amide, hydrazide, carboxyl, carboxylic acid ester, orthoester, N-hydroxysuccinimide ester, succinimidyl, maleimidyl, 1-benzotriazolyl, —$CO_2$-succinimidyl, —$CO_2$-maleimidyl, imidoester, guanido, —$CO_2$-(1-benzotriazolyl)amine, urea, carbamate, carbonate, thiourea, thiocarbamate, isocyanate, isothiocyanate, sulfone, chloroethylsulfone, alpha-beta substituted carbonyl, alpha-beta substituted carboxyl, acryloyl, acrylate, methacrylate, acrylamide, vinylsulfone, vinylpyridine, —O(C=O)—$CH_2$—I, —O(C=O)—$CH_2$—Br, —NH(C=O)—$CH_2$—I, —NH(C=O)—$CH_2$—Br, —(C=O)—$CH_2$—I, and —(C=O)—$CH_2$—Br; wherein $R^1$ is $C_{1-6}$ alkyl, $C_3$-$C_6$ cycloalkyl, or an aryl group having 5-8 endocyclic atoms.

In some embodiments of compounds of formulas (Ia), (IIa), (IIIa), (IVa), or (Va), X is a group selected from protected and unprotected forms of: hydroxyl, thiol, disulfide, dithiopyridyl, aldehyde, aldehyde hydrate, ketone, thione, acetal, ketal, —$CH(OR^1)_2$, hemiacetal, hemiketal, monothioketal, dithiohemiketal, dithioketal, epoxide, glyoxals, diones, amide, hydrazide, carboxyl, carboxylic acid ester, orthoester, succinimidyl, maleimidyl, 1-benzotriazolyl, —$CO_2$-succinimidyl, —$CO_2$-maleimidyl, and —$CO_2$-(1-benzotriazolyl); wherein $R^1$ is $C_1$-$C_6$ alkyl, $C_3$-$C_6$ cycloalkyl, or an aryl group having 5-8 endocyclic atoms.

In other embodiments of compounds of formulas (Ia) (IIa), (IIIa), (IVa), or (Va), X is a group selected from protected and unprotected forms of: ether, thioether, amine, urea, carbamate, carbonate, thiourea, thiocarbamate, isocyanate, isothiocyanate, sulfone, and chloroethylsulfone.

In yet other embodiments of compounds of formulas (Ia) (IIa), (IIIa), (IVa), or (Va), X is alpha-beta substituted carbonyl, $C_2$-$C_{12}$ alkenyl, acryloyl, acrylate, methacrylate, acrylamide, vinlysulfone and vinylpyridine. Where an X group contains a double bond that cannot be present in the polymerization reactions, such as where X comprises a vinyl pyridine group, an alpha-beta unsaturated carbonyl, an alpha-beta ester, vinlysulfone or an alpha-beta amide, the group may be introduced into the compounds following any polymerization process that creates the polymeric portion of the compounds of the invention. This may be accomplished, for example, through a bifunctional agent having a X group and a group capable of reacting with a functionality attached to the L group, such as an NHS ester, group both appended to an -($Sp^1$)- group.

Within compounds of formula (Ia) through (Vb), when n is 0 the spacer group $Sp^1$ is not present and -$Sp^1$- denotes a covalent bond such that L is directly bound to —Z-A or —X by a covalent bond.

When n is 1, -$Sp^1$- is present between A-Z— and -L- moieties or between X— and -L- moieties of compounds having formulas (Ia) through (Vb). In some embodiments, $Sp^1$ is selected from the group consisting of: an alkyl ether and an alkyl ester of an alkyl carboxylic acid. In other embodiments, $Sp^1$ is selected from the group consisting of: —$C_{1-12}$ alkyl-, —$C_{3-12}$cycloalkyl-, —($C_{1-8}$alkyl)-($C_{3-12}$cycloalkyl)-($C_{0-8}$ alkyl)-, —$(CH_2)_{1-12}$O—, (—$(CH_2)_{1-6}$—O—$(CH_2)_{1-6}$—$)_{1-12}$—, (—$(CH_2)_{1-4}$—NH—$(CH_2)_{1-4}$$)_{1-12}$—, (—$(CH_2)_{1-4}$—O—$(CH_2)_{1-4}$$)_{1-12}$—O—, (—$(CH_2)_{1-4}$—O—$(CH_2)_{1-4}$$)_{1-12}$O—$(CH_2)_{1-12}$—, —$(CH_2)_{1-12}$—(C=O)—O—, —$(CH_2)_{1-12}$—O—(C=O)—, -(phenyl)-$(CH_2)_{1-3}$—(C=O)—O—, -(phenyl)-$(CH_2)_{1-3}$—(C=O)—NH—, —($C_{1-6}$ alkyl)-(C=O)—O—($C_{0-6}$ alkyl)-, —$(CH_2)_{1-12}$—(C=O)—O—$(CH_2)_{1-12}$—, —CH(OH)—CH(OH)—(C=O)—O— —CH(OH)—CH(OH)—(C=O)—NH—, —S-maleimido-$(CH_2)_{1-6}$—, —S-maleimido-($C_{1-3}$ alkyl)-(C=O)—NH—, —S-maleimido-($C_{1-3}$ alkyl)-($C_{5-6}$ cycloalkyl)-($C_{0-3}$ alkyl)-, —($C_{1-3}$ alkyl)-($C_{5-6}$ cycloalkyl)-($C_{0-3}$ alkyl)-(C=O)—O—, —($C_{1-3}$ alkyl)-($C_{5-6}$ cycloalkyl)-($C_{1-3}$ alkyl)-(C=O)—NH—, —S-maleimido-($C_{0-3}$ alkyl)-phenyl-($C_{0-3}$ alkyl)-, —($C_{0-3}$ alkyl)-phenyl-(C=O)—NH—, —$(CH_2)_{1-12}$—NH—(C=O)—, —$(CH_2)_{1-12}$—(C=O)—NH—, -(phenyl)-$(CH_2)_{1-3}$—(C=O)—NH—, —S—$(CH_2)$—(C=O)—NH-(phenyl)-, —$(CH_2)_{1-12}$—(C=O)—NH—$(CH_2)_{1-12}$—, —$(CH_2)_2$—(C=O)—O—$(CH_2)_2$—O—(C=O)—$(CH_2)_2$—(C=O)—NH—, —($C_{1-6}$ alkyl)-(C=O)—N—($C_{1-6}$ alkyl)-, acetal, ketal, acyloxyalkyl ether, —N=CH—, —($C_{1-6}$ alkyl)-S—S—($C_{0-6}$ alkyl)-, —($C_{1-6}$ alkyl)-S—S—($C_{1-6}$ alkyl)-(C=O)—O—, —($C_{1-6}$ alkyl)-S—S—($C_{1-6}$ alkyl)-(C=O)—NH—, —S—S—$(CH_2)_{1-3}$—(C=O)—NH—$(CH_2)_{1-4}$—NH—(C=O)—$(CH_2)_{1-3}$—, —S—S—($C_{0-3}$ alkyl)-(phenyl)-, —S—S—($C_{1-3}$-alkyl)-(phenyl)-(C=O)—NH—$(CH_2)_{1-5}$—, —($C_{1-3}$ alkyl)-(phenyl)-(C=O)—NH—$(CH_2)_{1-5}$—(C=O)—NH—, —S—S—($C_{1-3}$-alkyl)-, —($C_{1-3}$-alkyl)-(phenyl)-(C=O)—NH—, —O—($C_1$-$C_6$ alkyl)-S($O_2$)—($C_{1-6}$ alkyl)-O—(C=O)—NH—, —S—S—$(CH_2)_{1-3}$—(C=O)—, —$(CH_2)_{1-3}$—(C=O)—NH—N=C—S—S—$(CH_2)_{1-3}$—(C=O)—NH—$(CH_2)_{1-5}$—, —$(CH_2)_{1-3}$—(C=O)—NH—$(CH_2)_{1-5}$—(C=O)—NH—, —$(CH_2)_{0-3}$-(heteroaryl)-$(CH_2)_{0-3}$—, —$(CH_2)_{0-3}$-phenyl-$(CH_2)_{0-3}$—,

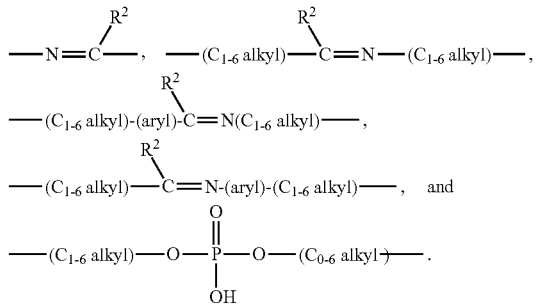

In another embodiment, $Sp^1$ is selected from the group consisting of: —$C_1$-$C_{12}$ alkyl-, —$C_3$-$C_{12}$ cycloalkyl-, (—$(CH_2)_{1-6}$—O—$(CH_2)_{1-6}$—$)_{1-12}$—, (—$(CH_2)_{1-4}$—NH—$(CH_2)_{1-4}$$)_{1-12}$—, —$(CH_2)_{1-12}$O—, (—$(CH_2)_{1-4}$—O—$(CH_2)_{1-4}$$)_{1-12}$—O—, —$(CH_2)_{1-12}$—(CO)—O—, —$(CH_2)_{1-12}$—(CO)—NH—, —$(CH_2)_{1-12}$—O—(CO)—, —$(CH_2)_{1-12}$—NH—(CO)—, (—$(CH_2)_{1-4}$—O—$(CH_2)_{1-4}$$)_{1-12}$—O—$(CH_2)_{1-12}$—, —$(CH_2)_{1-12}$—(CO)—O—$(CH_2)_{1-12}$—, —$(CH_2)_{1-12}$—(CO)—NH—$(CH_2)_{1-12}$—, —$(CH_2)_{1-12}$—O—(CO)—$(CH_2)_{1-12}$—, —$(CH_2)_{1-12}$—NH—(CO)—$(CH_2)_{1-12}$—, —($C_3$-$C_{12}$ cycloalkyl)-, —($C_1$-$C_8$alkyl)-($C_3$-$C_{12}$ cycloalkyl)-, —($C_3$-$C_{12}$ cycloalkyl)-($C_{1-8}$alkyl)-, —($C_{1-8}$-alkyl)-($C_3$-$C_{12}$ cycloalkyl)-($C_{1-8}$ alkyl)-, and —$(CH_2)_{0-3}$-aryl-$(CH_2)_{0-3}$—. When $Sp^1$ groups are present in a molecule of formulas (Ia) through (Vb), the $Sp^1$ group is preferentially oriented such that a carbon atom of $Sp^1$ is directly bound to X by a covalent bond.

Z is the product of the reaction between a group present in a biologically active agent and a reactive group (e.g., an X group of a compound of formulas (Ia) (IIa), (IIIa) (IVa) or (Va)) bound to an $Sp^1$ group when n is 1, or to L when n is 0. In some embodiments of compounds (Ib) (IIb), (IIIb), (IVb) or (Vb), Z is formed from a nucleophile or electrophile present in a biologically active agent and an X group that is capable of forming one or more covalent bonds through a reaction with the nucleophile or electrophile present in the biologically active agent. In other embodiments, Z is a group resulting from the formation of a covalent bond between an X group and an aldehyde, a ketone, a carboxyl group, an amine, a hydroxyl or a thiol present in a biologically active group.

Some non-limiting examples of Z groups formed from the reaction of some representative X groups and some groups typically found or introduced into biologically active agents are set forth in Table I.

TABLE I

| Biologically Active Agents and Illustrative Groups that may react with a reactive group (X) to form a Z group. | Exemplary Reactive X Groups of compounds (Ia), (IIa), (IIIa), (IVa), or (Va) (shown as appended to —$(Sp^1)_n$—‡) | Product A—Z—$(Sp^1)_n$—‡ |
|---|---|---|
| A—COOH | HO—$(Sp^1)_n$—‡ hydroxyl or activated forms thereof (e.g., tresylate, mesylate etc.) | A—C(=O)O—$(Sp^1)_n$—‡ |
| A—COOH | HS—$(Sp^1)_n$—‡ thiol | A—C(=O)S—$(Sp^1)_n$—‡ |
| A—SH | $R^1$—S—S—$(Sp^1)_n$—‡ (disulfide) | A—S—S—$(Sp^1)_n$—‡ |
| A—SH | (pyridyl)-S—S—$(Sp^1)_n$—‡ (dithiopyridyl) | A—S—S—$(Sp^1)_n$—‡ |
| A—$NH_2$ | H(O=)C—$(Sp^1)_n$—‡ aldehyde | A—N=CH—$(Sp^1)_n$—‡ or A—NH—$CH_2$—$(Sp^1)_n$—‡ following reduction |
| A—$NH_2$ | $(HO)_2HC$—$(Sp^1)_n$—‡ aldehyde hydrate | A—N=CH—$(Sp^1)_n$—‡ or A—NH—$CH_2$—$(Sp^1)_n$—‡ following reduction |
| A—$NH_2$ | $(R^1O)_2CH$—$(Sp^1)_n$-‡ or 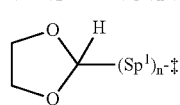 acetal | A—N=CH—$(Sp^1)_n$—‡ or A—NH—CH—$(Sp^1)_n$—‡ following reduction |
| A—$NH_2$ | $R^1OCH(OH)$—$(Sp^1)_n$—‡ or hemiacetal | A—N=CH—$(Sp^1)_n$—‡ or A—NH—CH—$(Sp^1)_n$—‡ following reduction |
| A—$NH_2$ | $R^1(O=)C$—$(Sp^1)_n$—‡ ketone | A—N=$CR^1$—$(Sp^1)_n$—‡ or A—NH—$C(R^1)H$—$(Sp^1)_n$—‡ following reduction |
| A—$NH_2$ | $(R^1O)_2CH$—$(Sp^1)_n$-‡ or 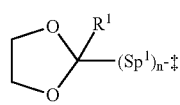 ketal | A—N=$C(R^1)$—$(Sp^1)_n$—‡ or A—NH—$C(R^1)H$—$(Sp^1)_n$—‡ following reduction |
| A—$NH_2$ | $R^1OCH(OH)$—$(Sp^1)_n$—‡ hemiketal | A—N=$C(R^1)$—$(Sp^1)_n$—‡ or A—NH—$C(R^1)H$—$(Sp^1)_n$—‡ following reduction |
| A—$NH_2$ | $R^1(S=)C$—$(Sp^1)_n$—‡ ketone thione (thioketone) | A—N=$C(R^1)$—$(Sp^1)_n$—‡ or A—NH—$C(R^1)H$—$(Sp^1)_n$—‡ following reduction |
| A—$NH_2$ | $(R^1O)(R^1S)CH$—$(Sp^1)_n$-‡ or 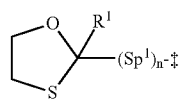 monothioketal | A—N=$C(R^1)$—$(Sp^1)_n$—‡ or A—NH—$C(R^1)H$—$(Sp^1)_n$—‡ following reduction |
| A—$NH_2$ | $R^1SCH(SH)$—$(Sp^1)_n$—‡ or dithiohemiketal | A—N=$C(R^1)$—$(Sp^1)_n$—‡ or A—NH—$C(R^1)H$—$(Sp^1)_n$—‡ following reduction |
| A—$NH_2$ | $(R^1S)_2CH$—$(Sp^1)_n$—‡ or 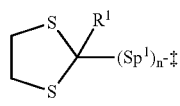 dithioketal | A—N=$C(R^1)$—$(Sp^1)_n$—‡ or A—NH—$C(R^1)H$—$(Sp^1)_n$—‡ following reduction |
| A—SH<br>A—OH<br>A—COOH (anion)<br>A—$NHR^2$ | 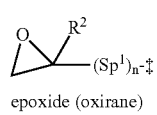 epoxide (oxirane) | A—S—$CH_2$—$C(OH)(R^2)(Sp^1)_n$—‡<br>A—O—$CH_2$—$C(OH)(R^2)(Sp^1)_n$—‡<br>A—C(=O)O—$CH_2$—$C(OH)(R^2)(Sp^1)_n$—‡<br>A—$NR^2$—$CH_2$—$C(OH)(R^2)(Sp^1)_n$—‡ |

TABLE I-continued

| Biologically Active Agents and Illustrative Groups that may react with a reactive group (X) to form a Z group. | Exemplary Reactive X Groups of compounds (Ia), (IIa), (IIIa), (IVa), or (Va) (shown as appended to —(Sp$^1$)$_n$—‡) | Product A—Z—(Sp$^1$)$_n$—‡ |
|---|---|---|
| A—SH<br>A—OH<br>A—COOH (anion)<br>A—NHR$^2$ | 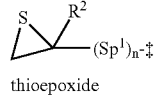<br>thioepoxide | A—S—CH$_2$—C(SH)(R$^2$)(Sp$^1$)$_n$—‡<br>A—O—CH$_2$—C(SH)(R$^2$)(Sp$^1$)$_n$—‡<br>A—C(=O)O—CH$_2$—C(SH)(R$^2$)(Sp$^1$)$_n$—‡<br>A—NR$^2$—CH$_2$—C(SH)(R$^2$)(Sp$^1$)$_n$—‡ |
| A—SH<br>A—OH<br>A—NHR$^2$ | HO—(C=O)—(Sp$^1$)$_n$—‡<br>carboxyl | A—S—(C=O)—(Sp$^1$)$_n$—‡<br>A—O—(C=O)—(Sp$^1$)$_n$—‡<br>A—NH—(C=O)—(Sp$^1$)$_n$—‡ |
| A—SH<br>A—OH<br>A—NHR$^2$ | (alcohol)-(C=O)—(Sp$^1$)$_n$—‡<br>carboxylic acid ester<br>(alcohol indicates an esterified suitable alcohol leaving group e.g., p-nitrophenyl) | A—S—(C=O)—(Sp$^1$)$_n$—‡<br>A—O—(C=O)—(Sp$^1$)$_n$—‡<br>A—NH—(C=O)—(Sp$^1$)$_n$—‡ |
| A—NH$_2$ | 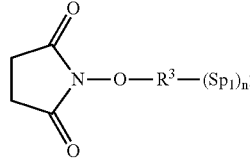<br>N-hydroxysuccinimide ester | A—NH—R$^3$—(Sp$^1$)$_n$—‡ |
| A—SH$_2$ | 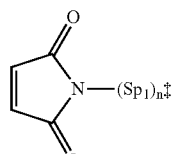 | 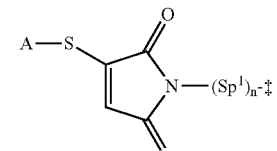 |
| A—NH$_2$ | 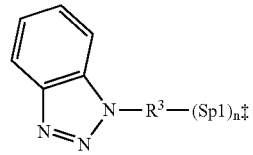<br>1-benzotriazole ester | A—NH—R$^3$—(Sp$^1$)$_n$—‡ |
| A—NH$_2$<br>A—(C=NH)—O(CH$_2$)$_{1-3}$—CH$_3$<br>(imidoester) | CH$_3$—(CH$_2$)$_{1-3}$—O(C=NH)—(Sp$^1$)$_n$—‡<br>(imidoester)<br>H$_2$N—(Sp$^1$)$_n$—‡ | A—NH—(C=NH)—(Sp$^1$)$_n$—‡<br>(amidine)<br>A—(C=NH)—HN—(Sp$^1$)$_n$—‡<br>(amidine) |
| A—COOH<br>A—(C=O)—R$^2$ | H$_2$N—(Sp$^1$)$_n$—‡<br>amine | A—(C=O)—NH—(Sp$^1$)$_n$—‡<br>A—(R$^2$)C=N—(Sp$^1$)$_n$—‡ or<br>A—(R$^2$)CH—NH—(Sp$^1$)$_n$—‡<br>following reduction |
| A—COOH<br>A—(C=O)—R$^2$ | H$_2$N—(C=O)—NH—(Sp$^1$)$_n$—‡<br>urea | A—(C=O)—NH—(C=O)—NH—(Sp$^1$)$_n$—‡<br>A—(R$^2$)C=N—(C=O)—NH—(Sp$^1$)$_n$—‡ or<br>A—(R$^2$)CH—NH—(C=O)—NH—(Sp$^1$)$_n$—‡<br>following reduction |
| A—COOH<br>A—(C=O)—R$^2$ | H$_2$N—(C=O)—O—(Sp$^1$)$_n$—‡<br>carbamate | A—(C=O)—NH—(C=O)—O—(Sp$^1$)$_n$—‡<br>A—(R$^2$)C=N—(C=O)—O—(Sp$^1$)$_n$—‡ or<br>A—(R$^2$)CH—NH—(C=O)—O—(Sp$^1$)$_n$—‡<br>following reduction |
| A—COOH<br>A—(C=O)—R$^2$ | H$_2$N—(C=S)—NH—(Sp$^1$)$_n$—‡<br>thiourea | A—(C=O)—NH—(C=S)—NH—(Sp$^1$)$_n$—‡<br>A—(R$^2$)C=N—(C=S)—NH—(Sp$^1$)$_n$—‡ or<br>A—(R$^2$)CH—NH—(C=S)—NH—(Sp$^1$)$_n$—‡<br>following reduction |
| A—COOH<br>A—(C=O)—R$^2$ | H$_2$N—(C=S)—O—(Sp$^1$)$_n$—‡<br>thiocarbamate | A—(C=O)—NH—(C=S)—O—(Sp$^1$)$_n$—‡<br>A—(R$^2$)C=N—(C=S)—O—(Sp$^1$)$_n$—‡ or<br>A—(R$^2$)CH—NH—(C=S)—O—(Sp$^1$)$_n$—‡<br>following reduction |
| A—(C=O)—R$^2$ | H$_2$N—HN—(Sp$^1$)$_n$—‡ | A—(R$^2$)C=N—HN—(Sp$^1$)$_n$—‡<br>hydrazone |
| A—NH—NH$_2$ | R$^2$—(O=C)—(Sp$^1$)$_n$—‡ | A—NH—N=C(R$^2$)—(Sp$^1$)$_n$—‡<br>hydrazone |
| A—NH$_2$<br>A—OH<br>A—NH$_2$ | O=C=N—(Sp$^1$)$_n$—‡<br>isocyanate<br>S=C=N—(Sp$^1$)$_n$—‡ | A—NH—(C=O)—NH—(Sp$^1$)$_n$—‡<br>A—O—(C=O)—NH—(Sp$^1$)$_n$—‡<br>A—NH—(C=S)—NH—(Sp$^1$)$_n$—‡ |

TABLE I-continued

| Biologically Active Agents and Illustrative Groups that may react with a reactive group (X) to form a Z group. | Exemplary Reactive X Groups of compounds (Ia), (IIa), (IIIa), (IVa), or (Va) (shown as appended to —(Sp$^1$)$_n$—‡) | Product A—Z—(Sp$^1$)$_n$—‡ |
|---|---|---|
| A—OH | isothiocyanate | A—O—(C=S)—NH—(Sp$^1$)$_n$—‡ |
| A—SH | H$_2$C=CH—(C=O)—(Sp$^1$)$_n$—‡ or H$_2$C=C(CH$_3$)—(C=O)—(Sp$^1$)$_n$—‡ alpha-beta unsubstituted carbonyls | A—S—CH$_2$CH$_2$—(C=O)—(Sp$^1$)$_n$—‡ A—S—CH$_2$—CH(CH$_3$)—(C=O)—(Sp$^1$)$_n$—‡ |
| A—SH | H$_2$C=CH—(C=O)O—(Sp$^1$)$_n$—‡ alpha-beta unsubstituted carboxyl | A—S—CH$_2$CH$_2$—(C=O)O—(Sp$^1$)$_n$—‡ |
| A—SH | H$_2$C=C(CH$_3$)—(C=O)—O—(Sp$^1$)$_n$—‡ alpha-beta unsubstituted carboxyls (methacrylates) | A—S—CH$_2$CH(CH$_3$)—(C=O)O—(Sp$^1$)$_n$—‡ |
| A—SH | H$_2$C=CH—(C=O)NH—(Sp$^1$)$_n$—‡ alpha-beta unsubstituted amides (acrylamides) | A—S—CH$_2$CH$_2$—(C=O)NH—(Sp$^1$)$_n$—‡ |
| A—SH | vinylpyridine-(Sp$^1$)$_n$—‡ (2- or 4-vinylpyridine) | A—S—CH$_2$—CH$_2$-(pyridyl)-(Sp$^1$)$_n$—‡ |
| A—SH | H$_2$C=CH—SO$_2$—(Sp$^1$)$_n$—‡ (vinyl sulfone) | A—S—H$_2$C—CH$_2$—SO$_2$—(Sp$^1$)$_n$—‡ |
| A—SH | ClH$_2$C—CH$_2$—SO$_2$—(Sp$^1$)$_n$ (chloroethyl sulfone) | A—S—H$_2$C—CH$_2$—SO$_2$—(Sp$^1$)$_n$—‡ |
| A—SH | (halogen)-CH$_2$—(C=O)—O—(Sp$^1$)$_n$—‡ (halogen)-CH$_2$—(C=O)—NH—(Sp$^1$)$_n$—‡ (halogen)-CH$_2$—(C=O)—(Sp$^1$)$_n$—‡ (halogen is preferably I or Br) | A—S—CH$_2$—(C=O)—O—(Sp$^1$)$_n$—‡ A—S—CH$_2$—(C=O)—NH—(Sp$^1$)$_n$—‡ A—S—CH$_2$—(C=O)—(Sp$^1$)$_n$—‡ |
| A—O(C=O)—CH2-(halogen) A—NH(C=O)—CH2-(halogen) A—(C=O)—CH2-(halogen) (halogen is preferably I or Br) | HS—(Sp$^1$)$_n$—‡ | A—O(C=O)—CH2—S—(Sp$^1$)$_n$—‡ A—NH(C=O)—CH2—S—(Sp$^1$)$_n$—‡ A—(C=O)—CH2—S—(Sp$^1$)$_n$—‡ |
| A—SH | (halogen)-CH$_2$(C=O)O—(Sp$^1$)$_n$—‡ (halogen)-CH$_2$(C=O)NH—(Sp$^1$)$_n$—‡ (halogen)-CH$_2$(C=O)—(Sp$^1$)$_n$—‡ (halogen is preferably I or Br) | A—S—CH$_2$(C=O)O—(Sp$^1$)$_n$—‡ A—S—CH$_2$(C=O)NH—(Sp$^1$)$_n$—‡ A—S—CH$_2$(C=O)—(Sp$^1$)$_n$—‡ |

$R^1$ is $C_{1-6}$ alkyl, $C_{3-6}$ cycloalkyl, or an aryl group having 5-8 endocyclic atoms;
$R^2$ is H, $C_{1-6}$ alkyl, $C_{3-6}$ cycloalkyl, or an aryl group having 5-8 endocyclic atoms;
$R^3$ is an carbonyl derivative *—(C=O)—, *—(C=O)—(CH$_2$)$_{1-8}$—S—S—, *—(C=O)—(CH$_2$)$_{1-8}$—(C=O)—O—,
*—(C=O)—(CH$_2$)$_{1-8}$—O—(C=O)—, *—(C=O)—(CH$_2$)$_{1-8}$—(C=O)—NH—, or *—(C=O)—(CH$_2$)$_{1-8}$—NH—(C=O)—, or alternatively,
$R^3$ is carbonyl derivative of the form *—(C=O)—O—(CH$_2$)$_{1-8}$—S—S—, *—(C=O)—O—(CH$_2$)$_{1-8}$—(C=O)—O—,
*—(C=O)—O—(CH$_2$)$_{1-8}$—O—(C=O)—, *—(C=O)—O—(CH$_2$)$_{1-8}$—(C=O)—NH—, or *—(C=O)—O—(CH$_2$)$_{1-8}$—NH—(C=O)—,
*where "*" indicates the point of attachment to succinimidyl or benzotriazolyl groups;
N is independently 0 or 1; and
‡ indicates the point of attachment to an L group.

The biologically active agent, A, of compounds of formula (Ib), (IIb), (IIIb), (IVb), or (Vb) may include a spacer group, (Sp$^2$)$_p$, as a means of linking the active agent, A, to Z. When p is 0 the spacer group Sp$^2$ is not present and -Sp$^2$- denotes a covalent bond such that the biologically active agent "A" links directly to the Z group by one or more (e.g., a double bond) covalent bonds. When n is 1, the spacer group denoted Sp$^2$ is present between the A and Z groups, and compounds of formula (Ib) may be written as (A(Sp$^2$)$_p$-Z-(Sp$^1$)$_n$)$_a$-L-(K)$_b$, where all components except (Sp$^2$) and p are as defined for compounds of formula (Ib); and p is 0 or 1. In some embodiments, Sp$^2$ spacer groups may comprise an alkyl ether and an alkyl ester of an alkyl carboxylic acid.

In other embodiments of compounds of formula (Ib), (IIb), (IIIb), (IVb), or (Vb), Sp$^2$ is selected from the group consisting of: —C$_{1-12}$ alkyl-, —C$_{3-12}$ cycloalkyl-, —(C$_{1-8}$ alkyl)-(C$_{3-12}$ cycloalkyl)-(C$_{0-8}$ alkyl)-, —(CH$_2$)$_{1-12}$O—, (—(CH$_2$)$_{1-6}$—O—(CH$_2$)$_{1-6}$—)$_{1-12}$, (—(CH$_2$)$_{1-4}$—NH—(CH$_2$)$_{1-4}$)$_{1-12}$—, (—(CH$_2$)$_{1-4}$—O—(CH$_2$)$_{1-4}$)$_{1-12}$—O—, (—(CH$_2$)$_{1-4}$—O—(CH$_2$)$_{1-4}$—)$_{1-12}$O—(CH$_2$)$_{1-12}$—, —(CH$_2$)$_{1-12}$—(C=O)—O—, —(CH$_2$)$_{1-12}$—O—(C=O)—, -(phenyl)-(CH$_2$)$_{1-3}$—(C=O)—O—, -(phenyl)-(CH$_2$)$_{1-3}$—(C=O)—NH—, —(C$_{1-6}$ alkyl)-(C=O)—O—(C$_{0-6}$ alkyl)-, —(CH$_2$)$_{1-12}$—(C=O)—O—(CH$_2$)$_{1-12}$—, —CH(OH)—CH (OH)—(C=O)—O— —CH(OH)—CH(OH)—(C=O)— NH—, —S-maleimido-(CH$_2$)$_{1-6}$—, —S-maleimido-(C$_{1-3}$ alkyl)-(C=O)—NH—, —S-maleimido-(C$_{1-3}$ alkyl)-(C$_{5-6}$ cycloalkyl)-(C$_{0-3}$ alkyl)-, —(C$_{1-3}$ alkyl)-(C$_{5-6}$ cycloalkyl)-(C$_{0-3}$ alkyl)-(C=O)—O—, —(C$_{1-3}$ alkyl)-(C$_{5-6}$ cycloalkyl)-(C$_{1-3}$ alkyl)-(C=O)—NH—, —S-maleimido-(C$_{0-3}$ alkyl)-phenyl-(C$_{0-3}$ alkyl)-, —(C$_{0-3}$ alkyl)-phenyl-(C=O)—NH—, —(CH$_2$)$_{1-12}$—NH—(C=O)—, —(CH$_2$)$_{1-12}$—(C=O)—NH—, -(phenyl)-(CH$_2$)$_{1-3}$—(C=O)—NH—, —S—(CH$_2$)—(C=O)—NH-(phenyl)-, —(CH$_2$)$_{1-12}$—(C=O)—NH—(CH$_2$)$_{1-12}$—, —(CH$_2$)$_2$—(C=O)—O—(CH$_2$)$_2$—O—(C=O)—(CH$_2$)$_2$—(C=O)—NH—, —(C$_{1-6}$ alkyl)-(C=O)—N—(C$_{1-6}$ alkyl)-, acetal, ketal, acyloxyalkyl ether, —N=CH—, —(C$_{1-6}$ alkyl)-S—S—(C$_{0-6}$ alkyl)-, —(C$_{1-6}$ alkyl)-S—S—(C$_{1-6}$ alkyl)-(C=O)—O—, —(C$_{1-6}$ alkyl)-S—S—(C$_{1-6}$ alkyl)-(C=O)—NH—, —S—S—(CH$_2$)$_{1-3}$—(C=O)—NH—(CH$_2$)$_{1-4}$—NH—(C=O)—(CH$_2$)$_{1-3}$—, —S—S—(C$_{0-3}$ alkyl)-(phenyl)-, —S—S—(C$_{1-3}$-alkyl)-(phenyl)-(C=O)—NH—(CH$_2$)$_{1-5}$—, —(C$_{1-3}$ alkyl)-(phenyl)-(C=O)—NH—(CH$_2$)$_{1-5}$—(C=O)—NH—, —S—S—(C$_{1-3}$-alkyl)-, —(C$_{1-3}$-alkyl)-(phenyl)-(C=O)—NH—, —O—(C$_1$-C$_6$ alkyl)-S(O$_2$)—(C$_{1-6}$ alkyl)-O—(C=O)—NH—, —S—S—(C$_{1-3}$)—(C=O)—, —(CH$_2$)$_{1-3}$—(C=O)—NH—N=C—S—S—(CH$_2$)$_{1-3}$—(C=O)—NH—(CH$_2$)$_{1-5}$—, —(CH$_2$)$_{1-3}$—(C=O)—NH—(CH$_2$)$_{1-5}$—(C=O)—NH—, —(CH$_2$)$_{0-3}$-(heteroaryl)-(CH$_2$)$_{0-3}$—, —(CH$_2$)$_{0-3}$-phenyl-(CH$_2$)$_{0-3}$—,

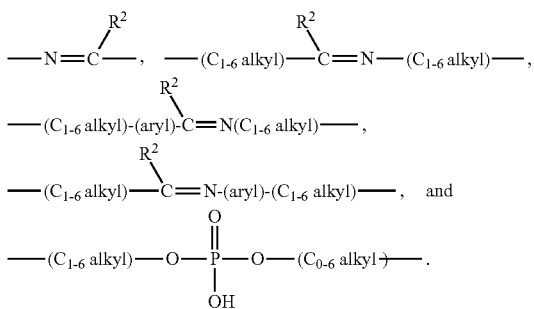

In another embodiment of compounds of formula (Ib), (IIb), (IIIb), (IVb), or (Vb), $Sp^2$ spacer groups are selected from: $—C_1-C_{12}$ alkyl-, $C_3-C_{12}$ cycloalkyl, $(—(CH_2)_{1-6}—O—(CH_2)_{1-6}—)_{1-12}—$, $(—(CH_2)_{1-4}—NH—(CH_2)_{1-4})_{1-12}—$, $—(CH_2)_{1-12}O—$, $(—(CH_2)_{1-4}—O—(CH_2)_{1-4})_{1-12}—O—$, $—(CH_2)_{1-12}—(CO)—O—$, $—(CH_2)_{1-12}—(CO)—NH—$, $—(CH_2)_{1-12}—O—(CO)—$, $—(CH_2)_{1-12}—NH—(CO)—$, $(—(CH_2)_{1-4}—O—(CH_2)_{1-4})_{1-12}—O—(CH_2)_{1-12}—$, $—(CH_2)_{1-12}—(CO)—O—(CH_2)_{1-12}—$, $—(CH_2)_{1-12}—(CO)—NH—(CH_2)_{1-12}—$, $—(CH_2)_{1-12}—O—(CO)—(CH_2)_{1-12}—$, $—(CH_2)_{1-12}—NH—(CO)—(CH_2)_{1-12}—$, $—(C_3-C_{12}$ cycloalkyl)-, $—(C_1-C_8$alkyl)-$(C_3-C_{12}$ cycloalkyl)-, $—(C_3-C_{12}$ cycloalkyl)-$(C_{1-8}$alkyl)-, and $—(C_{1-8}$alkyl)-$(C_3-C_{12}$ cycloalkyl)-$(C_{1-8}$alkyl)-.

Although the spacer group $Sp^2$, when present, is considered to be appended to the biologically active agent, A, for the purpose of synthesizing compounds of formula (Ib) or its sub-embodiments (IIb), (IIIb), (IVb) and (Vb), the $Sp^2$ spacer group, or a precursor to it, may be introduced into the molecule to form the bond to Z followed by formation of the bond between A and $Sp^2$. In this regard, some $Sp^2$ spacer groups may be considered to be bifunctional agents having both a group capable of reaction with a reactive group X of compounds (Ia), (IIa), (IIIa), (IVa), or (Va) to form a Z group, and a group capable of reacting with a group present in a biologically active agent thereby forming molecules of the form $(A(Sp^2)_p$-Z-$(Sp^1)_n)_a$-L-$(K)_b$ where p is 1. A variety of bifunctional reagents that may be employed as a source of $Sp^1$ and $Sp^2$ spacer groups are available from commercial suppliers including Pierce Biotechnology, Inc., (Rockford, Ill., USA), (see, e.g., Table II).

TABLE II

| |
|---|
| 3-([2-Aminoethyl]) dithio)-propionic acid•HCl |
| N-(α-Maleimidoacetoxy)-succinimide ester |
| 1,4-Bis-Maleimidobutane |
| 1,4-Bis-Maleimidyl-2,3-dihydroxybutane |
| Bis-Maleimidohexane |
| Bis-Maleimidoethane |
| N-β-Maleimidopropionic acid |
| N-(β-Maleimidopropionic acid)hydrazide•TFA |
| N-(β-Maleimidopropyloxy)succinimide ester |
| 1,8-Bis-Maleimidotriethyline-glycol |
| 1,11-Bis-Maleimidotetraethyleneglycol |
| Bis(2-[succinimidoxycarbonyloxy]ethyl)sulfone |
| Bis(sulfosuccinimidyl)suberate |
| C6-Succinimidyl 4-hydrazinonicotinate acetone hydrazone |
| C6-Succinimidyl 4-formylbenzoate |
| 1-5-Difluoro-2,4-dinitrobenzene |
| Dimethyl adipimidate•2HCl |
| Dimethyl pimelimidate•2HCl |
| Dimethyl suberimidate•2HCl |
| 1,4-Di-(3'-[2'pyridyldithio]propionamido) butane |
| Disuccinimidyl glutarate |

TABLE II-continued

| |
|---|
| Dithiobis(succimidylpropionate)(Lomant's Reagent) |
| Disuccinimidyl suberate |
| Disuccinimidyl tartarate |
| Dimethyl 3,3'-dithiobispropionimidate•2HCl |
| Dithiobis-maleimidoethane |
| 3,3'-Dithiobis(sulfosuccinimidylpropionate) |
| Ethylene glycol bis(succinimidylsuccinate) |
| N-ϵ-Maleimidocaproic acid |
| N-(ϵ-Maleimidocaproic acid)hydrazide |
| N-(ϵ-Maleimidocaproyloxy)succinimide ester |
| N-(γ-Maleimidobutryryloxy)succinimide ester |
| 1,6-Hexane-bis-vinylsuflone |
| N-κ-Maleimidoundecanoic acid |
| N-(κ-Maleimidoundecanoic acid)hydrazide |
| Succinimidyl 4-(N-maleimidomethyl) cyclohexane-1-carboxy-(6-amidocaproate) |
| Succinimidyl 6-(3'-[2-pyridyl-dithio]propionamido)hexanoate |
| m-Maleimidobenzoyl-N-hydroxysuccinimide ester |
| 4-(4-N-Maleimidophenyl)-butyric acid hydrazide•HCl |
| Methyl N-succinimidyl adipate |
| lysinyl]ethylmethanethiosulfate |
| 3-2(2-Pyridyldithio)propionylhydrazide |
| N-(p-Maleimidophenyl)isocyanate |
| Succinimidyl 4-hydrazinonicotinate acetone hydrazone |
| N-Succinimidyl S-acetylthioacetate |
| N-Succinimidyl S-acetylthioproprionate |
| Succinimdyl 3-(bromoacetamido)propionate |
| Succinimidyl 4-formylbenzoate |
| N-succinimidyl iodoacetate |
| N-Succinimidyl(4-iodoacetyl)aminobenzoate |
| Succinimidyl 4-(N-maleimido-methyl)cyclohexane-1-carboxylate |
| Succinimidyl 4-(p-maleimido-phenyl)butyrate |
| Succinimidyl-6-(β-maleimidopropionamido)hexanoate |
| 4-Succinimidyloxycarbonyl-methyl-α-(2-pyridyldithio)toluene |
| Succinimidyl-(4-psoralen-8-yloxy)butyrate |
| N-Succinimidyl 3-(2-pyridyldithio)propionate |
| Sulfodisuccinimidyl tartarate |
| Ethylene glycol bis(sulfo-succinimidyl succinate) |
| N-(ϵ-Maleimidocaproyloxy)sulfosuccinimide ester |
| N-(γ-Maleimidobutryloxy)sulfosuccinimide ester |
| N-(κ-Maleimidoundecanoyloxy)sulfosuccinimide ester |
| Sulfosuccinimidyl 6-(α-methyl-α-[2-pyridyldithio]-toluamido)hexanoate |
| Sulfosuccinimidyl 6-(3'[2-pyridyl-dithio]propionamido)hexanoate |
| m-Maleimidobenzoyl-N-hydroxysulfosuccinimide ester |
| Sulfosuccinimidyl(4-iodo-acetyl)aminobenzoate |
| Sulfosuccinimidyl 4-(N-maleimido-methyl)cyclohexane-1-carboxylate |
| Sulfosuccinimidyl 4-(p-maleimidophenyl)butyrate |
| N-(ϵ-Trifluoracetylcaproyloxy)succinimide ester |
| β-(Tris[hydroxymethyl]phosphine)propionic acid (betaine) |
| Tris-(2-Maleimidoethyl)amine (Trifunctional) |
| Tris-(succimimidyl aminotricetate) (Trifunctional) |

In those embodiments of compounds of formulas (Ia) through (Vb) where n is 1, a -($Sp^1$)- spacer group is present; and in those embodiments where n is 0, the spacer group $Sp^1$ is not present, and -$Sp^1$- denotes a covalent bond. Similarly, in some embodiments of compounds of formulas (Ib), (IIb), (IIIb), (IVb), or (Vb), both n and p are 0, and the spacer groups $Sp^1$ and $Sp^2$ denote a covalent bond. In other embodiments of compounds of formulas (Ib), (IIb), (IIIb), (IVb), and (Vb), both n and p are 1, or alternatively n is 1 and p is 0, or alternatively n is 0 and p is 1.

In some compounds of formulas (Ia) through (Vb), the spacer groups $Sp^1$ or $Sp^2$, when present, comprise a hydrolytically susceptible linkage or an enzymatically degradable linkage. In some embodiments of the present invention, the hydrolytically susceptible linkages or enzymatically degradable linkages present in $Sp^1$ or $Sp^2$ are independently selected from the group consisting of esters of carboxylic acids, phosphate esters, acetals, ketals, acyloxyalkyl ether, imines, orthoesters, disulfides, amides. In another embodiment of compounds of formulas (Ia) through (Vb) the spacer groups $Sp^1$ and $Sp^2$, when present, comprise a hydrolytically susceptible linkage or an enzymatically degradable linkages comprising amino acids, peptides, polypeptides, nucleic acids and oligonucleotides. In another embodiment, the hydrolytically susceptible or enzymatically degradable linkages are selected from the group consisting of esters of carboxylic acids, phosphate esters, acetals, ketals, acyloxyalkyl ether, imines, orthoesters, disulfides, some amides, peptides, polypeptides, nucleic acids, and oligonucleotides, each of which have a ($C_1$-$C_6$) alkyl group on both ends of the susceptible linkage. In another embodiment, the hydrolytically susceptible or enzymatically degradable linkages present in the $Sp^1$ and $Sp^2$ spacers have ($C_1$-$C_6$) alkyl groups on each end, and $Sp^1$ and $Sp^2$ are selected from the group consisting of —($C_1$-$C_6$ alkyl)-(C=O)—O—($C_1$-$C_6$ alkyl)-, —($C_0$-$C_6$ alkyl)-$PO_4$(H)—($C_0$-$C_6$ alkyl)- or a salt thereof, —($C_1$-$C_6$ alkyl)-S—S—($C_1$-$C_6$ alkyl)-, —($C_1$-$C_6$ alkyl)-(C=O)—N—($C_1$-$C_6$ alkyl)-, or —($C_1$-$C_6$ alkyl)-C=N—($C_1$-$C_6$ alkyl)-. In another embodiment the $Sp^1$ and $Sp^2$ linkages are selected from the group consisting of —($C_1$-$C_6$ alkyl)-(aryl)-C=N—($C_1$-$C_6$ alkyl)- and —($C_1$-$C_6$ alkyl)-C=N-(aryl)-($C_1$-$C_6$ alkyl)-. The skilled artisan will recognize that many hydrolytically susceptible linkages are also enzymatically degradable linkages. For the purpose of this disclosure, an enzymatically degradable linkage may be placed at any position where a hydrolytically susceptible linkage may be placed.

The Z group itself may also be a hydrolytically susceptible or enzymatically degradable linkage. In one embodiment the Z group may be selected from an amide, an ester or an imine, particularly an imine bearing an adjacent aryl group (i.e., a Schiff base). In another embodiment, Z may be a carboxylic acid ester, or an amide of a carboxylic acid.

In some embodiments of compounds (Ib), (IIb), (IIIb), (IVb) and (Vb), the active agent, A, may be released when it is bound by a hydrolytically susceptible linkage. In one embodiment where p is 0, the linkage between A and Z is a hydrolytically susceptible or an enzymatically degradable linkage, which upon cleavage releases A (e.g., Z is a hydrolytically susceptible or an enzymatically degradable linkage). In another embodiment, where p is 1, A is bound to its $Sp^2$ spacer group by a hydrolytically susceptible or enzymatically degradable linkage, the cleavage of which releases A. In some embodiments where p is 1, the $Sp^2$ spacer group comprises a hydrolytically susceptible or enzymatically degradable linkage or group, the cleavage of which releases A along with a covalently attached group derived from $Sp^2$. In one embodiment where p is 0 and A is a protein or polypeptide, A is bound directly to Z by a hydrolytically susceptible or enzymatically degradable linkage between A and Z. In another embodiment, where p is 1 and A is a protein or polypeptide, A is bound to its $Sp^2$ spacer group by a hydrolytically susceptible or enzymatically degradable linkage between the $Sp^2$ spacer group and A. In still another embodiment where p is 0 and A is a protein or polypeptide having a non-naturally occurring amino acid, A is bound directly to Z by a hydrolytically susceptible or enzymatically degradable linkage between Z and the non-naturally occurring amino acid in A. In yet another embodiment, where p is 1 and A is a protein or polypeptide having a non-natural amino acid, A is bound to its $Sp^2$ spacer group by a hydrolytically susceptible or enzymatically degradable linkage between the $Sp^2$ spacer group and the non-naturally occurring amino acid in A.

Biologically active agents denoted by the "A" group of formula (IV) may be broadly selected. In some embodiments the biologically active agents may be selected from drugs, vaccines, antibodies, antibody fragment, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA snRNA, RNAi, DNA, cDNA, antisense constructs, ribozymes, etc, and combinations thereof). In one embodiment, the biologically active agents may be selected from proteins, peptides, polypeptides and combinations thereof. In another embodiment, biologically active agents may be selected from nucleotides, oligonucleotides, polynucleotides, and nucleic acids (e.g., mRNA, tRNA snRNA, RNAi, DNA, cDNA, antisense constructs, ribozymes etc and combinations thereof). In another embodiment, biologically active agents may be selected from steroids, lipids, fats and combinations thereof.

In one particularly useful embodiment, the biologically active agent is a therapeutic protein. Numerous therapeutic proteins are disclosed throughout the application such as, and without limitation, erythropoietin, granulocyte colony stimulating factor (G-CSF), GM-CSF, interferon alpha, interferon beta, human growth hormone, and imiglucerase.

In one embodiment, the biologically active agents may be selected from specifically identified polysaccharide, protein or peptide biologically active agents, including but not limited to: agalsidase, alefacept, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, desmopressin, exendin-4, cytokines, cytokine receptors, granulocyte colony stimulating factor (G-CSF), thrombopoietin (TPO), alpha-I proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, I$^{131}$tositumomab, trastuzumab, tuvirumab, visilizumab, and fragments and mimetics thereof.

In one embodiment, the biologically active agent is a fusion protein. For example, and without limitation, the biologically active component may be an immunoglobulin or portion of an immunoglobulin fused to one or more certain useful peptide sequences. For example, the biologically active agent may contain an antibody Fc fragment. In one embodiment, the biologically active agent is a CTLA4 fusion protein. For example, the biologically active agent may be an Fc-CTLA4 fusion protein.

In one particularly useful embodiment, the biologically active agent is a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Therefore, in one embodiment, the biologically active agent is the human form of each of the proteins and polypeptides disclosed herein for which there is a human form. Examples of such human proteins include, without limitation, human antibodies, human enzymes, human hormones and human cytokines such as granulocyte colony stimulation factor, granulocyte macrophage colony stimulation factor, interferons (e.g., alpha interferons and beta interferons) and erythropoietin.

Other examples of therapeutic proteins which may serve as biologically active agents include, without limitation, factor VIII, b-domain deleted factor VIII, factor VIIa, factor IX, anticoagulants; hirudin, alteplase, tpa, reteplase, tpa, tpa-3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha1, ifn-beta, inf-beta 1b, ifn-beta 1a, ifn-gamma (e.g., 1 and 2), il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

Examples of therapeutic antibodies that may serve as biologically active agents include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$\beta_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Conjugates of the invention and compositions (e.g., pharmaceutical compositions) containing conjugates of the invention can be used to treat a variety of conditions. For example, there are many conditions for which treatment therapies are known to practitioners of skill in the art in which biologically active agents, as disclosed herein, are employed. The invention contemplates that the conjugates of the invention (e.g., phosphorylcholine containing polymer conjugated to a biologically active agent) and compositions containing the conjugates of the invention can be employed to treat such conditions and that such conjugates provide for an enhanced treatment therapy relative to the same biologically active agent not coupled to a phosphorylcholine containing polymer.

Therefore, the invention contemplates the treatment of a condition known to be treatable by a certain biologically active agent by treating the condition using the same certain biologically active agent conjugated to a phosphorylcholine containing polymer. For example, erythropoietin conjugated to a phosphorylcholine containing polymer can be used to treat human conditions such as anemia and kidney disease (e.g., chronic renal failure) and, for example, G-CSF conjugated to a phosphorylcholine containing polymer can be used to treat cancer patients receiving chemotherapy.

A skilled artisan will be able to determine the amount of a conjugate of the invention that produces a therapeutic effect by repeated administration of increasing amounts of the conjugate (e.g., pharmaceutical composition containing the conjugate) to achieve a clinically desired endpoint.

Proteins and peptides for use as biologically active agents as disclosed herein can be produced by any useful method including production by in vitro synthesis and by production in biological systems. Typical examples of in vitro synthesis methods which are well known in the art include solid-phase synthesis ("SPPS") and solid-phase fragment condensation ("SPFC"). Biological systems used for the production of proteins are also well known in the art. Bacteria (e.g., *E coli* and *Bacillus* sp.) and yeast (e.g., *Saccharomyces cerevisiae* and *Pichia pastoris*) are widely used for the production of heterologous proteins. In addition, heterologous gene expression for the production of biologically active agents for use as disclosed herein can be accomplished using animal cell lines such as mammalian cell lines (e.g., CHO cells). In one particularly useful embodiment, the biologically active agents are produced in transgenic or cloned animals such as cows, sheep, goats and birds (e.g., chicken, quail, ducks and turkey), each as is understood in the art. See, for example, U.S. Pat. No. 6,781,030, issued Aug. 24, 2004, the disclosure of which is incorporated in its entirety herein by reference.

Biologically active agents such as proteins produced in domesticated birds such as chickens can be referred to as "avian derived" biologically active agents (e.g., avian derived therapeutic proteins). Production of avian derived therapeutic proteins is known in the art and is described in, for example, U.S. Pat. No. 6,730,822, issued May 4, 2004, the disclosure of which is incorporated in its entirety herein by reference.

In embodiments where the biologically active agent is a protein or polypeptide, functional groups present in the amino acids of the protein polypeptide sequence may be used to link the agent to the Z group, either directly by a covalent bond, or indirectly through a $Sp^2$ spacer group. Linkages to protein or polypeptide biologically active agents may be made to naturally occurring amino acids in their sequence or to naturally occurring amino acids that have either been added to the sequence or inserted in place of another amino acid. Protein or polypeptide biologically active agents may also comprise non-naturally occurring amino acids in addition to the common naturally occurring amino acids found in proteins and polypeptides. In addition to being present for the purpose of altering the properties of a polypeptide or protein, non-naturally occurring amino acids may be introduced to provide a functional group that can be used to link the protein or polypeptide directly to the Z group, or indirectly through a $Sp^2$ spacer group appended to the active agent. Furthermore, naturally occurring amino acids, e.g., cysteine, may be used in this way.

Non-naturally occurring amino acids may be introduced into proteins and peptides by a variety of means. Some of the techniques for the introduction of non-natural amino acids are discussed in U.S. Pat. No. 5,162,218, the disclosure of which is incorporated in its entirety herein by reference. First, non-naturally occurring amino acids may be introduced by chemical modification of a polypeptide or protein on the amino acid side chain or at either the amino terminus or the carboxyl terminus. Non-limiting examples of chemical modification of a protein or peptide might be methylation by agents such as diazomethane, or the introduction of acetylation at an amino group present in lysine's side chain or at the amino terminus of a peptide or protein. Another example of the protein/polypeptide amino group modification to prepare a non-natural amino acid is the use of methyl 3-mercaptopropionimidate ester or 2-iminothiolane to introduce a thiol (sulfhydryl, —SH) bearing functionality linked to positions in a protein or polypeptide bearing a primary amine. Once introduced, such groups may be employed to form a covalent linkage to the protein or polypeptide. The use of bifunctional agents such as 2-iminothiolane may be considered as appending a $Sp^2$ group to a biologically active agent if the group introduced is used to form a covalent linkage to Z.

Second, non-naturally occurring amino acids may be introduced into proteins and polypeptides during chemical synthesis. Synthetic methods are typically utilized for preparing polypeptides having fewer than about 200 amino acids, usually having fewer than about 150 amino acids, and more usually having 100 or fewer amino acids. Shorter proteins or polypeptides having less than about 75 or less than about 50 amino acids can be prepared by chemical synthesis.

The synthetic preparation methods that are particularly convenient for allowing the insertion of non-natural amino acids at a desired location are known in the art. Suitable synthetic polypeptide preparation methods may be based on Merrifield solid-phase synthesis methods where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

Examples of non-naturally occurring amino acids that can be introduced during chemical synthesis of polypeptides include, but are not limited to: D-amino acids and mixtures of D and L-forms of the 20 naturally occurring amino acids, N-formyl glycine, ornithine, norleucine, hydroxyproline, beta-alanine, hydroxyvaline, norvaline, phenylglycine, cyclohexylalanine, t-butylglycine (t-leucine, 2-amino-3,3-dimethylbutanoic acid), hydroxy-t-butylglycine, amino butyric acid, cycloleucine, 4-hydroxyproline, pyroglutamic acid (5-oxoproline), azetidine carboxylic acid, pipecolinic acid, indoline-2-carboxylic acid, tetrahydro-3-isoquinoline carboxylic acid, 2,4-diaminobutyricacid, 2,6-diaminopimelic acid, 2,4-diaminobutyricacid, 2,6-diaminopimelicacid, 2,3-diaminopropionicacid, 5-hydroxylysine, neuraminic acid, and 3,5-diiodotyrosine.

Third, non-naturally occurring amino acids may be introduced through biological synthesis in vivo or in vitro by insertion of a non-sense codon (e.g., an amber or ocher codon) in a DNA sequence (e.g., the gene) encoding the polypeptide at the codon corresponding to the position where the non-natural amino acid is to be inserted. Such techniques are discussed for example in U.S. Pat. Nos. 5,162,218 and 6,964,859, the disclosures of which are incorporated in their entirety herein by reference. A variety of methods can be used to insert the mutant codon including oligonucleotide-directed mutagenesis. The altered sequence is subsequently transcribed and translated, in vivo or in vitro in a system which provides a suppressor tRNA, directed against the nonsense codon that has been chemically or enzymatically acylated with the desired non-naturally occurring amino acid. The synthetic amino acid will be inserted at the location corresponding to the nonsense codon. For the preparation of larger and/or glycosylated polypeptides, recombinant preparation techniques of this type are usually preferred. Among the amino acids that can be introduced in this fashion are: formyl glycine, fluoroalanine, 2-Amino-3-mercapto-3-methylbutanoic acid, homocysteine, homoarginine and the like.

Where non-naturally occurring amino acids have a functionality that is susceptible to selective modification, they are particularly useful for forming a covalent linkage to the protein or polypeptide. Circumstances where a functionality is susceptible to selective modification include those where the functionality is unique or where other functionalities that might react under the conditions of interest are hindered either stereochemically or otherwise.

In another embodiment, the biologically active agents may also be selected from specifically identified drug or therapeutic agents, including but not limited to: tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines. Biologically active agents may also be selected from the group consisting of aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine in another embodiment.

C. Pharmaceutical Compositions

The present invention includes and provides for pharmaceutical compositions comprising one or more compounds of the invention and one or more pharmaceutically acceptable excipients. The compounds of the invention may be present as a pharmaceutically acceptable salt, prodrug, metabolite, analog or derivative thereof, in the pharmaceutical compositions of the invention. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration.

Pharmaceutically acceptable carriers for use in formulating compounds of formula (Ia) through (Vb) include, but are not limited to: solid carriers such as lactose, terra alba, sucrose, talc, gelatin, agar, pectin, acacia, magnesium stearate, stearic acid and the like; and liquid carriers such as syrups, saline, phosphate buffered saline, water and the like. Carriers may include any time-delay material known in the art, such as glyceryl monostearate or glyceryl distearate, alone or with a wax, ethylcellulose, hydroxypropylmethylcellulose, methylmethacrylate or the like.

Other fillers, excipients, flavorants, and other additives such as are known in the art may also be included in a pharmaceutical composition according to this invention. The use of such media and agents for pharmaceutically active substances is well known in the art. Except insofar as any conventional media or agent is incompatible with the active compound, use thereof in the compositions of the invention is contemplated. Supplementary active compounds can also be incorporated into the compositions of the present invention.

The pharmaceutical preparations encompass all types of formulations. In some embodiments they are parenteral (including subcutaneous, intramuscular, intravenous, intradermal, intraperitoneal, intrathecal, intraventricular, intracranial, intraspinal, intracapsular, and intraosseous) formulations suited for injection or infusion (e.g., powders or concentrated solutions that can be reconstituted or diluted as well as suspensions and solutions). Where the composition is a solid that requires reconstitution or a concentrate that requires dilution with liquid media, any suitable liquid media may be employed. Preferred examples of liquid media include, but are not limited to, water, saline, phosphate buffered saline, Ringer's solution, Hank's solution, dextrose solution, and 5% human serum albumin.

Where a compound or pharmaceutical composition comprising a compound of formula (Ia) through (Vb) is suitable for the treatment of cell proliferative disorders, including but not limited to cancers, the compound or pharmaceutical composition can be administered to a subject through a variety of routes including injection directly into tumors, the blood stream, or body cavities.

While the pharmaceutical compositions may be liquid solutions, suspensions, or powders that can be reconstituted immediately prior to administration, they may also take other forms. In some embodiments, the pharmaceutical compositions may be prepared as syrups, drenches, boluses, granules, pastes, suspensions, creams, ointments, tablets, capsules (hard or soft) sprays, emulsions, microemulsions, patches, suppositories, powders, and the like. The compositions may also be prepared for routes of administration other than parenteral administration including, but not limited to, topical (including buccal and sublingual), pulmonary, rectal, transdermal, transmucosal, oral, ocular, and so forth.

In some embodiments, the pharmaceutical compositions of the present invention comprise one or more compounds of formula (Ib). In another embodiment, the pharmaceutical compositions of the present invention comprise one or more compounds of formula (IIb). In other embodiments, the pharmaceutical compositions of the present invention comprise one or more compounds of formula (IIIb), one or more compounds of formula (IVb), or one or more compounds of formula (Vb). In still other embodiments, the pharmaceutical compositions of the present invention comprise compounds of the present invention having star polymer conjugated to a biologically active agent. In other embodiments, the pharmaceutical compositions comprise two or more independently selected compounds of formula (Ib), (IIb), (IIIb) or (IVb), or (Vb), In an alternative embodiment, the pharmaceutical compositions comprise a compounds of formula (Ib), (IIb), (IIIb) or (IVb), or (Vb) and one or more additional biologically active agent. In some embodiments, the pharmaceutical compositions comprise one or more compounds of formula (Ib), (IIb), (IIIb) or (IVb), or (Vb) where the biologically active agent is selected from those specifically identified polysaccharide, protein or peptide biologically active agents set forth in section B.3; or alternatively, in other embodiments, those specifically identified drug or therapeutic agents set forth in section B.3.

Pharmaceutical compositions of the present invention may comprise a compound of the present invention having a biologically active agent selected from erythropoietin, granulocyte colony stimulating factor (G-CSF), interferon alpha, interferon beta, human growth hormone, and imiglucerase. In other embodiments, the pharmaceutical compositions comprise a compound of formula (IIb), (IIIb) or (IVb), or (Vb), where the biologically active agent is selected from erythropoietin, granulocyte colony stimulating factor (G-CSF), interferon alpha, interferon beta, human growth hormone, and imiglucerase. In other embodiments of the invention, the pharmaceutical compositions comprise a compound of formula ((IIIb) or (Vb), where the biologically active agent is selected from erythropoietin, granulocyte colony stimulating factor (G-CSF), interferon alpha, interferon beta, human growth hormone, and imiglucerase.

Other pharmaceutical compositions of the present invention may comprise one or more compounds of formulas (Ib), (IIb), (IIIb) or (IVb), or (Vb) that function as biological ligands that are specific to an antigen or target molecule. Such compositions may comprise a compound of formula ((IIIb) or (Vb), where the biologically active agent is a polypeptide that comprises the amino acid sequence of an antibody, or an antibody fragment such as a FAb2 or FAb' fragment or an antibody variable region. Alternatively, the compound may be a compound of formulas (IIb) or (IVb) and the polypeptide may comprise the antigen binding sequence of a single chain antibody. Where a biologically active agent present in a compound of formula (Ia) through (Vb) functions as a ligand specific to an antigen or target molecule, those compounds may also be employed as diagnostic reagents or in diagnostic assays.

The amount of a compound in a pharmaceutical composition will vary depending on a number of factors. In one embodiment, it may be a therapeutically effective dose that is suitable for a single dose container (e.g., a vial). In one embodiment, the amount of the compound is an amount suitable for a single use syringe. In yet another embodiment, the amount is suitable for multi-use dispensers (e.g., containers suitable for delivery of drops of formulations when used to deliver topical formulations). A skilled artisan will be able to determine the amount a compound that produces a therapeutically effective dose experimentally by repeated administration of increasing amounts of a pharmaceutical composition to achieve a clinically desired endpoint.

Generally, a pharmaceutically acceptable excipient will be present in the composition in an amount of about 0.01% to about 99.999% by weight, or about 1% to about 99% by weight. Pharmaceutical compositions may contain from about 5% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90% excipient by weight. Other suitable ranges of excipients include from about 5% to about 98%, from about from about 15 to about 95%, or from about 20% to about 80% by weight.

Pharmaceutically acceptable excipients are described in a variety of well known sources, including but not limited to "Remington: The Science & Practice of Pharmacy", $19^{th}$ ed., Williams & Williams, (1995) and Kibbe, A. H., Handbook of Pharmaceutical Excipients, $3^{rd}$ Edition, American Pharmaceutical Association, Washington, D.C., 2000.

D. Methods of Treatment

Another aspect of the present invention relates to methods of treating a condition responsive to a biological agent comprising administering to a subject in need thereof a therapeutically effective amount of a compound of the invention or of a pharmaceutically acceptable composition of the invention as described above. Dosage and administration are adjusted to provide sufficient levels of the biologically active agent(s) to maintain the desired effect. The appropriate dosage and/or administration protocol for any given subject may vary depending on various factors including the severity of the disease state, general health of the subject, age, weight, and gender of the subject, diet, time and frequency of administration, drug combination(s), reaction sensitivities, and tolerance/response to therapy. Therapeutically effective amounts for a given situation can be determined by routine experimentation that is within the skill and judgment of the clinician.

The pharmaceutical compositions described herein may be administered singly. Alternatively, two or more pharmaceutical compositions may be administered sequentially, or in a cocktail or combination containing two compounds of formulas (Ib), (IIb), (IIIb), (IVb), or (Vb) or one compound of formulas (Ib), (IIb), (IIIb) or (IVb), or (Vb) and another biologically active agent.

In some embodiments the methods of treatment will employ a pharmaceutical composition comprising one or more compounds of formula (Ia) through (Vb). In other embodiments, the treatment will employ a pharmaceutical composition comprising one or more compounds of formula (Ib), (IIb), (IIIb), (IVb) or (Vb). In still other embodiments, the treatment will employ a pharmaceutical composition comprising those compounds of the present invention having a star polymer conjugated to a biologically active agent. In other embodiments, methods of treatment comprise administering two or more independently selected compounds of formula (Ib), (IIb), (IIIb), (IVb), or (Vb). In still another embodiment, the method of treatment comprises administering one or more compounds of formula (Ib), (IIb), (IIIb) or (IVb), or (Vb) where the biologically active agent is selected from those specifically identified polysaccharide, protein or peptide biologically active agents or those specifically identified drug or therapeutic agents set forth in section B.3, above.

In some embodiments, the methods of treatment comprise administering to a subject or patient in need thereof a pharmaceutical composition comprising a compound of the present invention having a biologically active agent selected from the group consisting of: erythropoietin, granulocyte colony stimulating factor (G-CSF), interferon alpha, interferon beta, human growth hormone, and imiglucerase. In other embodiments of the invention, the pharmaceutical compositions comprise a compound of formula (Ib), (IIb), (IIIb), (IVb) or (Vb), where the biologically active agent is selected from the group consisting of: erythropoietin, granulocyte colony stimulating factor (G-CSF), interferon alpha, interferon beta, human growth hormone, and imiglucerase.

The use of erythropoietin for the treatment of anemia and in oncology, granulocyte colony stimulating factor (G-CSF) in oncology and immunology applications, interferon alpha in oncology applications and in the treatment of hepatitis C, interferon beta in the treatment of multiple sclerosis, human growth hormone in the treatment of growth disorders, and imiglucerase for the treatment of Gaucher's syndrome are well-described in the art. Other uses of biologically active agents set forth herein may be found in standard reference texts such as the Merck Manual of Diagnosis and Therapy, Merck & Co., Inc., Whitehouse Station, N.J. and Goodman and Gilman's The Pharmacological Basis of Therapeutics, Pergamon Press, Inc., Elmsford, N.Y., (1990).

Administration of the compounds and pharmaceutical compositions of the present invention can be achieved by any suitable route, including but not limited to various forms of injection. Routes of injection include subcutaneous, intramuscular, intravenous, intradermal, intraperitoneal, intrathecal, intraventricular, intracranial, intraspinal, intracapsular, and intraosseous. Injectable formulations include but are not limited to ready-for-injection solutions, emulsions, suspension and reconstitutable dry powders that are diluted with an acceptable solvent prior to administration, and liquid concentrates for dilution prior to administration, among others. The compositions may also be administer by other routes including, but not limited to, topical (including buccal and sublingual), pulmonary, rectal, transdermal, transmucosal, oral, nasal, ocular, intrathecal, subcutaneous, and intra-arterial.

E. Methods of Preparing Compounds of the Invention

Another aspect of the present invention relates to methods of preparing the compounds of the invention, such as compounds of formulas (Ia) through (Vb). The compounds may be prepared by any means known in the art for the preparation of polymer compounds and their conjugates. Standard synthetic methods and procedures for the preparation of organic molecules and functional group transformations and manipulations including the use of protective groups can be obtained from the relevant scientific literature or from standard reference textbooks in the field. Although not limited to any one or several sources, recognized reference textbooks of organic synthesis include: Smith, M. B.; March, J., March's Advanced Organic Chemistry: Reactions, Mechanisms, and Structure, $5^{th}$ ed.; John Wiley & Sons: New York, 2001; Greene, T. W.; Wuts, P. G. M., Protective Groups in Organic Synthesis, $3^{rd}$; John Wiley & Sons: New York, 1999; and Odian, G., Principles of Polymerization, $4^{th}$, Wiley-Interscience John Wiley & Sons: New York, 2004. The following descriptions of synthetic methods are designed to illustrate, but not limit, general procedures for the preparation of compounds of the invention.

E.1 Preparation of Monomers.

Preparation of the polymeric portion of the compounds of the invention may be accomplished by polymerization of suitable monomers of the form:

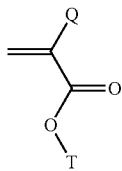

where Q is H, methyl, or ethyl, T is H, —CH$_3$, —CH$_2$—CH$_3$, and —CH$_2$—CH$_2$—O—PC, and PC denotes a phosphorylcholine group. When T is hydrogen and Q is H or methyl, the monomers are acrylic acid and 2-methylacrylic acid, respectively, both of which are commercially available from suppliers including Sigma-Aldrich. Ethyl methacrylate and methyl methacrylate are also available from Sigma-Aldrich. When T is hydrogen and Q is ethyl, the monomer is 2-ethylacrylic acid (EAA) which is commercially available or may be prepared from diethyl malonate or by the methods employed by Yong et al in J. Polymer Sci 42:3828-3835 (2004). Monomers where T is —CH$_2$—CH$_2$—O—PC, including 2-methacryloyloxyethyl-2'-trimethylammonium ethyl phosphate inner salt (also referred to as hydroxyethylmethacryloyl phosphorylcholine, HEMA-PC or MPC), may be prepared as described in U.S. Pat. No. 5,741,923 from 2-hydroxyethylacrylic acid, 2-hydroxyethylmethacrylic acid, or 2-hydroxyethylethylacrylic acid.

E.2 Monomer Composition

In some embodiments of the invention, the polymeric group present in compounds of formulas (Ia) through (Vb) is poly[2-(methacryloyloxyethyl)-2'-(trimethylammonium) ethyl phosphate] (or an inner salt thereof) prepared from 2-methacryloyloxyethyl-2'-trimethylammonium ethyl phosphate or a salt thereof (also referred to as hydroxyethylmethacryloyl phosphorylcholine, HEMA-PC or MPC). In those embodiments where one or more comonomers are polymerized with 2-methacryloyloxyethyl-2'-trimethylammonium ethyl phosphate, the molar ratio of that zwitterionic monomer to the total amount of comonomers is in the range 1:50 to 50:1; in other embodiments, the ratio is in the range of about 1:10 to about 10:1, and in still other embodiments the ratio is in the range of about 1:5 to 1:1. In another group of embodiments, 2-methacryloyloxyethyl-2'-trimethylammonium ethyl phosphate monomers comprise 100% or about 100%, or about 98%, about 95%, about 90%, about 85%, about 80%, about 75%, about 70%, about 60% or about 50% of the total monomers present in any compound of formulas (Ia) through (Vb). Where 100% of the polymer comprises monomers of 2-methacryloyloxyethyl-2'-trimethylammonium ethyl phosphate (i.e., HEMA-PC), the polymeric portion ("polymeric group") of the compounds (shown without the L or E groups attached)

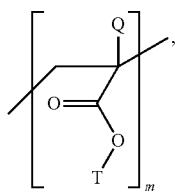

is poly[2-(methacryloyloxyethyl)-2'-(trimethylammonium) ethyl phosphate](i.e., poly-HEMA-PC).

E.3 Radical Polymerization and the Coupling to Biologically Active Agents

E.3.1 Living Radical/Pseudo-Living Radical Polymerizations

Compounds of the present invention may be prepared by diverse methods. One method of preparing the polymers of the invention includes living radical polymerization, which may advantageously be employed to prepare compounds of formulas (Ia) through (Vb) having specific architectures including controlled chain length and low polydispersity. Living radical polymerization, discussed by Odian, G. in Principles of Polymerization, 4$^{th}$, Wiley-Interscience John Wiley & Sons: New York, 2004, and applied to zwitterionic polymers for example in U.S. Pat. No. 6,852,816. Several different living radical polymerization methodologies may be employed, including Stable Free Radical Polymerization (SFRP) and Radical Addition-Fragmentation Transfer (RAFT). In addition, Atom Transfer Radical Polymerization (ATRP), considered by some to be a form of pseudo-living polymerization, provides a convenient method for the preparation of the compounds of the invention.

E.3.1.1 Initiators and Compound Architecture

The preparation of compounds of the formula (Ia) and (Ib) by ATRP is diagramed in Schemes IA and IB. The reaction involves the radical polymerization of selected monomers beginning with an initiator bearing one or more halogens (e.g., (X-(Sp$^1$)$_n$)$_a$-L-halogen(s)) that provides group -L-((Sp$^1$)$_n$-X)$_a$ (Scheme IA). The initiator is activated by a catalyst such as a transition metal salt that may be solubilized by a ligand (e.g., bipyridine). Alternatively, an initiator bearing one or more halogens may provide an L group with suitable functionalities (e.g., hydroxyl, amine, or carboxyl) for the subsequent addition of -(Sp$^1$)$_n$-X moieties (Scheme IB), which is particularly useful where an -(Sp$^1$)$_n$-X group is to be introduced by a bifunctional agent.

Schemes IA and B

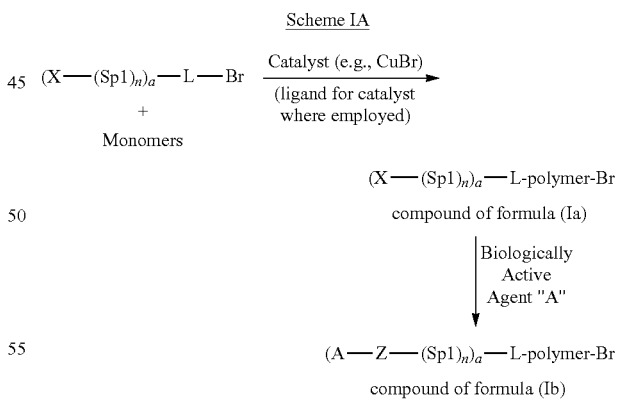

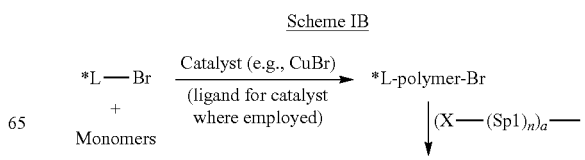

-continued $(X—(Sp1)_n)_a$—L-polymer-Br compound of formula (Ia)

↓ Biologically Active Agent "A"

$(A—Z—(Sp1)_n)_a$—L-polymer-Br compound of formula (Ib)

* indicates a linking functionality for joining —X—(Sp1)moieties with L

Compounds having complex architecture may also be prepared by ATRP as diagrammed in the two embodiments shown in Scheme IIA and IIB for branched and forked compounds. Schemes IIA and B

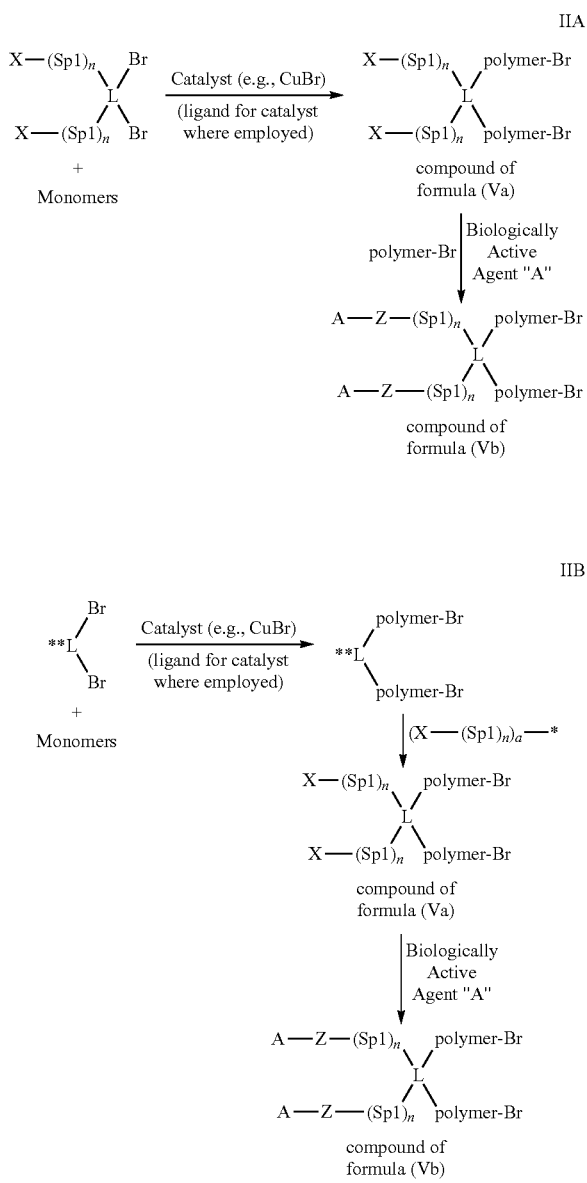

* indicates a linking functionality for joining —X—(Sp1)moieties with L

Compounds of formulas (Ia) and (Ib) include molecules having complex architectures including branched compounds having multiple polymer arms including, but not limited to, comb and star structures. Comb architectures may be achieved employing linear initiators bearing three or more halogen atoms, preferably the halogens are chlorine, bromine, or iodine atoms, more preferably the halogens are chlorine or bromine atoms. Star architectures may also be prepared employing compounds bearing multiple halogens on a single carbon atom (e.g., trichloromethanol, or 2,2,2-trichloroethanol etc.) or cyclic molecules bearing multiple halogens (e.g., tri- or tetrabromocycloalkanes such as tribromocyclohexanol or tetrabromocyclohexanol). In some embodiments compounds having star architecture have 3 polymer arms and in other embodiments they have 4 polymer arms.

While the halogen(s) set forth in Schemes I and II are indicated as bromine, other halogens may be employed, particularly chlorine. In some embodiments of compounds of formulas (Ia) through (Vb), including those having moieties with comb or star polymer architectures, the halogens bromine, chlorine and iodine are preferred. In other embodiments the halogens of compounds of formulas (Ia) through (Vb), including those having moieties with comb or star polymer architectures, are bromine and chlorine.

In those embodiments where an initiator bearing one or more halogens (e.g., $(X-(Sp^1)_n)_a$-L-halogen(s)) is employed in the preparation of compounds of formulas (Ia) through (Vb), L may bear an X group or protected form thereof. Alternatively, an initiator bearing one or more halogens may provide a L group with suitable functionalities (e.g., hydroxyl, amine, or carboxyl or protected forms thereof) that may be used to introduce an -$(Sp^1)_n$-X group through the use of a bifunctional agent (See, for example Schemes IB and IIB).

A broad variety of initiators may be used to prepare compounds of the invention, including a number of initiators set forth in U.S. Pat. No. 6,852,816. In some embodiments, the initiators employed for ATRP reactions to prepare compounds of the invention are selected from alkanes, cycloalkanes, alkyl carboxylic acids or esters thereof, cycloalkylcarboxylic acids or esters thereof, ethers and cyclic alkyl ethers bearing one halogen where unbranched compounds are prepared, and more than one halogen where branched molecules are prepared. In other embodiments the initiators are selected from alkanes, cycloalkanes, alkyl carboxylic acids or esters thereof, cycloalkylcarboxylic acids or esters thereof, ethers and cyclic alkyl ethers bearing one chlorine or bromine atom where unbranched compounds are to be prepared, or alternatively, more than one chlorine and or bromine where branched molecules are to be prepared.

Initiators employed for ATRP reactions may be hydroxylated. In some embodiments, the initiators employed for ATRP reactions to prepare compounds of the invention are selected from alkanes, cycloalkanes, alkyl carboxylic acids or esters thereof, cycloalkylcarboxylic acids or esters thereof, ethers and cyclic alkyl ethers bearing a hydroxyl group and also bearing one halogen where unbranched compounds are to be prepared, or alternatively, more than one halogen where branched molecules are to be prepared. In other embodiments the initiators are selected from alkanes, cycloalkanes, alkyl carboxylic acids or esters thereof, cycloalkylcarboxylic acids or esters thereof, ethers and cyclic alkyl ethers bearing a hydroxyl group and also bearing one chlorine or bromine atom where unbranched compounds are to be prepared, or alternatively, more than one chlorine and or bromine where branched molecules are to be prepared. In another embodiment where forked compounds of the invention are to be prepared, the initiators are dihydroxy or trihydroxy, or even polyhydroxy alkanes, cycloalkanes, alkyl carboxylic acids or esters thereof, cycloalkylcarboxylic acids or esters thereof, ethers and cyclic alkyl ethers also bearing one chlorine or bromine atom where unbranched compounds are to be prepared, or alternatively, more than one chlorine and or bromine where branched and forked compounds are to be prepared. Where the initiators are hydroxylated, following the polymerization reaction to append the polymeric portion of the molecule the hydroxyl group or groups may function as the reactive group "X" of compounds of formulas (Ia), (IIa), (IIIa), (IVa) or (Va). Alternatively, following polymerization the hydroxyl group or groups may be reacted with hydroxyl reactive bifunctional agents such as those set forth in Table II (e.g., N-(p-maleimidophenyl)isocyanate) to prepare a compound of formula (Ia), (IIa), (IIIa), (IVa) or (Va) with other reactive groups.

Initiators employed for ATRP reactions may bear one or more amine groups. In some embodiments, the initiators employed for ATRP reactions to prepare compounds of the invention are alkanes, cycloalkanes, alkyl carboxylic acids or esters thereof, cycloalkylcarboxylic acids or esters thereof, ethers and cyclic alkyl ethers bearing an amine group and also bearing one halogen where unbranched compounds are to be prepared, or alternatively, more than one halogen where branched molecules are to be prepared. In other embodiments, the initiators are alkanes, cycloalkanes, alkyl carboxylic acids or esters thereof, cycloalkylcarboxylic acids or esters thereof, ethers and cyclic alkyl ethers bearing an amine and also bearing one chlorine or bromine atom where unbranched compounds are to be prepared, or alternatively, more than one chlorine and or bromine where branched molecules are to be prepared. In another embodiment where forked compounds of the invention are to be prepared, the initiators are diamino or triamino, or even polyamino alkanes, cycloalkanes, alkyl carboxylic acids or esters thereof, cycloalkylcarboxylic acids or esters thereof, ethers and cyclic alkyl ethers also bearing one chlorine or bromine atom where unbranched compounds are to be prepared, or alternatively, more than one chlorine and or bromine where branched and forked compounds are to be prepared. Where the initiators bear one or more amine groups, following the polymerization reaction to append the polymeric portion of the molecule the amine group or groups may function as the reactive group "X" of compounds of formulas (Ia), (IIa), (IIIa), (IVa) or (Va). Alternatively, following polymerization the amine group or groups may be reacted with amine reactive bifunctional agents such as those set forth in Table II (e.g., 3,340-dithiobis(sulfosuccinimidyl-propionate), sulfosuccinimidyl 4-(p-maleimidophenyl)butyrate, N-(ε-trifluoracetylcaproyloxy)succinimide ester, β-(tris[hydroxymethyl]phosphine)propionic acid etc.) to prepare additional compounds of formulas (Ia), (IIa), (IIIa), (IVa) or (Va).

Chlorinated or brominated alkylcarboxylic acids, including alkyl dicarboxylic acids, substituted with amino or hydroxy groups may also be employed as initiators. In some embodiments of the invention where ATRP is employed to prepare compounds of formulas (Ia) through (Vb), the initiators may be alkylcarboxylic acids bearing one or more halogens selected from chlorine and bromine. In some embodiments, where forked compounds are to be prepared, the initiators may be alkylcarboxylic acids bearing two or more carboxyl groups and a halogen selected from chlorine and bromine and two or more groups selected from —OH and —NH$_2$. In embodiments where branched compounds are to be prepared, the initiators may be alkylcarboxylic acids bearing two or more halogens selected from chlorine and bromine. In embodiments where branched and forked compounds are to be prepared, the initiators may be alkylcarboxylic acids bearing two or more halogens selected from chlorine and bromine and two or more carboxyl groups. Where the initiators bear one or more carboxyl groups, following the polymerization reaction to append the polymeric portion of the molecule the carboxyl group or groups may function as the reactive group "X" of compounds of formulas (Ia), (IIa), (IIIa), (IVa) or (Va). Alternatively, following polymerization the carboxyl group or groups may be reacted with carboxyl reactive bifunctional agents such as those set forth in Table II (e.g., N-(s-Trifluoracetylcaproyloxy)succinimide ester, 3-([2-Aminoethyl])dithio)-propionic acid-HCl etc.) to prepare additional compounds of formulas (Ia), (IIa), (IIIa), (IVa) or (Va).

Chlorinated or brominated alkanes substituted with two or more groups selected from —COOH, —OH and —NH$_2$ may also be employed as initiators for the preparation of forked compounds where ATRP is employed to prepare compounds of formulas (Ia) through (Vb). The initiators may be alkanes bearing one halogen selected from chlorine and bromine and two or more groups selected from —COOH, —OH and —NH$_2$. In some embodiments where branched and forked compounds are to be prepared, the initiators may be alkanes bearing two or more halogens selected from chlorine and bromine and two or more groups selected from —COOH, —OH and —NH$_2$. Where the initiators bear two or more groups selected from —COOH, —OH and —NH$_2$, following the polymerization reaction to append the polymeric portion of the molecule the —COOH, —OH and —NH$_2$ groups present may function as the reactive X groups of compounds of formulas (Ia), (IIa), (IIIa), (IVa) or (Va). Alternatively, following polymerization the —COOH, —OH and —NH$_2$ groups may be reacted with —COOH, —OH or —NH$_2$ reactive bifunctional agents such as those set forth in Table II to prepare additional compounds of formulas (Ia), (IIa), (IIIa), (IVa) or (Va). In this manner asymmetric forked compounds of formulas (Ia), (IIa), (IIIa), (IVa) or (Va) may be prepared, especially where two different groups selected from —COOH, —OH and —NH$_2$ are present in the initiator; subsequent reaction with one or more biologically active agent will yield asymmetric forked compounds of formulas (IBM), (Ibis), (Iamb), (Ivy) or (Vb).

In addition to those groups present in initiators that are employed in the formation of polymer chains (e.g., Br or Cl) and those that serve to link X or X-Sp$^1$ moieties, imitators may also contain one or more independently selected —OH, amino, monoalkylamino, dialkylamino, —O-alkyl, —COOH, —COO-alkyl, or phosphate groups (or protected forms thereof) that will be present as substituents on the L group of compounds of formulas (Ia) through (Vb).

A broad variety of initiators are commercially available, for example: 3-bromopropionaldehyde dimethyl acetal; 3-bromopropanamine; 3-bromopropionic acid; 4 bromobutanoic acid; 2,3-dibromopropionic acid and its methyl ester; 2,3-dichloropropionic acid and its methoxy ester; 2,3-dichloropropionamide; 2,2,3-trichloropropionamide; 2,3-dibromo-1-propanol; 1,3-dibromo-2-propanol; 1,3-dibromo-2-propanamine; 3-bromo-2-(bromomethyl)propanoic acid; 2,2,3-trichloro-1-hydroxybutylformamide; 2,2,3,3,3-pentachloropropionamide; (2,2,3-trichloro-1-hydroxybutyl)-carbamic acid methyl ester; 2,3-dibromosuccinic acid; 3,4-dibromodihydro-2,5-furandione; methyl 2,3-dibromo-2-methylpropanoate; 2,3-dibromo-4-oxobutanoic acid; ethyl 2,3-dibromo-2-methylpropanoate; 2,3-dibromo-N,N-bis(hydroxymethyl)propanamide; 3,4-dibromo-4-phenyl-2-butanone; 2,3-dibromo-3-phenylpropanoic acid; 2,3,4-tribromobutanoic acid; 4,5-dibromo-1,2-cyclohexanedicarboxylic acid; 2,2-bis(bromomethyl)-1,3-propanediol; 3,5-dibromo-4-oxopentanoic acid; and bromoacetic acid N-hydroxysuccinimide ester available from Sigma-Aldrich (St. Louis, Mo.). Suitably protected forms of those initiators may be prepared using standard methods in the art as necessary.

E.3.1.2 Catalyst and Ligands

Catalyst for use in ATRP or group radical transfer polymerizations may include suitable salts of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo.^{3+}$, $W^{2+}$, $W^{3+}$, $Mn^{2+}$, $Mn^{2+}$, $Mn^{4+}$, $Rh^{3+}$, $Rh^{4+}$, $Re^{2+}$, $Re^{3+}$, $Co^{1+}$, $Co.^{2+}$, $Co^{3+}$, $V^{2+}$, $V^{3+}$, $Zn.^{1+}$, $Zn^{2+}$, $Ni^{2+}$, $Ni^{3+}$, $Au^{1+}$, $Au^{2+}$, $Ag^{1+}$ and $Ag^{2+}$. Suitable salts include, but are not limited to: halogen, $C_1$-$C_6$-alkoxy, sulfates, phosphate, triflate, hexafluorophosphate, methanesulphonate, arylsulphonate salts. In some embodiments the catalyst is a chloride, bromide salts of the above-recited metal ions. In other embodiments the catalyst is CuBr, CuCl or $RuCl_2$.

In some embodiments, the use of one or more ligands to solubilize transition metal catalyst is desirable. Suitable ligands are usefully used in combination with a variety of transition metal catalysts including where copper chloride or bromide, or ruthenium chloride transition metal salts are part of the catalyst. The choice of a ligand affects the function of catalyst as ligands not only aid in solubilizing transition metal catalysts in organic reaction media, but also adjust their redox potential. Selection of a ligand is also based upon the solubility and separability of the catalyst from the product mixture. Where polymerization is to be carried out in a liquid phase soluble ligands/catalyst are generally desirable although immobilized catalysts may be employed. Suitable ligands include those pyridyl groups (including alkyl pyridines e.g., 4.4. dialkyl-2,2' bipyridines) and pyridyl groups bearing an alkyl substituted imino group, where present, longer alkyl groups provide solubility in less polar monomer mixtures and solvent media. Triphenyl phosphines and other phosphorus ligands, in addition to indanyl, or cyclopentadienyl ligands, may also be employed with transition metal catalysts (e.g., $Ru^{+2}$-halide or $Fe^{+2}$-halide complexes with triphenylphosphine, indanyl or cyclopentadienyl ligands).

An approximately stoichiometric amount of metal compound and ligand in the catalyst, based on the molar ratios of the components when the metal ion is fully complexed, is employed in some embodiments. In other embodiments the ratio between metal compound and ligand is in the range 1:(0.5 to 2) or in the range 1:(0.8:1.25).

Generally, where the catalyst is copper, bidentate or multidentate nitrogen ligands produce more active catalysts. In addition, bridged or cyclic ligands and branched aliphatic polyamines provide more active catalysts than simple linear ligands. Where bromine is the counter ion, bidentate or one-half tetradentate ligands are needed per $Cu^{+1}$. Where more complex counter ions are employed, such as triflate or hexafluorophosphate, two bidentate or one tetradentate ligand may be employed. The addition of metallic copper may be advantageous in some embodiments particularly where faster polymerization is desired as metallic copper and $Cu^{+2}$ may undergo redox reaction to form $Cu^{+1}$. The addition of some $Cu^{+2}$ at the beginning of some ATRP reactions may be employed to decrease the amount of normal termination.

In some embodiments, the amount of catalyst employed in the polymerization reactions is the molar equivalent of the initiator that is present. Since catalyst is not consumed in the reaction, however, it is not essential to include a quantity of catalyst as high as of initiator. The ratio of catalyst to initiator, based on transition metal compound in some embodiments is from about 1:(1 to 50), and in other embodiments from about 1:(1 to 10).

E.3.1.3 Polymerization Conditions

In some embodiments, the living radical polymerization process of the invention is preferably carried out to achieve a degree of polymerization in the range of 3 to about 2000, and in other embodiments from about 5 to about 500. The degree of polymerization in other embodiments is in the range 10 to 100, or alternatively in the range of about 10 to about 50. The degree of polymerization in group or atom transfer radical polymerization technique, is directly related to the initial ratio of initiator to monomer. Therefore, in some embodiments the initial ratios of initiator to monomer are in the range of 1:(3 to about 2,000) or about 1:(5 to 500), or about 1:(10 to 100), or about 1:(10 to 50).

Polymerization reactions are typically carried out in the liquid phase, employing a single homogeneous solution. The reaction may, however, be heterogeneous comprising a solid and a liquid phase (e.g., a suspension or aqueous emulsion). In those embodiments where a non-polymerizable solvent is employed, the solvent employed is selected taking into consideration the nature of the zwitterionic monomer, the initiator, the catalyst and its ligand; and in addition, any comonomer that may be employed.

The solvent may comprise a single compound or a mixture of compounds. In some embodiments the solvent is water, and in other embodiments water is present in an amount from about 10% to about 100% by weight, based on the weight of the monomers present in the reaction. In those embodiments where a water insoluble comonomer is to be polymerized with a zwitterionic monomer, it may be desirable to employ a solvent or co-solvent (in conjunction with water) that permits solubilization of all the monomers present. Suitable organic solvents include, without limitation, formamides (e.g., dimethylformamide), ethers (e.g., tetrahydrofuran), esters (ethylacetate) and, most preferably, alcohols. In some embodiments where a mixture of water and organic solvent is to be employed, $C_1$-$C_4$ water miscible alkyl alcohols (methanol, ethanol propanol, isopropanol, butanol, isobutanol, and tert-butanol) are useful organic solvents. In other embodiments, water and methanol combinations are suitable for conducting polymerization reactions. The reaction may also be conducted in supercritical solvents such as $CO_2$.

As noted above, in some embodiments it is desirable to include water in the polymerization mixture in an amount from about 10% to about 100% by weight based on the weight of monomers to be polymerized. In other embodiments the total non-polymerizable solvent is from about 1% to about 500% by weight, based on the weight of the monomers present in the reaction mixture. In other embodiments, the total non-polymerizable solvent is from about 10% to about 500% by weight or alternatively from 20% to 400%, based on the weight of the monomers present in the reaction mixture.

In some embodiments, contact time of the zwitterionic monomer and water prior to contact with the initiator and catalyst are minimized by forming a premix comprising all components other than the zwitterionic monomer and for the zwitterionic monomer to be added to the premix last.

The polymerization reactions may be carried out at any suitable temperature. In some embodiments the temperature may be from about ambient (room temperature) to about 120° C. In other embodiments the polymerizations may be carried out at a temperature elevated from ambient temperature in the range of about 60° to 80° C. In other embodiments the reaction is carried out at ambient (room temperature).

In some embodiments, the compounds of the invention have a polydispersity (of molecular weight) of less than 1.5, as judged by gel permeation chromatography. In other embodiments the polydispersities may be in the range of 1.2 to 1.4. The polydispersity may be reduced by post polymerization reaction processing of compounds of formulas (Ia) through (Vb) (e.g., size selection on gel permeation chromatographic media). Alternatively, where the coupling of compounds of formulas (Ia), (IIa), (IIIa), (IVa), or (Va) to a biologically active agent is to be conducted to prepare the desired conjugates, the intermediate compounds having formulas (Ia), (IIa), (IIIa), (IVa), or (Va) may be size selected (e.g., by chromatography) prior to coupling to the biologically active agent.

The polymer moieties present in compounds of the invention, particularly those prepared by living radical polymerization, may be employed to form block copolymers where the product of the first polymerization is used as an initiator in a second group or atom transfer radical polymerization step carried out in the presence of a catalyst, and additional ethylenically unsaturated monomer(s). The product is a block copolymer of the A-B type, where the second block "B" may be comprised of monomoers of a different type than those employed in the initial block A. Alternatively, the monomers from which block A and block B are formed may comprise the same component monomers present in different ratios. More often they comprise different monomers, although they may include common comonomers. Additional blocks may be added to yield linear block copolymers having the sequence ABC or ABA. Block copolymer of the A-B-A type may also be produced by employing a difunctional initiator to which monomers of the B type may add. In the second polymerization, blocks of A monomers will add to the two ends of the B polymers that act as an initiator producing a polymer of the ABA type. Similarly, block copolymers having star or comb type architectures may be generated starting from multifunctional initiators used to prepare star or comb polymers described above. Where necessary, a different catalyst or solvent system may be employed to prepare the second or subsequent blocks of polymers.

E.3.1.4 Preparation of Compounds Having a Non-Halogenated Polymer Terminus

In those embodiments of compounds of formulas (Ia) through (Vb), where a halogen is appended the terminus of the polymeric group due to the use of a halogen containing initiator or catalyst in the polymerization reaction, it may be desirable to replace the halogen with another functionality. A variety of reactions may be employed for the conversion of the aliphatic halogen. In one embodiment the conversion of the aliphatic halogen may comprise an aliphatic nucleophilic substitution reaction. In one embodiment the aliphatic nucleophilic reaction is an isocyanato-de-halogenation and in another embodiment an isothiocyanato-de-halogenation. The resulting isocyanates or isothiocyanates can be converted to the corresponding amine by treatment with acid or base. As isothiocyanates can give S alkylation, and tend to require more vigorous conditions to convert them to the corresponding amine, isocyanates are preferred over isothiocyanates in the dehalogenation reactions. Where the aliphatic halide is treated with isocyanate in the presence of an alcohol, carbamates can be prepared directly.

A halogen appended to the terminus of the polymeric group may also be subject to nucleophilic substitution by a suitable nucleophile and converted into an alcohol, an alkyl ether (e.g., —O-methyl or —O-ethyl), an ester, a thioether and the like. Halogens may also be subject to an elimination reaction to give rise to an alkene (double bond).

In order to avoid affecting a biological agent coupled to a compound of formulas (Ib), (IIb), (IIIb), (IVb), or (Vb), the conversion of terminal aliphatic halogens may be conducted on compounds of formula (Ia), (IIa), (IIIa), (IVa), or (Va) prior to their coupling to a biologically active agent.

E.3.2 Coupling of Biologically Active Agents to Compounds of Formulas (Ia), (IIa), (IIIa), (IVa), or (Va).

The preparation of compounds (Ib), (IIb), (IIIb), (IVb), or (Vb), which comprise a biologically active agent, may be conducted by first linking the biologically active agent to a linking group and subjecting the coupled biologically active agent to conditions suitable for synthesis of the polymeric group of the molecule. In those cases, a suitable linking group can be an initiator (e.g., iodinated, brominated or chlorinated compound/group) for use in ATRP reactions. Such a reaction scheme is possible where the biologically active agent is compatible with the polymer polymerization reactions and any subsequent workup required. However, coupling of biologically active agents to compounds of formula (Ia), (IIa), (IIIa), (IVa), or (Va), may advantageously be used to prepare compounds of formulas (Ib), (IIb), (IIIb), (IVb), or (Vb), particularly where the biologically active agent is not compatible with conditions suitable for polymerization. In addition, where cost makes the loss of an agent to imperfect synthetic yields, encountered particularly in multistep synthetic reactions, coupling of biologically active agent to compounds of formulas (Ia), (IIa), (IIIa), (IVa), or (Va) may be advantageously employed.

Compounds of formulas (Ib), (IIb), (IIIb), (IVb), or (Vb) may be prepared by reaction with a compound of the formula (Ia), (IIa), (IIIa), (IVa), or (Va) with a biologically active agent. In those instances where compounds of formulas (Ia), (IIa), (IIIa), (IVa), or (Va) bear a -(Sp$^1$)$_n$-X group (see e.g., Scheme I part IA and Scheme II part IIA) where the X group is reactive the compounds may be reacted directly with a biologically active agent to prepare a molecule of formulas (Ib), (IIb), (IIIb), (IVb), or (Vb). Where the X group is present in a protected form, the molecule may be subjected to deprotection prior to reaction with a biologically active agent (e.g., protected carboxylic acids, hydroxyls, amines, carbonyls and the like from which X groups may be deprotected).

Where an -(Sp$^1$)$_n$-X group is not compatible with the conditions employed for polymerization reactions, it may be desirable to introduce the group subsequent to the polymerization reaction (see e.g., Scheme I part IB and Scheme II part IIB). Such a situation may arise where an X group contains a double bond that cannot be present in the polymerization reaction (e.g., X comprises a vinyl pyridine group, an alpha-beta unsaturated carbonyl, an alpha-beta ester, an alpha-beta unsaturated amide, or a malemide group). In such circumstances an initiator bearing one or more halogens may provide an L group with suitable functionalies (e.g., hydroxyl, amine, or carboxyl) for the attachment of -(Sp$^1$)$_n$-X moieties. In one such embodiment, a thio-reactive malemide group and a linker comprising an alkyl group terminated in a carboxyl may be linked to an L group bearing an aldehyde following polymerization by reaction with N-(β-maleimidopropionic acid)hydrazide-TFA (BMPH, available from Pierce Biotechnology).

As discussed above, biologically active agent A, of a compound of formula (Ib), (IIb), (IIIb), (IVb), or (Vb) may include a spacer group, denoted as (Sp$^2$)$_p$ where p is 0 or 1, appended to it as a means of linking the biologically active agent. Such linking groups may be introduced to provide not only a spacer group, but in addition, a group capable of reacting with an X group of a compound of formulas (Ia), (IIa), (IIIa), (IVa), or (Va)).

The introduction of Sp$^2$ spacer groups into biologically active molecules may occur prior to the reaction of the biologically active agent with a compound of formulas (Ia), (IIa), (IIIa), (IVa), or (Va). The incorporation of $Sp^2$ spacers into biologically active agents is particularly desirable where they may be used to introduce a uniquely reactive functionality that can be reacted with an X group to form the Z group of a compound of formulas (Ib), (IIb), (IIIb), (IVb), or (Vb).

Where it is desirable and the chemistry permits, $Sp^2$ linking groups may be linked to the X group of a compound of formulas (Ia), (IIa), (IIIa), (IVa), or (Va) prior to a reaction with the biologically active agent. Such a synthetic strategy may be employed in those embodiments where, for example, the biologically active agent is costly, or has a limited life due to susceptibility to degradation. In those cases, it is desirable that the final coupling between a $Sp^2$ spacer group that has been bound to an X functionality of compounds (Ia), (IIa), (IIIa), (IVa), or (Va) (i.e., to form a compound having —X converted to —Z-$Sp^2$) will be compatible with other functionalities present in the molecules, including the phosphorylcholine groups that are present in the polymer.

The coupling of biologically active agents to compounds of formulas (Ia), (IIa), (IIIa), (IVa), or (Va) may be conducted employing chemical conditions and reagents applicable to the reactions being conducted. Where, for example, the coupling requires the formation of an ester or an amide, dehydration reactions between a carboxylic acid and an alcohol or amine may employ a dehydrating agent (e.g., a carbodiimide such as dicyclohexylcarbodimide, DCC, or the water soluble agent 1-ethyl-3-(3-dimethyllaminopropyl)carbodiimide hydrochloride, EDC). Alternatively, N-hydroxysuccinimide esters (NHS) may be employed to prepare amides. Reaction to prepare amides employing NHS esters are typically conducted near neutral pH in phosphate, bicarbonate, borate, HEPES or other non-amine containing buffers at 4° to 25° C. In some embodiments, reactions employing EDC as a dehydrating agent, a pH of 4.5-7.5 may be employed; in other embodiments, a pH of 4.5 to 5 may be employed. Morpholinoethanesulfonic acid, MES, is an effective carbodiimide reaction buffer.

Thiol groups may be reacted under a variety of conditions to prepare different products. Where a thiol is reacted with a maleimide to form a thioether bond, the reaction is typically carried out at a pH of 6.5-7.5. Excess maleimide groups can be quenched by adding free thiol reagents such as mercaptoethanol. Where disulfide bonds are present as a linkage, they may be prepared by thiol-disulfide interchange between a sulfhydryl present in the biologically active group and an X functionality which is a disulfide such as a pyridyl disulfide. Reactions involving pyridyl disulfides may be conducted at pH 4-pH 5 and the reaction may be monitored at 343 nm to detect the released pyridine-2-thione. Thiol groups may also be reacted with epoxides in aqueous solution to yield hydroxy thioethers.

The reaction of guanido groups (e.g., those of an arginine in a protein or polypeptide of interest) with a glyoxal may be carried out at pH7.0-8.0. The reaction typically proceeds at 25° C. The derivative, which contains two phenylglyoxal moieties per guanido group, is more stable under mildly acidic conditions (below pH 4) than at neutral or alkaline pHs, and permits isolation of the linked materials. At neutral or alkaline pH values, the linkage decomposes slowly. Where an arginine residue of a protein or polypeptide is reacted with a phenylglyoxal reagent, about 80% of the linkage will hydrolyze to regenerate the original arginine residue (in the absence of excess reagent) in approximately 48 hours at 37° at about pH 7.

Imidoester reactions with amines are typically conducted at pH of 8-10, and preferably at about pH 10. The amidine linkage formed from the reaction of an imidoester with an amine is reversible, particularly at high pH.

Haloacetals may be reacted with sulfhydryl groups over a broad pH range. To avoid side reactions between histidine residues that may be present, particularly where the sulfhydryl group is present on a protein or polypepetide, the reaction may be conducted at about pH 8.3.

Aldehydes may be reacted with amines under a variety of conditions to form imines. Where either the aldehyde or the amine is immediately adjacent to an aryl group the product is a Schiff base that tends to be more stable than where no aryl group is present. Conditions for the reaction of amines with aldehydes to form an imine bond include the use of a basic pH from about pH 9 to about pH 11 and a temperature from about 0° C. to room temperature, over 1 to 24 hours. Buffers including borohydride and tertiary amine containing buffers are often employed for the preparation of imines. Where it is desired imine conjugates, which are hydrolytically susceptible, may be reduced to form an amine bond which is not hydrolytically susceptible. Reduction may be conducted with a variety of suitable reducing agents including sodium borohydride or sodium cyanoborohydride.

The reaction conditions provided above are intended to provide general guidance to the artisan. The skilled artisan will recognize that reaction conditions may be varied as necessary to promote the formation of conjugates of formulas (Ib), (IIb), (IIIb), (IVb), or (Vb) and that guidance for modification of the reactions may be obtained from standard texts in organic chemistry. Additional guidance may be obtained from texts such as Wong, S. S., "Chemistry of Protein Conjugation and Cross-Linking," (CRC Press 1991), which discuss related chemical reactions.

E.4 Alternatives to Living Radical Polymerization Methods for the Preparation of Compounds of the Invention In addition to the use of the living radical polymerization methods described above, compounds of the present invention may also be prepared by diverse methods including the preparation of the polyacrylic acid polymer portions of the compounds to form polymer intermediates via any method known in the art. Suitable methods include free radical methods of polymerization that may be initiated by methods including thermal, hydrolytic, redox, or photochemical means. The polymer intermediates may be selected for size by chromatographic methods if necessary, and coupled to a reactive group (i.e., an X group) via any group capable of contributing an L group (and a $Sp^1$ spacer if present) bearing a reactive group, or a protected form thereof, to form a compound of formula (Ia) (IIa), (IIIa), (IVa), or (Va). Following any necessary deprotection or activation of the X group, compounds of formulas (Ib) (IIb), (IIIb), (IVb), or (Vb) may be prepared by reaction with a biologically active agent under suitable conditions. This method of preparation is illustrated in Scheme III for monomers "M" and 4-formylbenzoic acid, which provides a means (the carboxyl group) for coupling the polymer intermediate and a reactive group (the aldehyde) for reaction with an amine bearing biologically active agent.

Scheme III

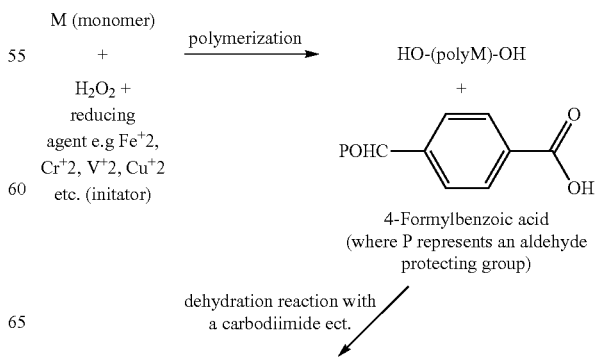

M (monomer)
+
$H_2O_2$ +
reducing agent e.g $Fe^{+2}$, $Cr^{+2}$, $V^{+2}$, $Cu^{+2}$ etc. (initator)

polymerization → HO-(polyM)-OH

+

POHC—⟨benzene⟩—C(=O)OH

4-Formylbenzoic acid
(where P represents an aldehyde protecting group)

dehydration reaction with a carbodiimide ect.

-continued

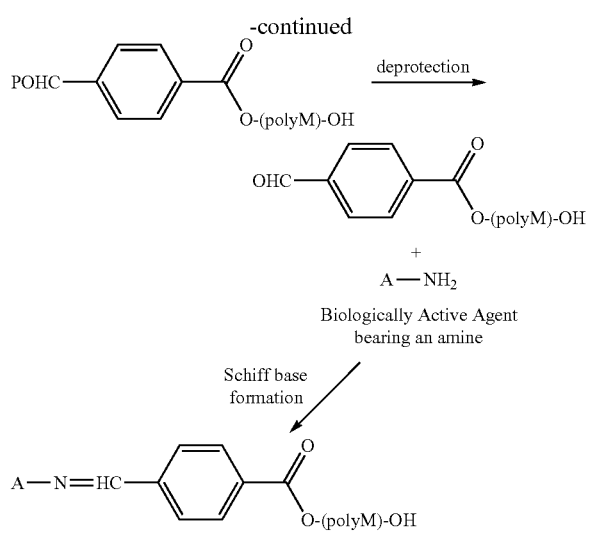

The imine product prepared in Scheme III may be reduced to yield an amine through the use of suitable reducing agents such as sodium cyanoborohydride.

E.5 Purification and Molecular Weight Determination.

Where it is desirable, compounds of formulas (Ia) through (Vb) may be purified by any known means including precipitation, dialysis and chromatography. One convenient means of removing small molecule contaminants such as catalysts, ligands, unpolymerized monomers, or small molecule biological active agents from the desired polymer materials is passage of the product over a column of desalting gel equilibrated with a suitable buffer (e.g., Bio-Gel P6DG available from Bio-Rad Laboratories, Inc., Hercules Calif., which can be used with conjugates over 6,000 Daltons).

Chromatography on media capable of resolving the materials having a molecular weight in the range of the polymeric materials and polymer conjugates of formulas (Ia) through (Vb) may also be conducted, particularly where it is desirable to determine the polydispersity of the polymer conjugate. Any conventional chromatographic media capable of resolving materials in the desired molecular weight range may be employed including Superdex, Sephacryl, Sephadex and Sepharose. The specific choice of media (e.g., Superdex peptide, Superdex 75 or Superdex 200) will be affected by the size of the conjugate that needs to be resolved. Chromatography may be conducted employing standard column chromatographic methods, Fast Protein Liquid Chromatography (FPLC), or HPLC. While chromatography at room temperature is possible in many instances, chromatography at lower temperatures (e.g., 4° C.) is often desirable. Any suitable buffer may be employed in the chromatographic separation of the polymer conjugates. Chromatography in a mobile phase that is also a pharmaceutically acceptable excipient composition, including but not limited to normal saline (0.9 g of NaCl per 100 ml of water) or phosphate buffered saline (PBS), is also possible. Use of pharmaceutically acceptable excipients as the mobile phase has the advantage of avoiding the subsequent manipulations to exchange buffers present with the polymeric materials.

Other forms of chromatography, including but not limited to ion exchange chromatography and hydrophobic interaction chromatography, may also be employed.

The present invention is further illustrated by the following examples, which are provided by way of illustration and should not be construed as limiting the scope of the invention.

EXAMPLES

Example 1

Preparation of 2-Ethylacrylic Acid from Diethyl Malonate

Ethylacrylic acid was prepared from diethyl malonate by preparation of 2-carbethoxybutyric acid that was subsequently converted into 2-ethylacrylic acid (EAA).

2-Carboethoxybutyric Acid

Diethyl ethylmalonate was stirred overnight with 95% ethanol in the presence of 1M KOH. The white precipitate that forms was filtered out of solution, and the filtrate was concentrated under reduced pressure (e.g., on a rotary evaporator). The yellowish oil obtained upon concentration of the filtrate was added to the precipitate and the mixture was dissolved in a minimum amount of water. After acidification with dilute aqueous HCl to a pH of 2, an oil separates from the solution. The oil was taken up into diethyl ether and the aqueous layer was extracted three times with further with diethyl ether. The ether extracts were combined, dried over magnesium sulfate and filtered. A quantitative yield of 2-carboethoxybutyric acid was obtained as a yellowish oil.

2-Ethylacrylic Acid (ethyl 2-ethylacrylate)

The 2-carboethoxybutyric acid obtained in step (a) was cooled to −5° C. and diethylamine was added. A solution of formalin was added dropwise into the cooled reaction mixture which was then allowed to warm to room temperature. After stirring for 24 h the reaction mixture was warmed to 60° C. and stirred for 8 h more. The mixture consisted of two layers, which were cooled to 0° C. Concentrated sulfuric acid was added and the mixture is extracted with three 200 ml portions of diethyl ether. The ether extracts were combined, dried over magnesium sulfate and filtered. The ether was removed under reduced pressure to produce ethyl 2-ethylacrylate as a yellow oil.

Example 2

Preparation of 2-Methacryloyloxyethyl phosphorylcholine (HEMA-PC or MPC)

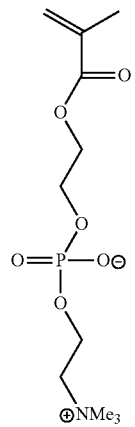

To a solution of 2-hydroxyethyl methacrylate (HEMA) (4.4 g, 40 mmol) in dry THF (40 mL) was added dry triethylamine (3.4 g, 40 mmol). This mixture was stirred at room temperature for 3 minutes, then cooled to −20° C. To the cooled solution was added COP (4.5 g, 40 mmol) as a solution in THF (20 mL) over a period of 1 hour. The temperature of the reaction mixture was maintained around −20° C. The white precipitate was filtered, and the remaining solution concentrated under reduced pressure to yield 6.7 g (71%) of 2-(2-oxo-1,3,2,dioxaphospholoyloxy)ethylmethacrylate (OPEMA) as pale yellow liquid. OPEMA (4.0 g, 16 mmol) was stirred in dry acetonitrile (30 mL) in a reaction bottle. The bottle was cooled to −20° C., and anhydrous trimethylamine (4 mL) was added rapidly to the solution. The bottle was closed quickly, and the mixture heated to 60° C. for 24 hours, then kept at −10° C. for 12 hours. MPC was observed as a white precipitate, collected by filtration, washed with cold acetonitrile, and dried under reduced pressure to give 1.5 g of product as a white powder. $^1$H NMR (300 MHz, CDCl$_3$): δ 1.93 (s, 3H), 3.40 (s, 9H), 3.80-3.85 (m, 2H), 4.09-4.11 (m, 2H), 4.30-4.36 (m, 4H), 5.84 (s, 1H), 6.11 (s, 1H) ppm.

Example 3

Preparation of 2-Bromo-2-methyl-propionic acid pyrrolidin-1-yl ester

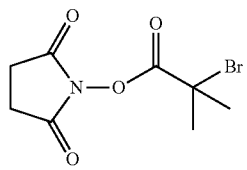

A solution of N-hydroxysuccinimide (NHS) (3.0 g, 26 mmol) in dry methylene chloride (300 mL) was stirred under an inert (argon or nitrogen) atmosphere. Triethylamine (7.3 mL, 52 mmol) was added, the mixture was cooled to 0° C., and 2-bromo-2-methylpropionyl bromide (3.9 mL, 31 mmol) was added dropwise over a period of 15 minutes. The mixture was stirred for 1 hour at 0° C., then warmed to room temperature and stirred overnight. Most of the solvent was removed by evaporation, and the remaining mixture was diluted with cold water (400 mL), and extracted with diethyl ether (3×30 mL), then washed with aqueous potassium carbonate (3×30 mL) and 1M HCl$_{(aq)}$ (3×30 mL). The organic layer was dried over anhydrous magnesium sulfate, then filtered and concentrated to give a brown solid. Crystallization from ethyl acetate gave the desired product as a white powder (2.62 g, 39%). $^1$H NMR (CDCl$_3$) δ (ppm) 2.09 (s, 6H, CH$_3$)$_2$Br), 2.88 (s, 4H, H$_{NHS}$); $^{13}$C NMR (CDCl$_3$) δ (ppm) 25.7 (C$_{NHS}$), 30.8 (C(CH$_3$)$_2$Br), 51.3 (C(CH$_3$)$_2$Br), 167.6 (C=O), 168.7 (C$_{NHS}$=O).

Example 4

Representative Polymerization of MPC using 2-Bromo-2-methyl-propionic acid pyrrolidin-1-yl ester from Example 3 and Atom Transfer Radical Polymerization (ATRP)

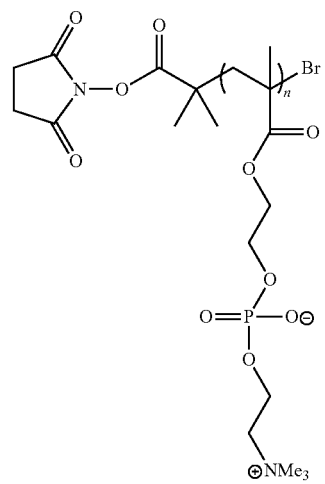

2-Bromo-2-methyl-propionic acid pyrrolidin-1-yl ester from Example 3 (13 mg, 0.050 mmol) was dissolved in degassed DMSO (1.5 mL). To this solution was added Cu$^1$Br (7 mg, 0.05) mmol) and 2,2'-bipyridine (15 mg, 0.10 mmol), followed by a solution of MPC (547 mg, 1.85 mmol) in degassed methanol (0.5 mL). The reaction mixture was subjected to three freeze-pump-thaw cycles, then was stirred under an inert (argon or nitrogen) atmosphere at room temperature for 18 hours, then at 40° C. for 4 hours. The mixture was passed through a short column of silica gel with methanol as eluent, to give a colorless solution. The solution was dried under vacuum to give the desired polymer (190 mg) as a white powder. $^1$H NMR (400 MHz, CD$_3$OD): δ 0.81-1.33 (br, 35H), 1.81-2.22 (br, 22H), 2.87 (s, 4H), 3.25 (s, 132H), 3.69-3.81 (br, 19H), 4.04-4.45 (br, 60H) ppm; $^{31}$P NMR (400 MHz, CD$_3$OD): −0.34 ppm. Gel permeation chromatography, against poly(ethylene oxide) calibration standards, eluting with 0.1 M aqueous NaNO$_3$ containing 0.2 weight percent NaN$_3$: M$_n$ 8,900, M$_p$ 9,600, M$_w$ 11,600, PDI 1.30. The following table provides examples of this polymerization performed under a variety of conditions.

NHS-terminated MPC polymers prepared under different conditions.

| Sample number | Solvent | Theoretical DP | Calcd M$_n$ | DP (NMR) | Mn (NMR) | Mn (GPC) | PDI (GPC) |
|---|---|---|---|---|---|---|---|
| I | MeOH | NHS-MPC$_{10}$ | 2960 | NHS-MPC$_8$ | 2,400 | 3,500 | 1.15 |
| II | DMSO | NHS-MPC$_{20}$ | 5920 | NHS-MPC$_{20}$ | 5,00 | 11,000 | 2.4 |
| III | MeOH-DMSO(1:1) | NHS-MPC$_{25}$ | 7400 | NHS-MPC$_{20}$ | 5,900 | 7,700 | 1.15 |
| IV | MeOH-DMSO(1:1) | NHS-MPC$_{25}$ | 7400 | NHS-MPC$_{15}$ | 4,400 | 5,400 | 1.25 |

| Sample number | Solvent | Theoretical DP | Calcd $M_n$ | DP (NMR) | Mn (NMR) | Mn (GPC) | PDI (GPC) |
|---|---|---|---|---|---|---|---|
| V | MeOH-DMSO(1:3) | NHS-MPC$_{37}$ | 10989 | NHS-MPC$_{28}$ | 8,200 | 9,600 | 1.30 |

DP = degree of polymerization (n monomer repeat units);
$M_n$ = number average molecular weight;
GPC = gel permeation chromatography;
PDI = polydispersity index, as defined by Mw/Mn, or weight average molecular weight divided by number average molecular weight (both determined by GPC).

Example 5

Preparation of 2-Bromo-2-methyl-propionic acid 4-formyl-phenyl ester

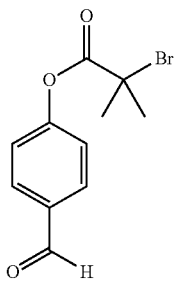

A solution of 4-hydroxy benzaldehyde (6.1 g, 0.050 mol) and triethylamine (6.1 g, 0.060 mol) was stirred in THF (200 mL) in a round-bottom flask. Bromoisobutyryl bromide (13.6 g, 0.060 mol) was added slowly to the stirring benzaldehyde solution, and the reaction mixture was stirred at room temperature for five hours. The white precipitate that appeared was removed by filtration, and the solvent was removed by rotary evaporation. Purification by column chromatography (eluting with 12% EtOAc in hexane) provided the desired aldehyde (6.5 g) as a white solid. $^1$H NMR (CDCl$_3$) δ=2.09 (s, 6H), 7.33 (d, J=7.2 Hz, 2H), 7.96 (d, J=7.99 Hz, 2H), 10.02 (s, 1H) ppm; $^{13}$C NMR (CDCl$_3$) δ (ppm) 30.4, 55.3, 121.5, 131.3, 134.2, 155.3, 169.6, 175.7, 190.9 ppm.

Example 6

MPC Polymerization Using Benzaldehyde Initiator and ATRP

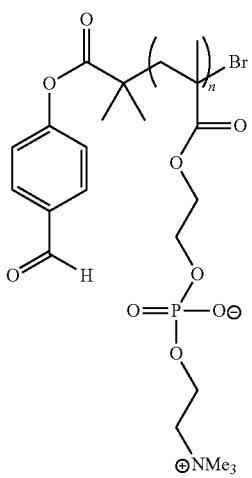

2-Bromo-2-methylpropionic acid 4-formyl-phenyl ester from Example 5 (10.8 mg, 40.0 mmol) was dissolved in degassed DMSO (1.0 mL). To this solution was added CuBr (7 mg, 0.05 mmol), 2,2'-bipyridine (15 mg, 0.10 mmol), and a solution of MPC (296 mg, 1.00 mmol) in degassed methanol (0.5 mL). The reaction mixture was subjected to three freeze-pump-thaw cycles, then stirred under nitrogen atmosphere for 18 hours at ambient temperature, and 4 hours at 40° C. The mixture was passed through a short column of silica gel, eluting with methanol, and washed with dry THF (2 mL) to give a colorless solution. The solution was dried under vacuum to give the desired polymer (100 mg) as a white powder. $^1$H NMR (300 MHz, CD$_3$OD): δ=0.61-1.42 (m, 236H), 1.90-2.33 (m, 131H),), 3.32 (s, 766H), 3.69-3.81 (brs, 140H), 3.95-4.43 (m, 438H), 7.27-7.46 (brs, 2H), 7.93-8.12 (brs, 2H), 9.95-10.11 (brs, 1H); GPC (eluent 0.1 M aqueous NaNO$_3$ containing 0.2 wt % NaN$_3$ and PEO as standard): $M_n$: 8,300; $M_p$: 9,000; $M_w$: 11,000; PDI 1.29.

Example 7

Preparation of 2-Bromo-2-methyl-propionic acid 3-(2-bromo-2-methyl-propionyloxy)-5-formyl-phenyl ester

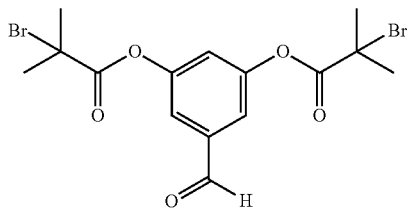 [SMILES: CC(C)(Br)C(=O)Oc1cc(C=O)cc(OC(=O)C(C)(C)Br)c1]

A solution of 3,5-dihydroxybenzaldehyde (1.38 g, 10.0 mmol) and triethylamine (2.5 g, 25 mmol) in dry THF (40 mL) was stirred at room temperature. Bromoisobutyryl bromide (5.7 g, 25 mmol) was added slowly to the stirring mixture, and the reaction was allowed to proceed at room temperature for 12 hours. A white precipitate formed, which was removed by filtration. Solvent was removed by rotary evaporation, and the desired compound was purified by column chromatography eluting with 15% EtOAc/hexanes to give 1.7 g (40%) of the desired difunctional initiator as pale yellow viscous liquid. $^1$H NMR (300 MHz, CDCl$_3$): δ=2.06 (s, 12H), 7.31 (t, J=2.5 Hz, 1H), 7.61 (d, J=2.5 Hz, 2H), 10.05 (s, 1H), $^{13}$C NMR (400 MHz, CDCl$_3$): δ=30.2, 54.7, 119.8, 120.9, 138.2, 151.2, 169.5, 189.8.

Example 8

MPC Polymerization Using Branched Benzaldehyde Initiator and ATRP

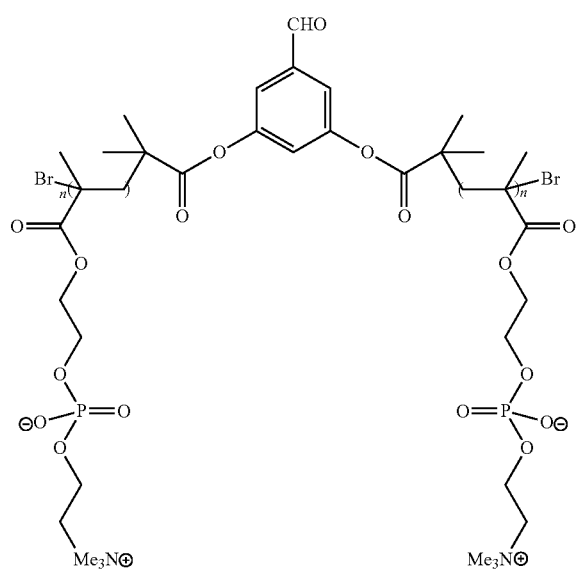

2-Bromo-2-methyl-propionic acid 3-(2-bromo-2-methyl-propionyloxy)-5-formyl-phenyl ester (25 mg, 0.060 mmol) from Example 7 was dissolved in degassed DMSO (1.5 mL). To this solution was added CuBr (14.3 mg, 0.100) mmol), 2,2'-bipyridine (30 mg, 0.20 mmol), and a solution of MPC (444 mg, 1.50 mmol) in degassed methanol (0.5 mL). The reaction mixture was subjected to three freeze-pump-thaw cycles, then stirred under nitrogen atmosphere for 18 hours at room temperature, and 4 hours at 40° C. The mixture was passed through a short column of silica gel, eluting with methanol, to give a colorless solution. The solution was dried under vacuum and washed with dry THF (2 mL) to give the desired polymer (250 mg) as a white powder. $^1$H NMR (400 MHz, CD$_3$OD): δ 0.52-1.54 (m, 254H), 1.85-2.49 (m, 143H),), 3.35 (s, 790H), 3.65-3.79 (brs, 148H), 4.15-4.43 (m, 474H), 7.27-7.46 (brs, 2H), 7.6-7.7 (brs, 1H), 9.90-10.1 (1H); GPC (polyethylene oxide standards, and eluting with 0.1 M aqueous NaNO$_3$ containing 0.2 wt % NaN$_3$): M$_n$: 9100; M$_p$: 10,000; M$_w$: 11,500; PDI 1.3.

Example 9

Preparation of 2-(2,2-dimethoxy-ethoxy)-ethanol

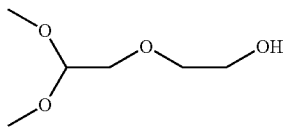

A solution of potassium hydroxide (5.0 g, 89 mmol) in ethylene glycol (12.5 mL, 224 mmol) was stirred at 115° C. in a round bottom flask. After the potassium hydroxide dissolved, chloroacetaldehyde dimethyl acetal (8.0 mL, 44 mmol) was added dropwise over 15 minutes, and the reaction mixture was stirred for 66 hours. The mixture was then allowed to cool to room temperature, and the whole diluted with water (40 mL), then extracted with methylene chloride (3×20 mL). The organic layer was washed with brine (3×20 mL), dried over magnesium sulfate, then concentrated to give the desired dimethyl acetal product as a very pale yellow liquid (2.2 g, 45%). $^1$H NMR (300 MHz, CDCl$_3$): δ=2.03 (s), 2.98 (s, 1H), 3.31 (s, 6H), 3.48 (t, 2H), 3.52 (t, 2H), 3.68 (t, 2H), 4.48 (q, 1H) $^{13}$C NMR (300 MHz, CDCl$_3$): δ=53.9, 61.5, 70.5, 72.9, 102.5.

Example 10

2-Bromo-2-methyl-propionic acid 2-(2,2-dimethoxy-ethoxy)-ethyl ester

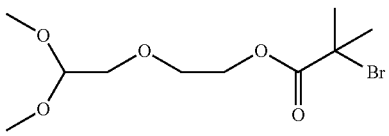 [SMILES: COC(COCCOC(=O)C(C)(C)Br)OC]

A solution of 2-(2,2-dimethoxy-ethoxy)-ethanol (2.20 g, 14.6 mmol) from Example 9 in dry triethylamine (3.0 mL, 21 mmol) and dry methylene chloride (30 mL) was stirred at 0° C. 2-bromo-2-methylpropionyl bromide (1.7 mL, 14 mmol) methylene chloride (10 mL) was then added to the alcohol over a 15 minute period. The reaction mixture was warmed to room temperature and stirred overnight. The reaction mixture was filtered, the filtrate was washed with saturated sodium bicarbonate, and dried with magnesium sulfate. The solvent was removed and the yellow oil purified by column chromatography. $^1$H NMR (300 MHz, CDCl$_3$): δ=1.78 (s, 6H), 3.31 (s, 6H), 3.49 (d, 2H), 3.68 (t, 2H), 4.25 (t, 2H), 4.46 (t, 1H) $^{13}$C NMR (300 MHz, CDCl$_3$): δ=31.23, 55.85, 56.15, 65.58, 69.55, 71.44, 103.09, 172.07.

Example 11

MPC Polymerization Using Protected Aliphatic Aldehyde Initiator and ATRP

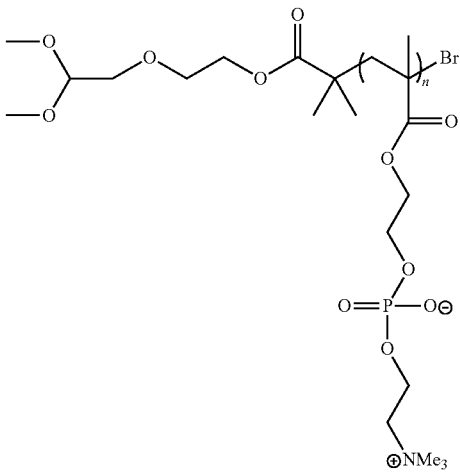

2-Bromo-2-methyl-propionic acid 2-(2,2-dimethoxy-ethoxy)-ethyl ester (16 mg, 0.080 mmol) from Example 10 was dissolved in degassed DMSO (2 mL). To this solution was added CuBr (12.5 mg, 0.088 mmol) and 2,2'-bipyridine (27 mg, 0.17 mmol), followed by a solution of MPC (592 mg, 2.00 mmol) in degassed methanol (0.5 mL). The reaction mixture was subjected to three freeze-pump-thaw cycles, then stirred under nitrogen atmosphere for 18 hours at room temperature, and 4 hours at 40° C. The mixture was passed through a short column of silica gel, eluting with methanol, to give a colorless solution. The solution was dried under vacuum and washed with dry THF (2 mL) to give the desired polymer (350 mg) as a white powder. GPC (polyethylene oxide standards, and eluting with 0.1 M aqueous NaNO$_3$ containing 0.2 wt % NaN$_3$). $^1$H NMR (400 MHz, CD$_3$OD): δ 0.81-1.33 (br), 1.70-2.22 (br), 3.31-3.49 (br), 3.67-3.84 (br), 4.04-4.45 (br) ppm; $M_n$: 11,200; $M_p$: 11,300; $M_w$: 15,600; PDI 1.4.

Example 12

Conjugation of Aldehyde Functionalized Polymer of Example 6 to G-CSF

The aldehyde functionalized polymer from Example 6 (6.3 mg) was dissolved in 40 mM sodium cyanoborohydride (2 mL) prepared in 100 mM sodium acetate buffer at pH 4.6. Purified granulocyte colony stimulating factor (G-CSF, 0.5 mL, FIG. 2) obtained from a transgenic chicken (for example, as disclosed in U.S. Pat. No. 6,730,822) in formulation buffer at a concentration of 0.265 mg/mL was added to 1.5 mL of the polymer and shaken at room temperature for 24 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 3 (1: conjugate; 2: G-CSF; 3: buffer)).

Example 13

Figure 4:
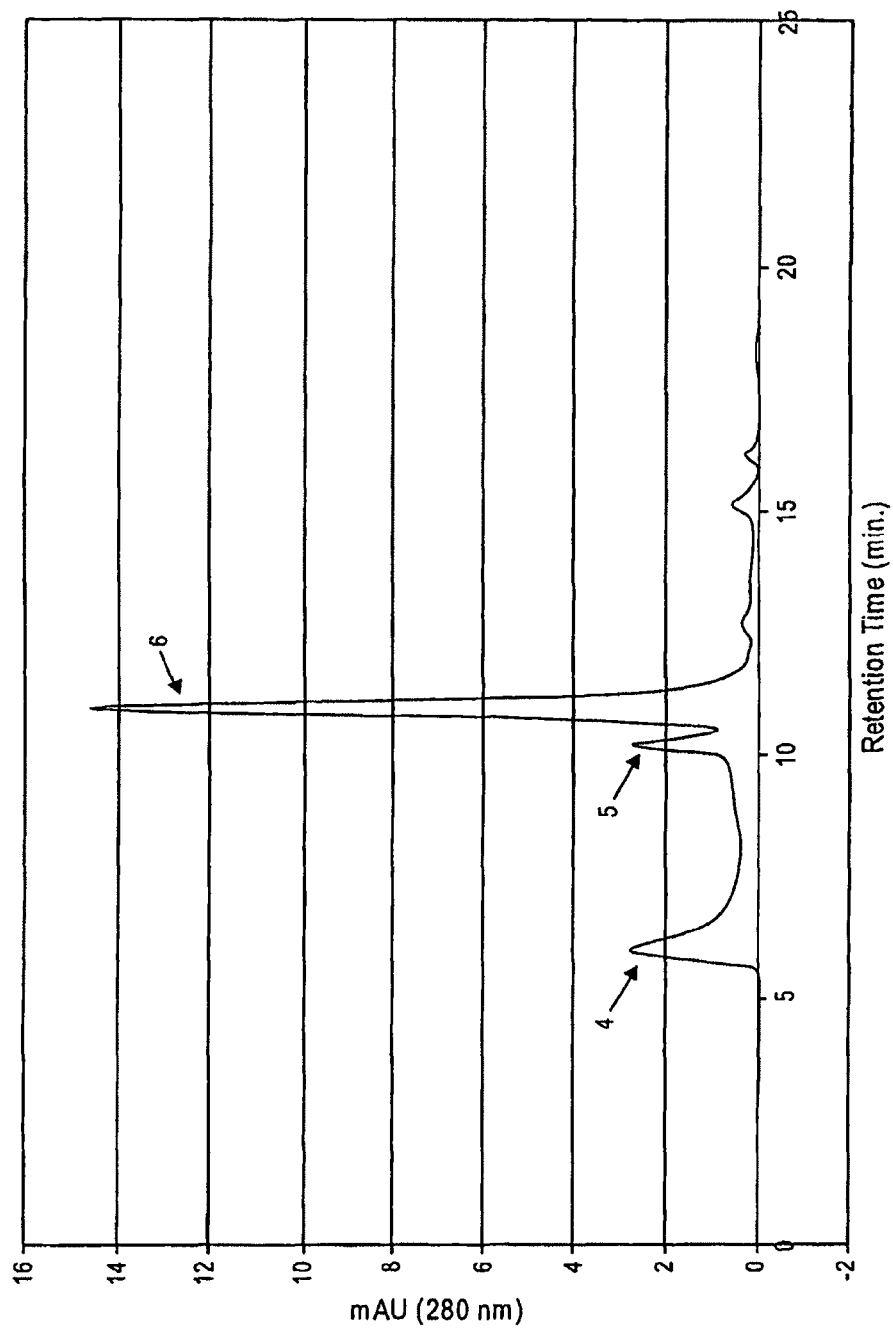

Alternative Conjugation of Aldehyde Functionalized Polymer of Example 6 to G-CSF The aldehyde functionalized polymer from Example 6 (6.3 mg) was dissolved in 40 mM sodium cyanoborohydride (2 mL) prepared in 100 mM sodium acetate buffer at pH 4.6. Granulocyte colony stimulating factor (G-CSF, 0.1 mL, FIG. 2) obtained from a transgenic chicken (for example, as disclosed in U.S. Pat. No. 6,730,822) in formulation buffer at a concentration of 0.265 mg/mL was added to 0.5 mL of the polymer and shaken at room temperature for 48 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 4 (4: conjugate; 5: G-CSF; 6: buffer)).

Example 14

Conjugation of Aldehyde Functionalized Polymer of Example 6 to EPO

Figure 5:
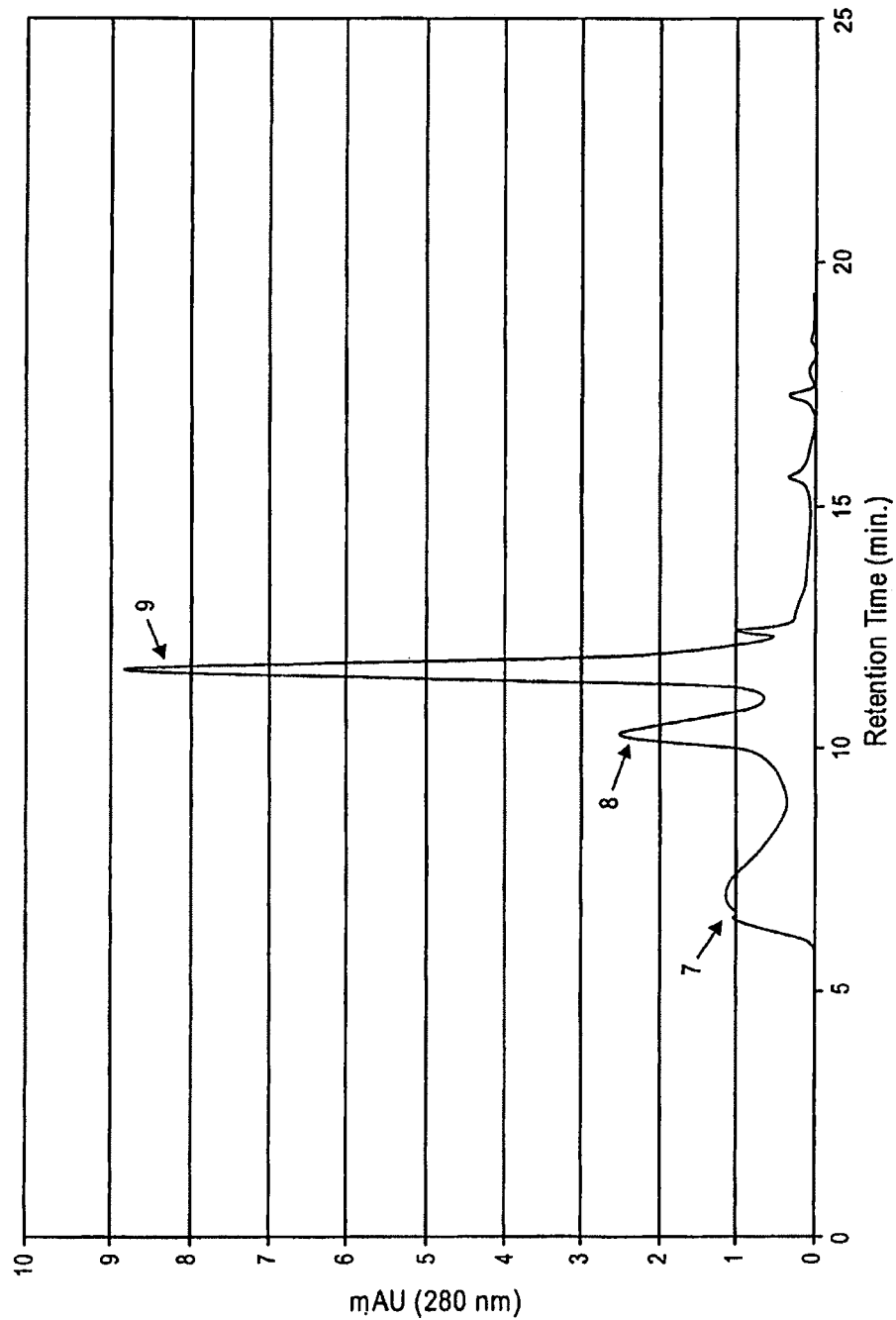
FIGS. 5, 6 and 7 show an HPLC chromatogram illustrating the conjugation of an aldehyde functionalized polymer of the invention to EPO.
Figure 6:
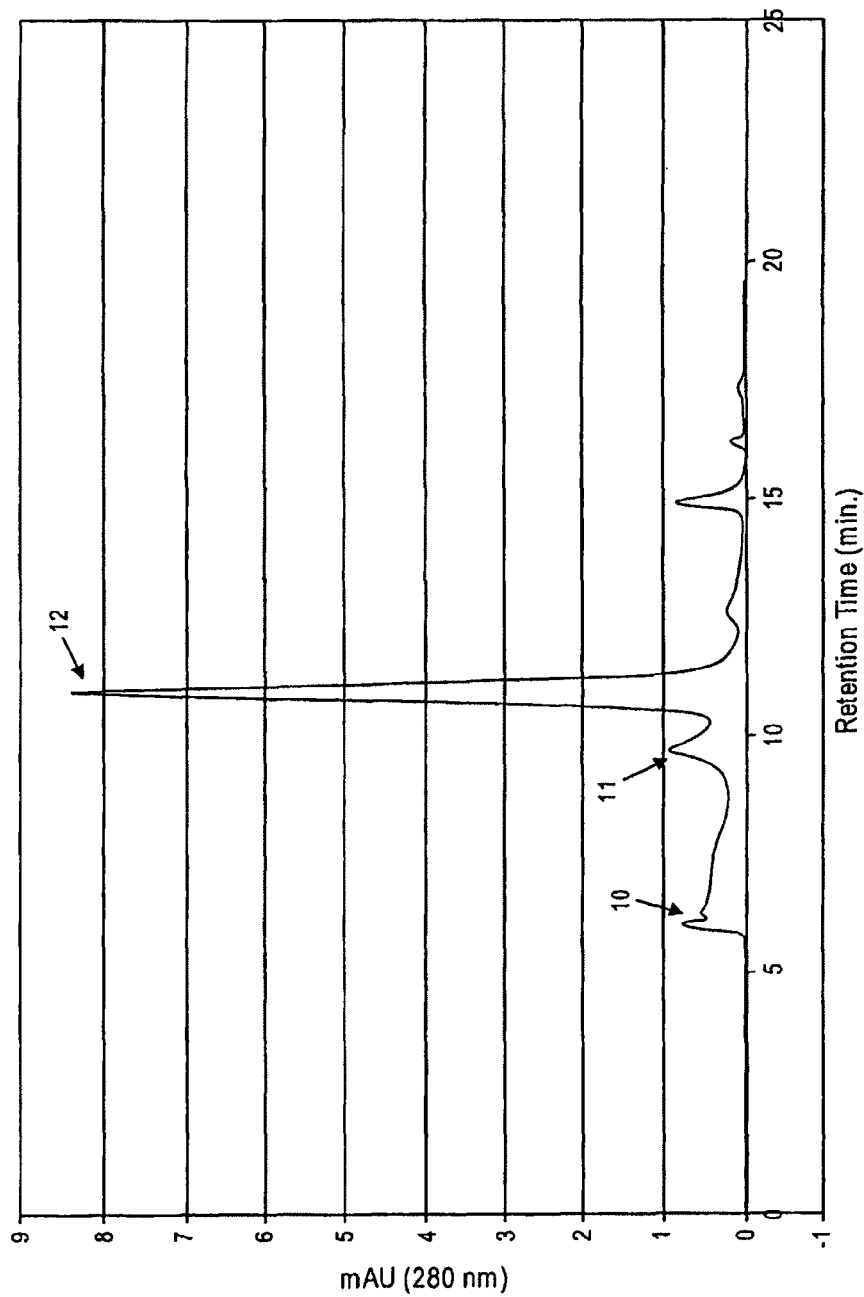
Figure 7:
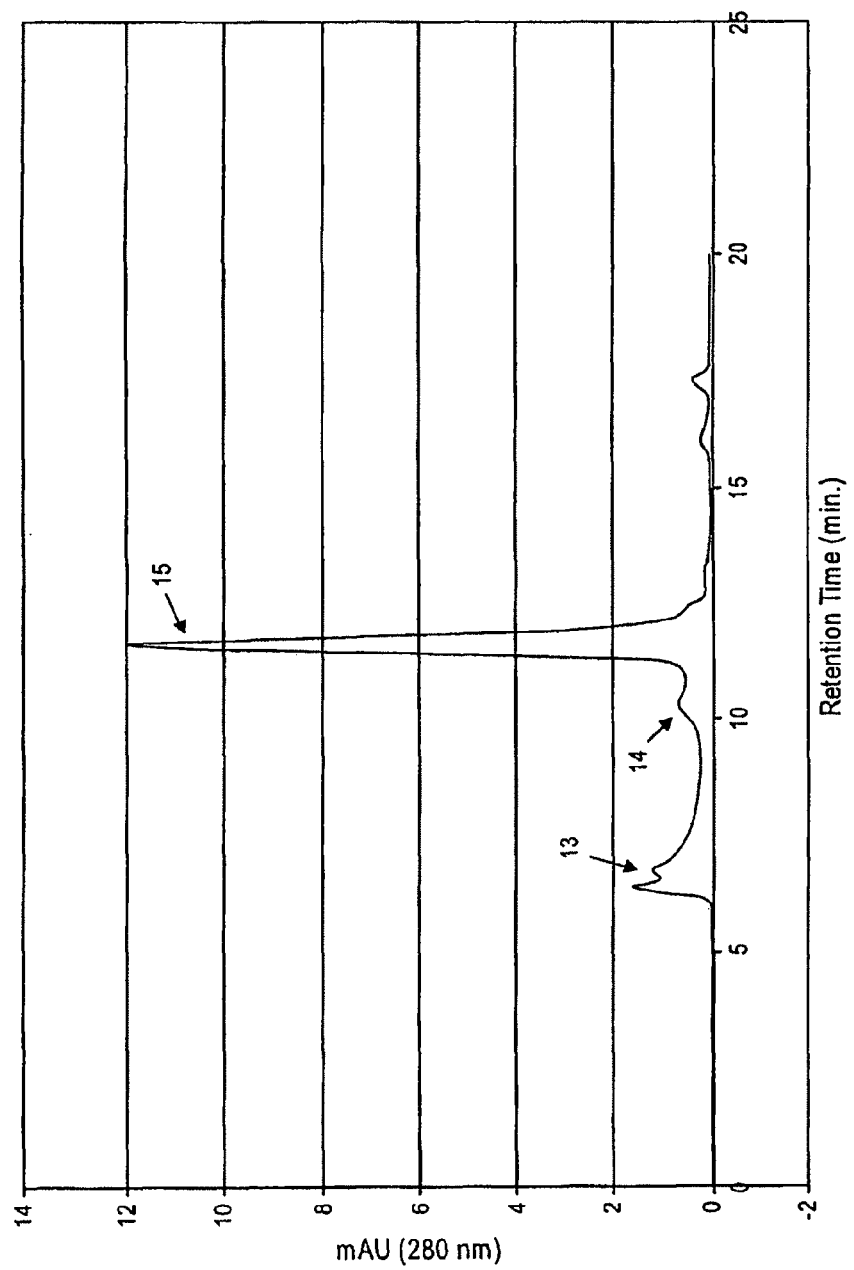

The aldehyde functionalized polymer from Example 6 (2.5 mg) was dissolved in 80 mM sodium cyanoborohydride (1 mL) prepared in 100 mM sodium acetate buffer at pH 4.6. Erythropoietin (EPO, 0.1 mL, FIG. 1) obtained from a transgenic chicken (for example, as disclosed in U.S. Pat. No. 6,730,822) in 100 mM sodium phosphate buffer (pH 6.98) at a concentration of 0.44 mg/mL was added to 0.5 mL of the polymer and shaken at room temperature for 72 hours. The resulting reaction mixture was analyzed on a Shodex KW-803 size exclusion column using a Beckman Coulter System Gold or Agilent 1100 series HPLC system at 280 nm with a flow rate of 1 mL/min. (after 24 hours, FIG. 5 (7: conjugate; 8: EPO; 9: buffer); after 48 hours, FIG. 6 (10: conjugate; 11: EPO; 12: buffer); and after 72 hours, FIG. 7 (13: conjugate; 14: EPO; 15: buffer)).

Example 15

Conjugation of NHS Functionalized Polymer of Example 4 to G-CSF

Figure 8:
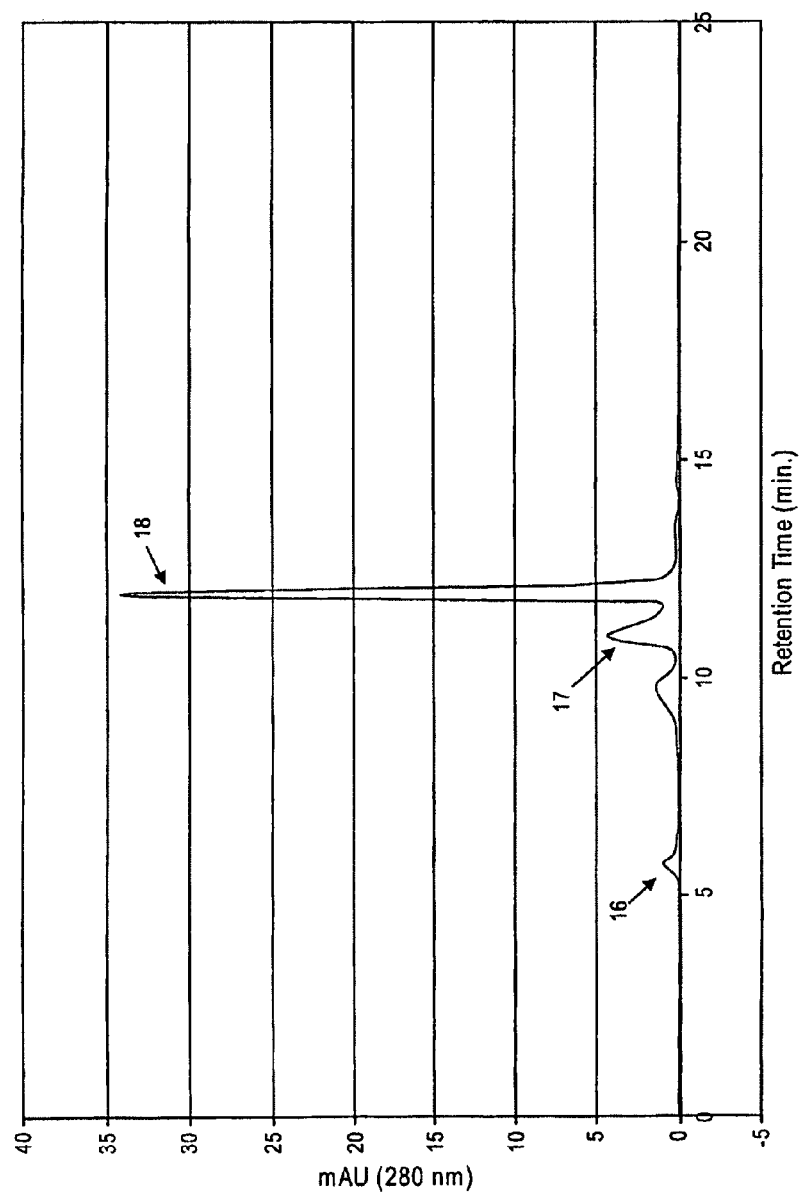
FIG. 8 shows an HPLC chromatogram illustrating the conjugation of a NHS functionalized polymer of the invention to G-CSF.

The NHS functionalized polymer from Example 4 (Sample I) (1.9 mg) was dissolved in G-CSF (0.1 mL, FIG. 2) obtained from a transgenic chicken (for example, as disclosed in U.S. Pat. No. 6,730,822) in 100 mM sodium borate buffer (pH 9.3) at a concentration of 0.265 mg/mL and shaken at room temperature for 24 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 8 (16: conjugate; 17: G-CSF; 18: buffer)).

Example 16

Conjugation of NHS Functionalized Polymer of Example 4 (Sample I) to EPO

Figure 9:
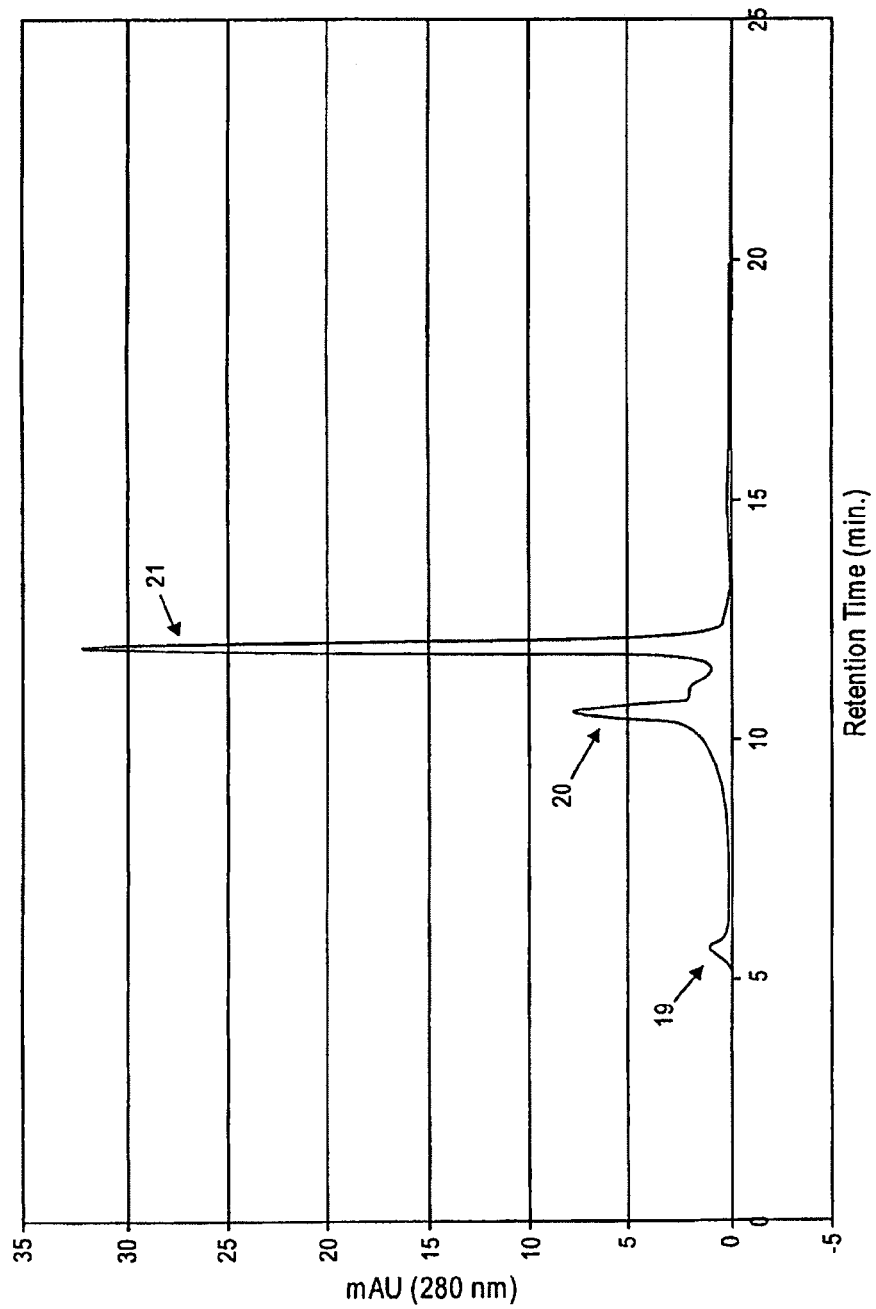
FIGS. 9 and 10 show an HPLC chromatogram illustrating the conjugation of a NHS functionalized polymer of the invention to EPO.
Figure 10:
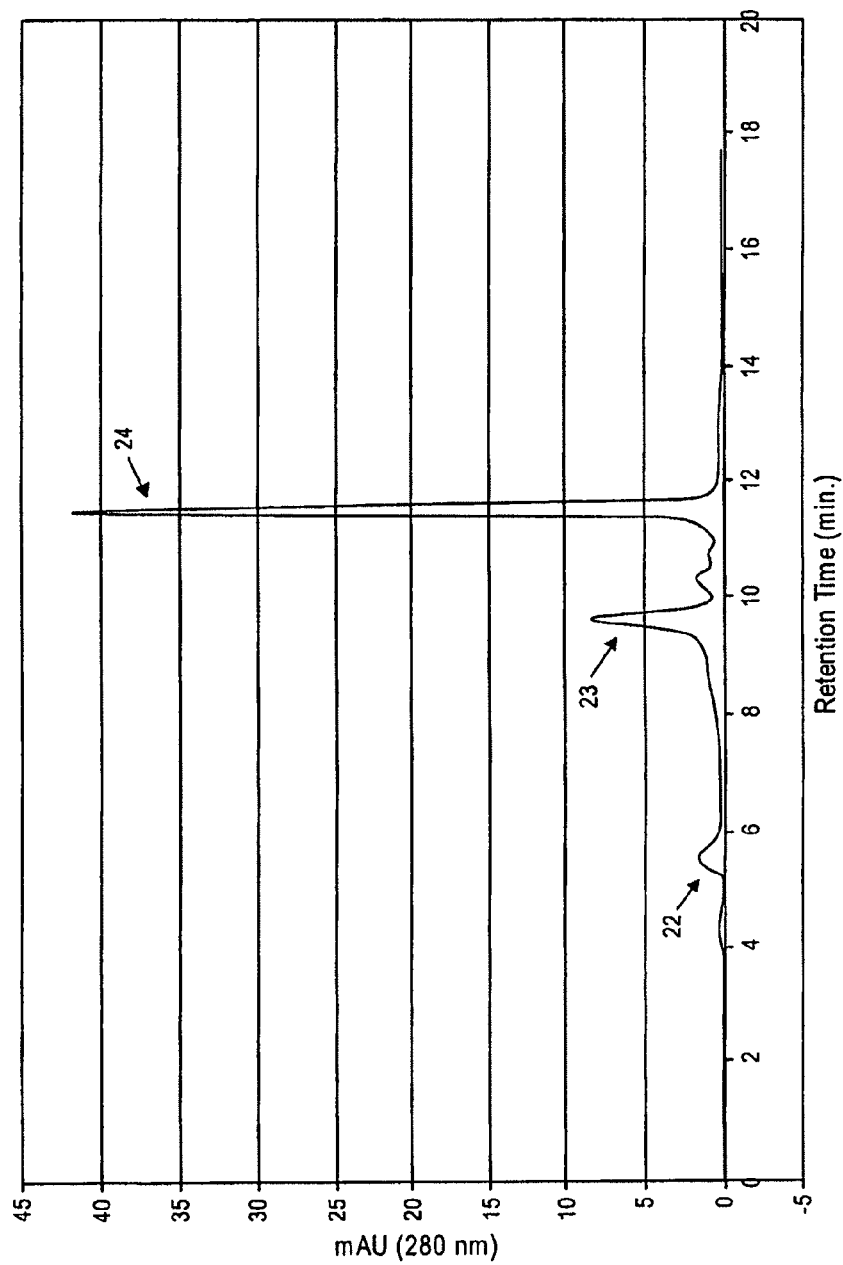

The NHS functionalized polymer from Example 4 (Sample 1) (2.1 mg) was dissolved in EPO (0.2 mL, FIG. 1) obtained from a transgenic chicken (for example, as disclosed in U.S. Pat. No. 6,730,822) in 100 mM sodium phosphate buffer (pH 8) at a concentration of 0.44 mg/mL mg/mL and shaken at room temperature for 72 hours. The resulting reaction mixture was analyzed on a Shodex KW-803 size exclusion column using a Beckman Coulter System Gold or Agilent 1100 series HPLC system at 280 nm with a flow rate of 1 mL/min. (after 24 hours, FIG. 9 (19: conjugate; 20: EPO; 21: buffer); and after 72 hours, FIG. 10 (22: conjugate; 23: EPO; 24: buffer)).

Example 17

Conjugation of NHS Functionalized Polymer of Example 4 to Interferon Alpha

Figure 11:
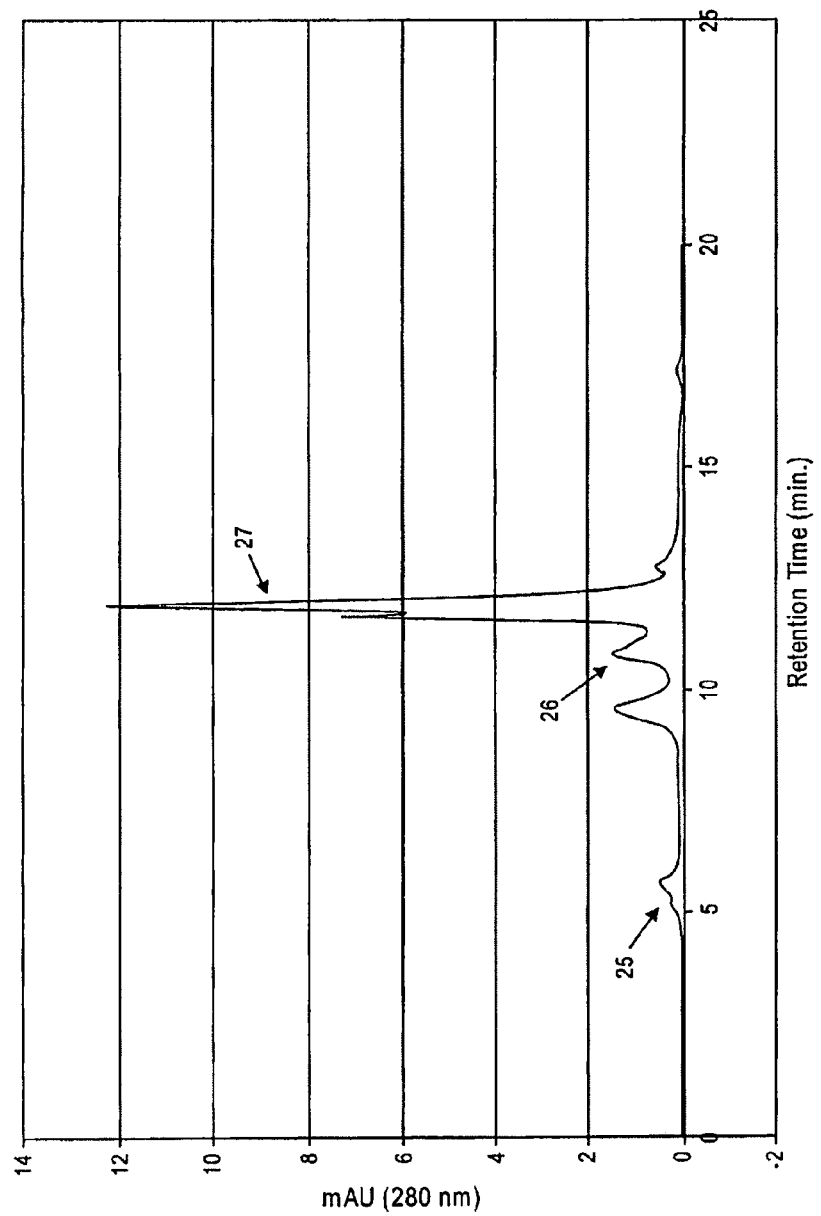
FIG. 11 shows an HPLC chromatogram illustrating the conjugation of a NHS functionalized polymer of the invention to Interferon alpha.

The NHS functionalized polymer from Example 4 (Sample I) (1.8 mg) was dissolved in Interferon alpha2b (0.2 mL) obtained from a transgenic chicken (for example, as disclosed in U.S. Pat. No. 6,730,822) in 100 mM sodium borate buffer (pH 9.3) at a concentration of 0.035 mg/mL and shaken at room temperature for 24 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 11 (25: conjugate; 26:interferon alpha; 27: buffer)).

Example 18

Alternative Conjugation of NHS Functionalized Polymer of Example 4 to G-CSF

Figure 12:
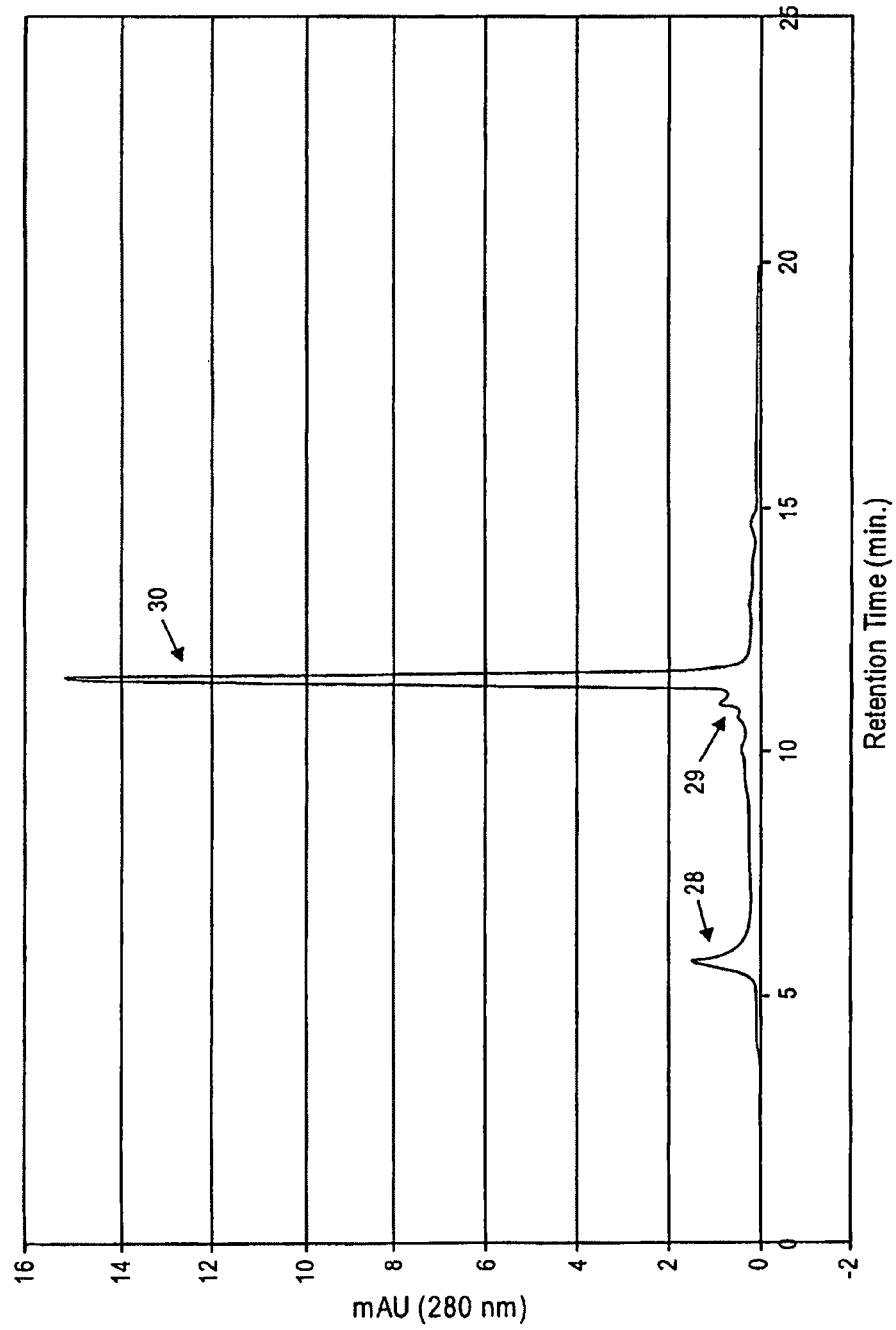
FIG. 12 shows an HPLC chromatogram illustrating the conjugation of a NHS functionalized polymer of the invention to G-CSF.

The NHS functionalized polymer from Example 4 (Sample V) (1.7 mg) was dissolved in G-CSF (0.3 mL, FIG. 2) obtained from a transgenic chicken (for example, as disclosed in U.S. Pat. No. 6,730,822) in 100 mM sodium borate buffer (pH 9.3) at a concentration of 0.265 mg/mL and shaken at room temperature for 72 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 12 (28: conjugate; 29: G-CSF; 30: buffer)).

Example 19

Conjugation of NHS Functionalized Polymer of Example 4 to Somatostatin

Figure 13:
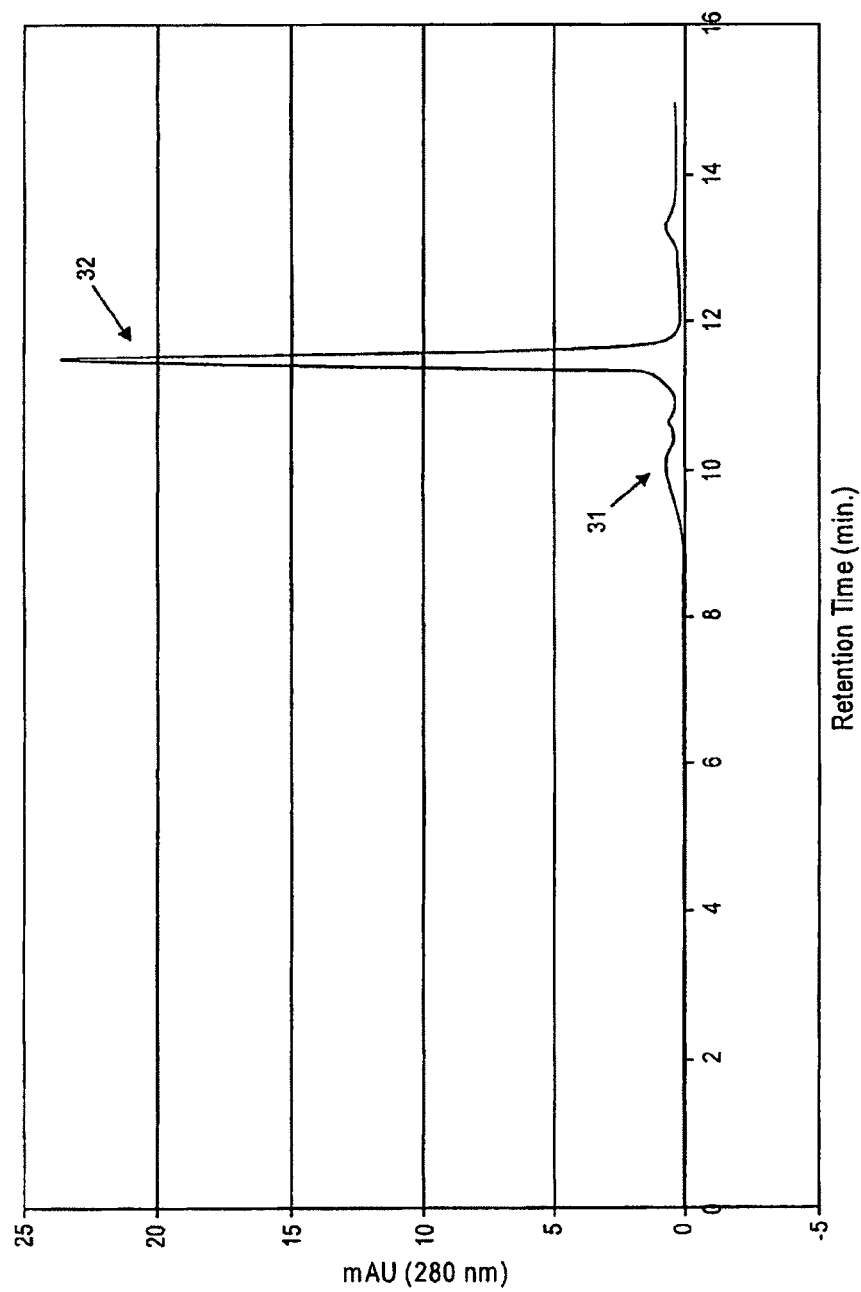
FIG. 13 shows an HPLC chromatogram illustrating the conjugation of a NHS functionalized polymer of the invention to somatostatin.

Somatostatin (1.1 mg) obtained from Sigma Aldrich was dissolved in phosphate buffered saline (pH 7.2; 1 mL). The NHS functionalized polymer from Example 4 (Sample IV) (2 mg) was dissolved in a solution containing 100 mM sodium borate buffer (pH 9.3; 0.2 mL) and the somatostatin solution (0.1 mL) and shaken at room temperature for 72 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 13 (31: conjugate; 32: somatostatin)).

Example 20

Conjugation of Aldehyde Functionalized Branched Polymer of Example 8 to EPO

Figure 14:
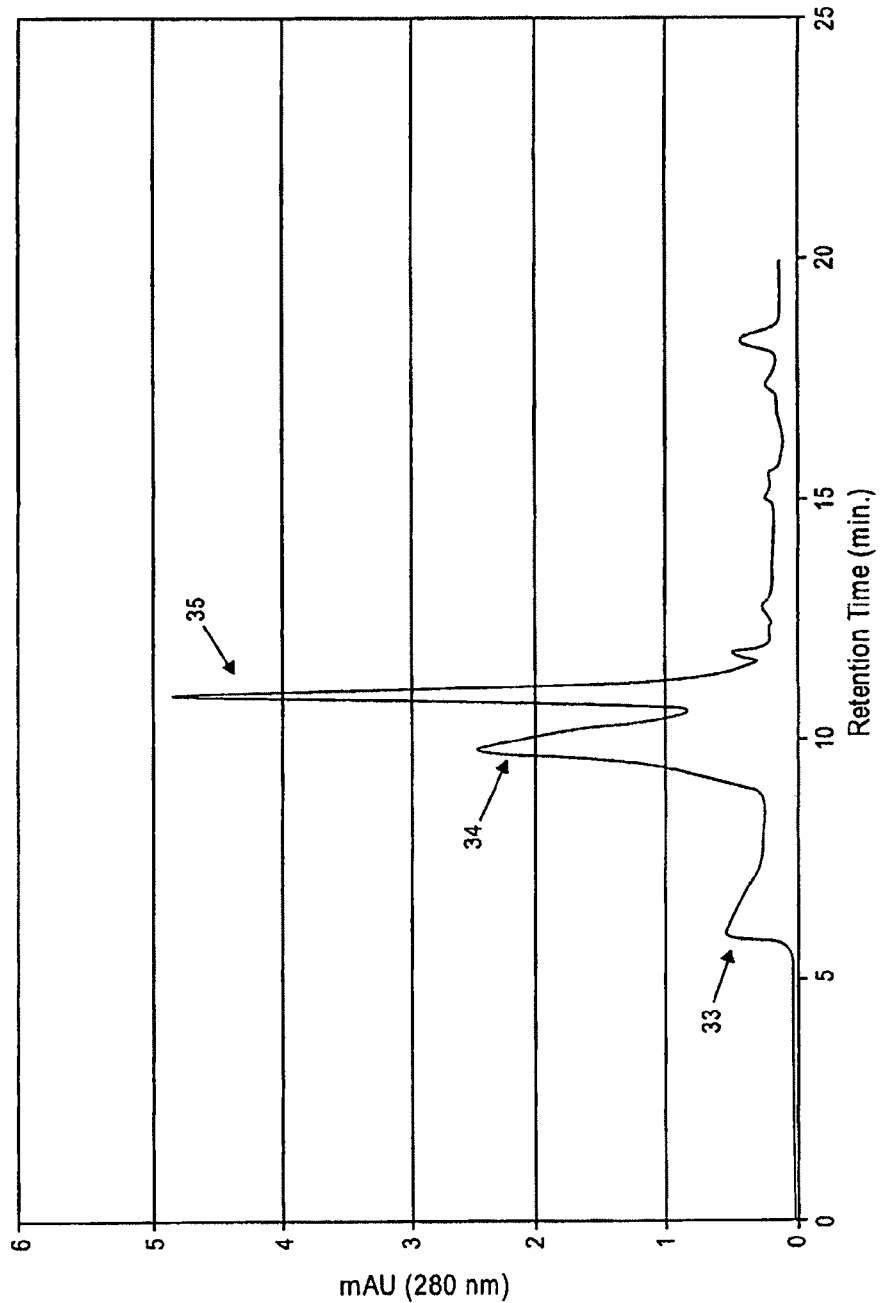
FIG. 14 shows an HPLC chromatogram illustrating the conjugation of an aldehyde functionalized branched polymer of the invention to EPO.

The aldehyde functionalized polymer from Example 8 (2.5 mg) was dissolved in 80 mM sodium cyanoborohydride (1 mL) prepared in 100 mM sodium acetate buffer at pH 4.6. Erythropoietin (EPO, 0.2 mL, FIG. 1) obtained from a transgenic chicken (for example, as disclosed in U.S. Pat. No. 6,730,822) in 100 mM sodium phosphate buffer (pH 6.98) at a concentration of 0.44 mg/mL was added to 0.3 mL of the polymer and shaken at room temperature for 72 hours. The resulting reaction mixture was analyzed on a Shodex KW-803 size exclusion column using a Beckman Coulter System Gold or Agilent 1100 series HPLC system at 280 nm with a flow rate of 1 mL/min. (FIG. 14 (33: conjugate; 34: EPO; 35: buffer)).

Example 21

Preparation of Linear Conjugates of Poly-HEMA-PC Via ATRP Employing 3-Bromopropionic Acid as an Initiator a. Polymerization Reaction Controlled polymerization of 2-methacryloyloxyethyl-2'-(trimethylammonium)ethyl phosphate in water may be accomplished employing 3-bromopropionic acid (or a salt thereof, e.g., a sodium salt) as an atom transfer radical polymerization (ATRP) initiator. The initiator 3-bromopropionic acid (153 mg, 1 mmol,) is dissolved in sufficient distilled, deionized water (about 15 to about 50 ml) in a sealed reaction flask equipped with a stirring apparatus. After purging the flask with nitrogen, Cu(I)Br catalyst (1.4 mg, 1.0 mmol) and bipyridine (bpy) ligand (320 mg, 2.0 mmol.) are added and the solution is stirred under a nitrogen atmosphere. Monomer, 2-methacryloyloxyethyl-2'-(trimethylammonium)ethyl phosphate, is then added as a solid to the reaction mixture under nitrogen. The molecular weight of the desired product determines the quantity of monomer employed as indicated in the table below.

| Average Molecular Weight (Daltons) | Quantity of 2-methacryloyloxyethyl-2'-(trimethylammonium)ethyl phosphate (calculated for inner salt) |
|---|---|
| 1,000 | 0.852 g, 2.9 mmol |
| 2,000 | 1.848 g, 6.3 mmol |
| 5,000 | 4.84 g, 16.5 mmol |
| 10,000 | 9.8 g, 33 mmol |
| 20,000 | 19.8 g, 67.5 mmol |
| 40,000 | 39.7 g, 135 mmol |

The reaction mixture immediately becomes dark green and progressively more viscous. A temperature rise of about 2-4° C. typically indicates that polymerization is occurring. After the reaction is complete the resulting homopolymer bearing a free reactive carboxyl group may be precipitated by addition of THF, redissolved in water, and chromatographed on a silica gel column to remove residual ATRP catalyst. Alternatively, where it is desirable to couple the homopolymer product, the conjugation of the homopolymeric product may be conducted without THF precipitation and chromatography as described below.

b. Conjugation Reactions

Conjugation of the homopolymeric product prepared as above in part 2a to a biologically active agent through the carboxylic acid of the propionic acid group derived from the 3-bromopropionic acid initiator may conducted by the use of a suitable dehydrating agent, including but not limited to 1-ethyl-3-(3-dimethyllaminopropyl)carbodiimide hydrochloride (EDC), with or without the formation of an intermediate N-hydroxysuccinimide ester (NHS).

EDC activated carboxyl-containing homopolymeric products or NHS ester-containing homopolymeric products may be prepared by addition of a buffering agent (e.g. HEPES) to adjust the pH of an aqueous solution of the carboxyl-containing homopolymer polymer product described in 2a to about pH 7.2. EDC is introduced (about 0.95 to about 0.98 mmol for each 1 mmol of carboxyl containing polymer) to form an EDC activated carboxylic acid. Where it is deemed desirable to form an NHS ester, 1.1 mmoles of N-hydroxysuccinimide is added per mmol of the carboxyl containing polymer following the addition of the EDC. After formation, NHS esters may be isolated for later use either by lyophilization of the precipitation with a suitable solvent (e.g., THF) followed by lyophilization of the precipitate. As NHS esters are generally more stable to hydrolysis at pH 5-6, where the NHS ester is to be isolated it is typically desirable to reduce the pH prior to precipitation and/or lyophilization of the NHS-ester, which is done on a desalting column equilibrated in a pH 4-pH 5 buffer.

Conjugates of biologically active agents bearing a primary amine (including but not limited to erythropoietin, granulocyte-colony stimulating factor, interferon alpha, interferon beta, human growth hormone, and imiglucerase) with polymeric product bearing an EDC activated carboxylic acid or an NHS ester may be conducted in a suitable buffer such as HEPES at pH 5-8 preferably at about pH7.0. For the reaction, a small excess of the biologically active agent (e.g. 1.1 mmol of the agent per mmol of the polymeric material) is introduced. The reaction may be conducted at room temperature, however, reaction overnight (12 hours) on ice is typically preferred. Where the biologically active agent has more than one reactive amine it may be preferable to introduce the activated carboxylic acid bearing polymer into an excess of the biologically active agent to limit the formation of molecules having more than one polymer group associated with a single biologically active agent.

Preparation of Protein/Polypeptide Poly-HEMA-PC Conjugates Employing 3-Bromopropionic Acid as an Initiator

| Average Molecular Weight of polymer portion of the conjugate (Daltons) | Conjugated Biologically Active Agent |
|---|---|
| 1,000 | erythropoietin |
| 2,000 | erythropoietin |
| 5,000 | erythropoietin |
| 10,000 | erythropoietin |
| 20,000 | erythropoietin |
| 40,000 | erythropoietin |
| 1,000 | granulocyte-colony stimulating factor |
| 2,000 | granulocyte-colony stimulating factor |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 1,000 | interferon alpha |
| 2,000 | interferon alpha |
| 5,000 | interferon alpha |
| 10,000 | interferon alpha |
| 20,000 | interferon alpha |
| 40,000 | interferon alpha |
| 1,000 | interferon beta interferon beta |
| 2,000 | interferon beta |
| 5,000 | interferon beta |
| 10,000 | interferon beta |
| 20,000 | interferon beta |
| 40,000 | interferon beta |
| 1,000 | human growth hormone |
| 2,000 | human growth hormone |
| 5,000 | human growth hormone |
| 10,000 | human growth hormone |
| 20,000 | human growth hormone |
| 40,000 | human growth hormone |
| 1,000 | imiglucerase |
| 2,000 | imiglucerase |
| 5,000 | imiglucerase |
| 10,000 | imiglucerase |
| 20,000 | imiglucerase |
| 40,000 | imiglucerase |

Conjugates of biologically active agents bearing a hydroxyl group or sulfhydryl groups may also be prepared. The reaction of a biologically active agent bearing a hydroxyl group or a sulfhydryl group with a polymeric product bearing an EDC activated carboxylic acid will form a covalent conjugate having the biologically active agent attached to the polymeric group by an ester linkage or thioester linkage, respectively.

The preparation of conjugates of poly-HEMA-PC and biologically active agents in some cases may be conducted in "single pot reactions." In this example, the ATRP reaction may be conducted in aqueous solution followed by addition of a suitable buffer (e.g., HEPES) and a water soluble dehydrating agent (EDC) to form a poly-HEMA-PC polymer bearing an activated carboxylic acid. Subsequent addition of a biologically active agent bearing a primary amine to the activated polymer forms a conjugate with the polymer via an amide linkage.

c. Purification and Molecular Weight Determination

Conjugates prepared as in section 2b are chromatographed on Superdex 75 in normal saline (0.9 g NaCl per 100 ml) or in phosphate buffered saline (PBS) either of which are pharmaceutically acceptable excipients. Molecular weight is determined by elution volume against calibration standards available from commercial suppliers including. In place of chromatography, dialysis may be employed to remove unwanted low molecular weight contaminants.

Example 22

Preparation of Conjugates of Poly-HEMA-PC Via ATRP Employing an N-Hydroxysuccinimide Ester as an Initiator a. Preparation of N-Hydroxysuccinimide Ester Initiators N-hydroxysuccinimide esters (NHS esters) may be purchased or prepared from the corresponding halogenated carboxylic acids by reacting an aqueous solution of the carboxylic acid with a dehydrating agent such as EDC followed by addition of N-hydroxysuccinimide. The initiator bromoacetic acid N-hydroxysuccinimide ester, which is commercially available from Sigma-Aldrich, may also be prepared by reaction of an aqueous solution of bromoacetic acid with EDC followed by addition of N-hydroxysuccinimide.

b. ATRP Reactions Employing NHS Esters

NHS esters of carboxylic acids, for example alkyl carboxylic acids, bearing one or more bromine, chlorine or iodine atoms may be employed as initiators in ATRP reactions provided they do not contain chemical groups that will interfere with the polymerization reaction. For the reaction. Polymerization of 2-methacryloyloxyethyl-2'-(trimethylammonium) ethyl phosphate may be accomplished employing bromoacetic acid N-hydroxysuccinimide ester as an atom transfer radical polymerization (ATRP) initiator. The initiator (1 mmol,) is dissolved in sufficient distilled, deionized water that has been cooled on ice (about 15 ml) in a sealed reaction flask equipped with a stirring apparatus. After purging the flask with nitrogen, Cu(I)Br catalyst (1.4 mg, 1.0 mmol) and bipyridine (bpy) ligand (320 mg, 2.0 mmol.) are added and the solution is stirred under a nitrogen atmosphere. Immediately prior to use, monomer, 2-methacryloyloxyethyl-2'-trimethylammoniumethyl phosphate is diluted in sufficient water and the pH adjusted to approximately pH 4.5 with HCl or NaOH as necessary. Monomer solution is cooled on ice and is added to the reaction mixture, which is stirred under nitrogen. The molecular weight of the desired product determines the quantity of monomer employed as indicated in the preceding example.

Following addition of the monomer, the reaction mixture becomes dark green and progressively more viscous. A temperature rise of about 2-4° C. indicates that polymerization is occurring. While reactions are typically carried out on ice, for some monomer and initiator combinations it may be necessary to raise the temperature slightly or even to warm the mixture to room temperature for up to 10 minutes. After the reaction is complete the reaction mixture is cooled on ice.

c. Conjugation Reactions

Following the polymerization reaction in part b, the product may be reacted with an amine containing biologically active agent to form a conjugate having the polymeric portion of the conjugate linked to the biologically active agent by an amide linkage. Where the biologically active agent is stable at pH 4 to pH 5 it may be added to the reaction mixture prior to adjusting the pH into the range of about pH 7.0 to about pH 7.5 by addition of dilute base (e.g., NaOH solution) or a suitable buffer, thereby maintaining the NHS ester in the range of maximum stability until active agent is present for conjugation. Alternatively, the reaction mixture from 3b may be adjusted into the range of about pH 7.0 to about pH 7.5 and then the biologically active agent is immediately added to the reaction mixture. Following incubation sufficient for the biologically active agent to couple to the polymeric agent the reaction mixture is chromatographed on Superdex to separate the desired product from small molecule contaminants (e.g., unpolymerized monomers, catalyst, and bipyridine) and unreacted biologically active agent. Where the biologically active agent is of sufficient mass, polymer compounds that are not coupled to the biologically active agent may also be separated from the conjugated biologically active agent. In addition, ion exchange chromatography may be used to separate conjugated biologically active agents, such as polymer conjugates of proteins and polypeptides, from unconjugated biologically active agents and polymer compounds that are not coupled to a biologically active agent.

Preparation of Protein/Polypeptide Poly-HEMA-PC Conjugates Employing 3-Bromoacetic Acid NHS Esters as an Initiator

| Average Molecular Weight of polymer portion of the conjugate (Daltons) | Conjugated Biologically Active Agent |
|---|---|
| 1,000 | erythropoietin |
| 2,000 | erythropoietin |
| 5,000 | erythropoietin |
| 10,000 | erythropoietin |
| 20,000 | erythropoietin |
| 40,000 | erythropoietin |
| 1,000 | granulocyte-colony stimulating factor |
| 2,000 | granulocyte-colony stimulating factor |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 1,000 | interferon alpha |
| 2,000 | interferon alpha |
| 5,000 | interferon alpha |
| 10,000 | interferon alpha |
| 20,000 | interferon alpha |
| 40,000 | interferon alpha |
| 1,000 | interferon beta interferon beta |
| 2,000 | interferon beta |
| 5,000 | interferon beta |
| 10,000 | interferon beta |
| 20,000 | interferon beta |
| 40,000 | interferon beta |
| 1,000 | human growth hormone |
| 2,000 | human growth hormone |
| 5,000 | human growth hormone |
| 10,000 | human growth hormone |
| 20,000 | human growth hormone |
| 40,000 | human growth hormone |
| 1,000 | imiglucerase |
| 2,000 | imiglucerase |
| 5,000 | imiglucerase |
| 10,000 | imiglucerase |
| 20,000 | imiglucerase |
| 40,000 | imiglucerase |

Example 23

Preparation of Linear Conjugates of Poly-HEMA-PC Via ATRP Employing 3-Bromopropionaldehyde Dimethylacetal as an Initiator a. Polymerization Reaction and Deprotection of the Aldehyde The polymerization of 2-methacryloyloxyethyl-2'-(trimethylammonium)ethyl phosphate in water is conducted employing an ATRP reaction as set forth in Example 21, part 2a substituting 3-bromopropionaldehyde dimethylacetal as an initiator in place of 3-bromopropionic acid. As with the products in example 2, the ratio of monomer to initiator employed will determine the molecular weight of the product, and products with molecular weights of 1,000, 2,000, 5,000, 10,000, 20,000, and 40,000, are prepared employing suitable initiator monomer ratios. Upon completion of the polymerization reaction the dimethylacetyl may be converted to an aldehyde by exposure to aqueous acid (e.g., aqueous HCl or acetic acid). Where necessary, unused monomers and other polymerization reaction reagents may be removed from the aldehyde bearing polymer products on a desalting gel column or by chromatography for example on Superdex. Where the aldehyde is to be coupled to an amine the chromatographic media may be equilibrated with a suitable buffer such as pH 9.5 borate buffer.

b. Conjugation Reactions

Aldehyde bearing products from 4a may be reacted with a primary amine containing biologically active agents to form an imine bond. Primary amine containing biologically active agents, include polypeptides and proteins that contain an accessible amino group on a naturally occurring amino acid, or those into which a primary amine as been introduced for the purpose of coupling them to the polymeric agent. Imine bond formation is conducted in borate buffer pH 9.5 or under other suitable imine bond forming conditions. Proteins or polypeptides, including but not limited to erythropoietin, granulocyte-colony stimulating factor, interferon alpha, interferon beta, human growth hormone, and imiglucerase, may be reacted with aldehyde containing polymers of any molecular weight set forth in 4a to form conjugates having hydrolytically susceptible linkages. Where it is desirable the imine may be reduced to an amine to prevent hydrolysis of that conjugate linkage.

Example 24

Preparation of Linear Conjugates of Poly-HEMA-PC Employing Maleimide Conjugation of Ssulfhydryl Containing Biologically Active Agents a. Polymerization Reactions The polymerization of 2-methacryloyloxyethyl-2'-(trimethylammonium)ethyl phosphate in water is conducted employing an ATRP reaction as set forth in Example 21, part 2a, substituting 3-bromopropanamine as an initiator in place of 3-bromopropionic acid. As with the products in example 21, the ratio of monomer to initiator employed will determine the molecular weight of the product, and products with molecular weights of 1,000, 2,000, 5,000, 10,000, 20,000, or 40,000, are prepared employing suitable initiator monomer ratios. Upon completion of the polymerization reaction, polymerization reaction reagents (e.g., catalyst, ligand, unpolymerized monomers) may be removed from the aldehyde bearing polymer products on a desalting gel column or by chromatography for example on Superdex. Where the amine bearing polymer product is to be coupled to a maleimidyl functionality through the use of a bifunctional agent containing an NHS ester, the chromatographic media may be equilibrated with a suitable buffer such as phosphate, bicarbonate/carbonate HEPES or borate buffers having a pH of about pH 7 to about pH 9.

b. Introduction of a Maleimide Functionality Through the Use of a Bifunctional Agent The amine bearing polymer products of any molecular weight prepared in 5a are suspended in 50 mM pH 7.5 phosphate buffer and cooled to 4° C. A 1.2 molar excess of sulfo-succinimidyl 4-(N-maleimidomethyl)cyclohexane-1-carboxylate (Sulfo-SMCC, available from Pierce) is introduced and the reaction is allow to proceed for 8 hours at 4° C. Alternatively, the reaction may be initiated at 4° C. and stirred for 1-2 hours at that temperature and then gradually warmed to room temperature. The reaction may be followed by the release of N-hydroxysuccinimide at 260 nm.

Once prepared, the maleimide bearing polymers may be reacted immediately with sulfhydryl containing biologically active gents. Optionally, the products may be prepared for later use by precipitation with an organic solvent such as tetrahydrofuran (THF) and lyophilization or subjected to purification by dialysis or chromatography on a desalting gel (e.g., Biogel P6DG) and lyophilization.

c. Conjugation with Sulfhydryl Bearing Biologically Active Agents

Maleimide bearing products of any molecular weight from 5b may be reacted with sulfhydryl containing biologically active agents to form an imine bond. Sulfhydryl containing biologically active agents including polypeptides and proteins that contain cysteine residues, and those into which cysteines have been introduced for the purpose of forming conjugates, including but not limited to erythropoietin, granulocyte-colony stimulating factor, interferon alpha, interferon beta, human growth hormone, and imiglucerase. When necessary or desirable, sulfhydryl groups may be introduced during protein or polypeptide preparation by chemical or biochemical means that can introduce either cysteine or other sulfhydryl containing amino acids, or alternatively, by subsequent chemical modification with agents that introduce sulfhydryl groups (e.g., 2-iminothiolane).

Biologically active agents bearing a sulfhydryl group may be introduced into the reaction mixture prepared in 5b subsequent to the reaction of the bifunctional agent Sulfo-SMCC with the amine bearing polymer prepared in 5a. In the alternative, where a sulfhydryl bearing biologically active agent does not contain any interfering primary amines or other groups that can react with the NHS ester of Sulfo-SMCC, the biologically active agent may introduced into the reaction mixture either before, or simultaneously with, the Sulfo-SMCC as selective coupling to both the NHS ester to an amine and maleimide to a sulfhydryl will occur under similar conditions (e.g., a pH of about 7.0 to about 7.5).

d. Purification and Molecular Weight Determination

As described in Example 21, part 2c, conjugates may be purified and their molecular weight determined by chromatographic means. Chromatography of the conjugates prepared in 5b is conducted on Superdex 75 or Superdex Peptide in normal saline or phosphate buffered saline (PBS), and molecular weight is determined against chromatography calibration standards.

Example 25

Preparation of Branched Conjugates of Poly-HEMA-PC Via ATRP Employing 2,3-Dibromopropionic Acid as an Initiator a. Polymerization Reactions

The polymerization of 2-methacryloyloxyethyl-2'-(trimethylammonium)ethyl phosphate in water is conducted employing an ATRP reaction as set forth in Example 21, part 2a substituting 2,3-dibromopropionaldehyde dimethylacetal (1 mmol, 271 mg) as an initiator in place of 3-bromopropionic acid to form a 2 armed branched polymeric compound. As discussed in Example 21, the molecular weight of the desired product determines the quantity of monomer employed as indicated in the table below.

| Average Molecular Weight (Daltons) | Quantity of 2-methacryloyloxyethyl-2'-(trimethylammonium)ethyl phosphate (calculated for inner salt) |
|---|---|
| 5,000 | 4.7 g, 16.1 mmol |
| 10,000 | 9.7 g, 33.1 mmol |
| 20,000 | 19.7 g, 67.1 mmol |
| 40,000 | 39.7 g, 135 mmol | b. Conjugation Reactions

Conjugation of the branched homopolymeric product prepared as in part a to a biologically active agent through the carboxylic acid of the propionic acid group derived from the 2,3-dibromopropionic acid initiator may be conducted by the use of a suitable dehydrating/carboxylic acid activating agent (e.g. EDC) or through the formation of an intermediate N-hydroxysuccinimide ester (NHS) as described in Example 21 part b. After formation the NHS esters may be reacted immediately with a biologically active agent bearing a primary amine or isolated for later use either by lyophilization or by precipitation with a suitable solvent (e.g., THF) followed by lyophilization of the precipitate as discussed in Example 21, part b.

Conjugates of biologically active agents bearing a primary amine (including but not limited to erythropoietin, granulocyte-colony stimulating factor, interferon alpha, interferon beta, human growth hormone, and imiglucerase) with the branched polymeric products bearing an EDC activated carboxylic acid or an NHS ester are prepared in a suitable buffer such as HEPES at pH 5-8 preferably at about pH 7.0 as described in Example 21, part b.

Preparation of Protein/Polypeptide Poly-HEMA-PC Conjugates Employing 2,3-Dibromopropionaldehyde Dimethylacetal as an Initiator

| Average Molecular Weight of polymer portion of the conjugate (Daltons) | Conjugated Biologically Active Agent |
|---|---|
| 5,000 | erythropoietin |
| 10,000 | erythropoietin |
| 20,000 | erythropoietin |
| 40,000 | erythropoietin |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 5,000 | interferon alpha |
| 10,000 | interferon alpha |
| 20,000 | interferon alpha |
| 40,000 | interferon alpha |
| 5,000 | interferon beta |
| 10,000 | interferon beta |
| 20,000 | interferon beta |
| 40,000 | interferon beta |
| 5,000 | human growth hormone |
| 10,000 | human growth hormone |
| 20,000 | human growth hormone |
| 40,000 | human growth hormone |
| 5,000 | imiglucerase |
| 10,000 | imiglucerase |
| 20,000 | imiglucerase |
| 40,000 | imiglucerase |

As described in part Example 21, part b, conjugates of biologically active agents bearing a hydroxyl group or a sulfhydryl group may also be prepared. The reaction of a biologically active agent bearing a hydroxyl group or a sulfhydryl group with a branched polymeric product bearing an activated carboxylic acid (e.g. an EDC activated carboxyl) will form a covalent conjugate having the biologically active agent attached to the polymeric group by an ester linkage or thioester linkage, respectively.

The preparation of branched conjugates of poly-HEMA-PC and biologically active by "single pot reactions" is also possible with branched chain polymers.

c. Purification and Molecular Weight Determination

Purification and molecular weight determination are conducted as described in Example 21, part c.

Example 26

Preparation of Branched Conjugates of Poly-HEMA-PC Via ATRP Employing 3-Bromopropionaldehyde Dimethylacetal as an Initiator a. Polymerization Reaction and Deprotection of the Aldehyde The polymerization of 2-methacryloyloxyethyl-2'-(trimethylammonium)ethyl phosphate in water is conducted employing an ATRP reaction as set forth in Example 21, part a substituting 2,3-dichloropropionaldehyde or its dimethylacetal (1 mmol) as an initiator in place of 3-bromopropionic acid to form a 2 armed branched polymeric compound. As with the branched polymeric products in example 25, the ratio of monomer to initiator employed will determine the molecular weight of the product, and products with molecular weights of 5,000, 10,000, 20,000, and 40,000, are prepared employing suitable initiator monomer ratios. Upon completion of the polymerization reaction, if the dimethyl acetal has been employed, the dimethylacetyl group is converted to an aldehyde by exposure to aqueous acid (e.g., aqueous HCl or acetic acid). Unused monomers and other polymerization reaction reagents including catalyst may be removed from the aldehyde bearing polymer products by dialysis, or by chromatography desalting gel column or Superdex. Where the aldehyde is to be coupled to an amine the chromatographic media may be equilibrated with a suitable buffer such as pH 9.5 borate buffer.

b. Conjugation Reactions

Conjugates of biologically active agents bearing a primary amine (including but not limited to erythropoietin, granulocyte-colony stimulating factor, interferon alpha, interferon beta, human growth hormone, and imiglucerase) are formed with the branched polymeric products of any molecular weight prepared in part a. The aldehyde bearing branched polymeric products from part a are reacted with the primary amine containing biologically active agents to form an imine bond as described in Example 23, part a. Where it is desirable the imine may be reduced to an amine to prevent hydrolysis of that conjugate linkage as described in Example 23, part b.

c. Purification and Molecular Weight Determination

Molecular weight determinations and purification, particularly where the imine linkage has been reduced to an amine with a borohydride reagent, are conducted as described in Example 21, part c.

Example 27

Preparation of Branched Conjugates of Poly-HEMA-PC Employing Maleimide Conjugation of Sulfhydryl Containing Biologically Active Agents The polymerization of 2-methacryloyloxyethyl-2'-(trimethylammonium)ethyl phosphate in water is conducted employing an ATRP reaction as set forth in Example 24, part a, substituting 1,3-dibromo-2-propanamine as an initiator in place of 3-bromopropionic acid to prepare a two armed branched polymer. As with the products in examples 21 and 24, the ratio of monomer to initiator employed will determine the molecular weight of the product, and products with molecular weights of 5,000, 10,000, 20,000, or 40,000, are prepared employing suitable initiator monomer ratios. Maleimide functionalities may be introduced into the branched chain polymer compound to form branched chain maleimide containing polymeric compounds through the use of bifunctional agents (e.g., Sulfo-SMCC) as described in Example 24 part b. The branched chain maleimide containing polymeric compounds may be prepared for later as described in part 5b. Alternatively, once prepared the branched chain maleimide containing polymeric compounds may be reacted with sulfhydryl containing biologically active agents to form conjugates. Conjugates of biologically active agents bearing a sulfhydryl (including but not limited to erythropoietin, granulocyte-colony stimulating factor, interferon alpha, interferon beta, human growth hormone, and imiglucerase) with branched chain maleimide containing polymeric compounds of 5,000, 10,000, 20,000, or 40,000 Daltons are prepared as described in Example 24, parts c and d.

Example 28

Preparation of Forked Conjugates of Poly-HEMA-PC Via ATRP Employing DL-Bromosuccinic Acid as an Initiator a. Polymerization Reactions The polymerization of 2-methacryloyloxyethyl-2'-(trimethylammonium)ethyl phosphate in water is conducted employing an ATRP reaction as set forth in Example 21, part a substituting DL-bromosuccinic acid (bromobutanedioic acid, Acros Organics) as an initiator in place of 3-bromopropionic acid. The reaction forms a dicarboxylic polymeric product bearing the carboxyl groups on the succinic acid group derived from the initiator. The molecular weight of the desired product determines the quantity of monomer employed, and polymeric molecules having an average molecular weight of 1,000, 2,000, 5,000, 10,000, 20,000, and 40,000 Daltons are prepared using suitable monomer initiator ratios.

b. Conjugation Reactions

Conjugation of the dicarboxylic polymeric product prepared as in part a to a biologically active agent through the carboxylic acid groups is conducted by the use of a suitable dehydrating/carboxylic acid activating agent (e.g. EDC) or through the formation of an intermediate N-hydroxysuccinimide ester (NHS) as described in Example 21 part b adjusting the amount of reagents to account for the 2 moles of carboxyl functionalities present per mole of dicarboxylic polymeric product. Where NHS esters are prepared, they may be reacted immediately with a biologically active agent bearing a primary amine or isolated for later use either by lyophilization or by precipitation with a suitable solvent (e.g., THF) followed by lyophilization of the precipitate as discussed in Example 21, part b.

Conjugates of biologically active agents bearing a primary amine (including but not limited to erythropoietin, granulocyte-colony stimulating factor, interferon alpha, interferon beta, human growth hormone, and imiglucerase) with the dicarboxylic polymeric product bearing an EDC activated carboxylic acid groups or NHS ester groups are prepared in a suitable buffer such as HEPES at pH 5-8 preferably at about pH 7.0 as described in Example 21, part b.

Preparation of Forked Protein/Polypeptide Poly-HEMA-PC Conjugates Employing DL-Bromosuccinic Acid as an Initiator

| Average Molecular Weight of polymer portion of the conjugate (Daltons) | Conjugated Biologically Active Agent |
|---|---|
| 5,000 | erythropoietin |
| 10,000 | erythropoietin |
| 20,000 | erythropoietin |
| 40,000 | erythropoietin |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 5,000 | interferon alpha |
| 10,000 | interferon alpha |
| 20,000 | interferon alpha |
| 40,000 | interferon alpha |
| 5,000 | interferon beta |
| 10,000 | interferon beta |
| 20,000 | interferon beta |
| 40,000 | interferon beta |
| 5,000 | human growth hormone |
| 10,000 | human growth hormone |
| 20,000 | human growth hormone |
| 40,000 | human growth hormone |
| 5,000 | imiglucerase |
| 10,000 | imiglucerase |
| 20,000 | imiglucerase |
| 40,000 | imiglucerase |

As described in part 2b, conjugates of biologically active agents bearing a hydroxyl group or a sulfhydryl group may also be prepared. The reaction of a biologically active agent bearing a hydroxyl group or a sulfhydryl group with a branched polymeric product bearing an activated carboxylic acid groups (e.g. EDC activated carboxyls) will form forked covalent conjugates having the biologically active agents attached to the polymeric group by ester linkages or thioester linkages, respectively.

The preparation of forked conjugates of poly-HEMA-PC and biologically active agents by "single pot reactions" is also possible with the dicarboxylic polymeric products prepared as in part a.

c. Purification and Molecular Weight Determination

Purification and molecular weight determination are conducted as described in Example 21, part c.

Example 29

Preparation of Branched Conjugates of Poly-HEMA-PC Via ATRP Employing 2-Chloroglutaraldehyde as an Initiator a. Polymerization Reaction and Deprotection of the Aldehyde The polymerization of 2-methacryloyloxyethyl-2'-(trimethylammonium)ethyl phosphate in water is conducted employing an ATRP reaction as set forth in Example 21, part 2a substituting 2-chloroglutaraldehyde (see U.S. Pat. No. 6,703,528, the disclosure of which is incorporated in its entirety herein by reference) or its dimethylacetal as an initiator in place of 3-bromopropionic acid. As with the polymeric products in example 21, the ratio of monomer to initiator employed will determine the molecular weight of the dialdehyde bearing polymeric product. Dialdehyde polymeric products with molecular weights of 1,000, 2,000, 5,000, 10,000, 20,000, and 40,000 are prepared employing suitable initiator monomer ratios. Upon completion of the polymerization reaction, if the dimethyl acetal has been employed, the dimethylacetyl group is converted to an aldehyde by exposure to aqueous acid (e.g., aqueous HCl or acetic acid). Unused monomers and other polymerization reaction reagents including catalyst may be removed from the dialdehyde polymeric product by dialysis, or by chromatography desalting gel column or Superdex. Where a dialdehyde polymeric product is to be coupled to an amine the chromatographic media may be equilibrated with a suitable buffer such as pH 9.5 borate buffer.

b. Conjugation Reactions

Conjugates of biologically active agents bearing a primary amine (including but not limited to erythropoietin, granulocyte-colony stimulating factor, interferon alpha, interferon beta, human growth hormone, and imiglucerase) are formed with the dialdehyde polymeric products of any molecular weight prepared in part a. The dialdehyde polymeric products from part a are reacted with the primary amine containing biologically active agents to form imine bonds as described in Example 23, part a adjusting for the two moles of aldehyde per mole of dialdehyde polymeric product. Where it is desirable the imine bonds may be reduced to an amine to prevent hydrolysis of that conjugate linkage as described in Example 23, part b.

c. Purification and Molecular Weight Determination

Molecular weight determinations and purification, particularly where the imine linkage has been reduced to amines with a borohydride reagent, are conducted as described in Example 21, part c.

Example 30

Preparation of Forked Conjugates of Poly-HEMA-PC Employing Maleimide Conjugation of Sulfhydryl Containing Biologically Active Agents The polymerization of 2-methacryloyloxyethyl-2'-(trimethylammonium)ethyl phosphate in water is conducted employing an ATRP reaction as set forth in Example 21, part a, substituting 1,3-diamino-2-bromopropane as an initiator in place of 3-bromopropionic acid to prepare a forked compound. As with the products in examples 21 and 24, the ratio of monomer to initiator employed will determine the molecular weight of the product, and products with molecular weights of 5,000, 10,000, 20,000, or 40,000, are prepared employing suitable initiator monomer ratios. Maleimide functionalities may be introduced on to the amine groups through the use of a bifunctional agent (e.g., Sulfo-SMCC) as described in Example 24 part b. The forked polymeric compounds having two reactive maleimide groups may be prepared for later as described in Example 24, part b. Alternatively, once prepared the maleimide containing polymeric compounds may be reacted with sulfhydryl containing biologically active agents to form conjugates. Conjugates of biologically active agents bearing a sulfhydryl (including but not limited to erythropoietin, granulocyte-colony stimulating factor, interferon alpha, interferon beta, human growth hormone, and imiglucerase) with branched chain maleimide containing polymeric compounds of 5,000, 10,000, 20,000, or 40,000 Daltons are prepared as described in part 5c and 5d. Conjugates of FAb$_2$ antibody fragments, which can be reduced with mercaptoethanol or DTT (dithiothreitol) to yield a single sulfhydryl group at the end of each of the resulting FAb fragments, are prepared in the same manner. The forked conjugates of FAb fragments are particularly useful as "pseudo-antibody constructs."

Example 31

Preparation of Branched and Forked Conjugates of Poly-HEMA-PC Via ATRP Employing 2,3-Bibromosuccinic Acid as an Initiator a. Polymerization Reactions The polymerization of 2-methacryloyloxyethyl-2'-(trimethylammonium)ethyl phosphate in water is conducted employing an ATRP reaction as set forth in Example 21, part 2a substituting 2,3-dibromosuccinic acid as an initiator in place of 3-bromopropionic acid. The reaction forms a dicarboxylic acid product having two polymer arms that bears the carboxyl groups on the succinic acid group derived from the initiator. The molecular weight of the desired product determines the quantity of monomer employed, and polymeric molecules having an average molecular weight of 5,000, 10,000, 20,000, and 40,000 Daltons are prepared using suitable monomer initiator ratios.

b. Conjugation Reactions

Conjugation of the dicarboxylic acid products having two polymer arms prepared as in part 12a to a biologically active agent through the carboxylic acid groups is conducted by the use of a suitable dehydrating/carboxylic acid activating agent (e.g. EDC) or through the formation of an intermediate N-hydroxysuccinimide ester (NHS) as described in Example 21 part 2b adjusting the amount of reagents to account for the 2 moles of carboxyl functionalities present per mole of dicarboxylic polymeric product. Where NHS esters are prepared, they may be reacted immediately with a biologically active agent bearing a primary amine or isolated for later use either by lyophilization or by precipitation with a suitable solvent (e.g., THF) followed by lyophilization of the precipitate as discussed in part 2b.

Conjugates of biologically active agents bearing a primary amine (including but not limited to erythropoietin, granulocyte-colony stimulating factor, interferon alpha, interferon beta, human growth hormone, and imiglucerase) with the dicarboxylic acid product having two polymer arms bearing an EDC activated carboxylic acid groups or NHS ester groups are prepared in a suitable buffer such as HEPES at pH 5-8 preferably at about pH 7.0 as described in Example 21, part b.

Preparation of Branched and Forked Protein/Polypeptide Poly-HEMA-PC Conjugates Employing 2,3-Dibromosuccinic Acid as an Initiator

| Average Molecular Weight of polymer portion of the conjugate (Daltons) | Conjugated Biologically Active Agent |
| --- | --- |
| 5,000 | erythropoietin |
| 10,000 | erythropoietin |
| 20,000 | erythropoietin |
| 40,000 | erythropoietin |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 5,000 | interferon alpha |
| 10,000 | interferon alpha |
| 20,000 | interferon alpha |
| 40,000 | interferon alpha |
| 5,000 | interferon beta |

| Average Molecular Weight of polymer portion of the conjugate (Daltons) | Conjugated Biologically Active Agent |
|---|---|
| 10,000 | interferon beta |
| 20,000 | interferon beta |
| 40,000 | interferon beta |
| 5,000 | human growth hormone |
| 10,000 | human growth hormone |
| 20,000 | human growth hormone |
| 40,000 | human growth hormone |
| 5,000 | imiglucerase |
| 10,000 | imiglucerase |
| 20,000 | imiglucerase |
| 40,000 | imiglucerase |

As described in part 2b, conjugates of biologically active agents bearing a hydroxyl group or a sulfhydryl group may also be prepared. The reaction of a biologically active agent bearing a hydroxyl group or a sulfhydryl group with a dicarboxylic acid product having two polymer arms bearing an activated carboxylic acid groups (e.g. EDC activated carboxyls) will form branched and forked covalent conjugates having the biologically active agents attached to the two armed polymeric group by ester linkages or thioester linkages, respectively.

The preparation of branched and forked conjugates of poly-HEMA-PC and biologically active agents by "single pot reactions" is also possible with the dicarboxylic acid product having two polymer arms prepared as in part a.

c. Purification and Molecular Weight Determination

Purification and molecular weight determination are conducted as described in Example 21, part c.

Example 32

Preparation of Branched and Forked Conjugates of Poly-HEMA-PC Via a TRP Employing 3,3-Dichloroglutaric Acid as an Initiator Branched and forked polymeric conjugates of poly-HEMA-PC via ATRP may be prepared as in example 31 employing 3,3-dichloroglutaric acid as an initiator in place of dibromosuccinic acid. Conjugates of biologically active agents bearing a primary amine (including but not limited to erythropoietin, granulocyte-colony stimulating factor, interferon alpha, interferon beta, human growth hormone, and imiglucerase) with the dicarboxylic acid product having two polymer arms of any molecular weight described in Example 31 may be formed.

Preparation of Branched and Forked Protein/Polypeptide Poly-HEMA-PC Conjugates Employing 3,3-Dichloroglutaric Acid as an Initiator

| Average Molecular Weight of polymer portion of the conjugate (Daltons) | Conjugated Biologically Active Agent |
|---|---|
| 5,000 | erythropoietin |
| 10,000 | erythropoietin |
| 20,000 | erythropoietin |
| 40,000 | erythropoietin |
| 5,000 | granulocyte-colony stimulating factor |
| 10,000 | granulocyte-colony stimulating factor |
| 20,000 | granulocyte-colony stimulating factor |
| 40,000 | granulocyte-colony stimulating factor |
| 5,000 | interferon alpha |
| 10,000 | interferon alpha |
| 20,000 | interferon alpha |
| 40,000 | interferon alpha |
| 5,000 | interferon beta |
| 10,000 | interferon beta |
| 20,000 | interferon beta |
| 40,000 | interferon beta |
| 5,000 | human growth hormone |
| 10,000 | human growth hormone |
| 20,000 | human growth hormone |
| 40,000 | human growth hormone |
| 5,000 | imiglucerase |
| 10,000 | imiglucerase |
| 20,000 | imiglucerase |
| 40,000 | imiglucerase |

Example 33

Taxol Conjugates

Taxol, which bears two hydroxyl groups is be conjugated to the homopolymers bearing a free reactive carboxyl group prepared in Example 21, part 2a of 1,000, 2,000, 5,000, 10,000, 20,000 or 40,000 Daltons.

Taxol is conjugated to the homopolymers dissolved in HEPES buffer at about pH 7.2 by adding about 0.95 to about 0.98 mmol of EDC for each 1 mmol of homopolymer bearing a carboxyl group to form an EDC activated carboxyl group on the homopolymer. In order to avoid having more than one taxol hydroxyl group conjugated to the homopolymer, the activated homopolymer is added slowly with stirring to a 1.2 molar excess of the taxol suspended in HEPES buffer. Where a large amount of the polymer conjugate is to be prepared, small portions of homopolymer having an EDC activated carboxyl group may be prepared and reacted with taxol in sequence so that the EDC activated carboxyl group (an o-acylisourea intermediate) does not decompose prior to addition. Reducing the temperature also reduces the rate of EDC activated carboxyl group hydrolysis. As conjugation proceeds the suspended taxol gradually dissolves.

Following the conjugation reaction the product taxol conjugate is purified by chromatography on Superdex Peptide or Superdex 75 using phosphate buffered saline as the mobile phase.

Those skilled in the art will recognize or be able to ascertain using no more than ordinary experimentation that there are many equivalents to the specific embodiments of the invention described herein. All patents, patent applications and references cited herein are incorporated by reference herein in their entirety.

What is claimed is:

1. A compound comprising a biologically active protein bonded to a phosphorylcholine containing polymer wherein said polymer is branched, having 3 or more polymer arms wherein each arm has from about 100 to about 2000 hydroxyethylmethacryloyl phosphorylcholine containing monomer units and molecules of the compound each contain a single molecule of the biologically active protein covalently bonded to a single molecule of the branched polymer.

2. The compound of claim 1 wherein the phosphorylcholine containing polymer is covalently bonded to at least one of an amino group, a hydroxyl group, a sulfhydryl group and a carboxyl group of the biologically active protein.

3. The compound of claim 2 wherein the polymer has 3, 4, 5, 6, 7, 8, or more polymer arms.

4. The compound of claim 3 wherein the polymer has 3 arms.

5. The compound of claim 3 wherein the polymer has 6 arms.

6. The compound of claim 3 wherein the polymer has more than 8 arms.

7. The compound of claim 3 wherein each arm has from about 20 to about 2000 monomer units.

8. The compound of claim 7 wherein each arm has from about 100 to about 500 monomer units.

9. The compound of claim 7 wherein each arm has from about 500 to about 1000 monomer units.

10. The compound of claim 7 wherein the polymer has 3 arms.

11. The compound of claim 7 wherein the polymer has 6 arms.

12. The compound of claim 7 wherein the polymer has more than 8 arms.

13. The compound of claim 1 wherein the biologically active protein is a therapeutic protein.

14. The compound of claim 13 wherein the protein is a human protein.

15. The compound of claim 14 wherein the human protein is obtained by heterologous gene expression in a cell selected from the group consisting of a bacterium, a yeast cell, a mammalian cell in culture, an insect cell in culture, a plant cell in culture, an avian cell in culture, a cell of a transgenic avian, a cell of a transgenic mammal, and a cell of a transgenic plant.

16. The compound of claim 14 wherein the human protein is obtained by gene activation in a cell line.

17. The compound according to claim 3 wherein the biologically active protein is a selected from the group consisting of a cytokine, an enzyme, an antibody and an antibody fragment.

18. The compound according to claim 17 wherein the cytokine, the enzyme, the antibody and the antibody fragment are human.

19. The compound according to claim 18 wherein the cytokine, the enzyme and antibody or antibody fragment are obtained by heterologous gene expression in a cell selected from the group consisting of a bacterium, a yeast cell, a mammalian cell in culture, an insect cell in culture, a plant cell in culture, an avian cell in culture, a cell of a transgenic avian, a cell of a transgenic chicken, a cell of a transgenic quail, a cell of a transgenic goat, a cell of a transgenic cow and a cell of a transgenic plant.

* * * * *

SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens
<220> FEATURE:
<223> OTHER INFORMATION: Human Erythropoietin (EPO)

<400> SEQUENCE: 1

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

<210> SEQ ID NO 2
<211> LENGTH: 174
<212> TYPE: PRT
<213> ORGANISM: Homo sapiens
<220> FEATURE:
<223> OTHER INFORMATION: Human Granulocyte Colony Stimulating Factor
      (G-CSF)

<400> SEQUENCE: 2

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125
```

```
Ala Leu Gln Pro Thr Gln Gly Ala Met Pro Ala Phe Ala Ser Ala Phe
    130             135             140
Gln Arg Arg Ala Gly Gly Val Leu Val Ala Ser His Leu Gln Ser Phe
145             150             155             160
Leu Glu Val Ser Tyr Arg Val Leu Arg His Leu Ala Gln Pro
                165             170
```